US007939650B2

(12) United States Patent
Pennica et al.

(10) Patent No.: US 7,939,650 B2
(45) Date of Patent: *May 10, 2011

(54) STRA6 POLYPEPTIDES

(75) Inventors: Diane Pennica, Burlingame, CA (US); Victoria Smith, Burlingame, CA (US); William I. Wood, Cupertino, CA (US)

(73) Assignee: Genentech, Inc., South San Francisco, CA (US)

( * ) Notice: Subject to any disclaimer, the term of this patent is extended or adjusted under 35 U.S.C. 154(b) by 909 days.

This patent is subject to a terminal disclaimer.

(21) Appl. No.: 11/458,181

(22) Filed: Jul. 18, 2006

(65) Prior Publication Data

US 2008/0299547 A1 Dec. 4, 2008

Related U.S. Application Data

(62) Division of application No. 09/759,056, filed on Jan. 11, 2001, now Pat. No. 7,173,115.

(60) Provisional application No. 60/228,914, filed on Aug. 29, 2000, provisional application No. 60/197,089, filed on Apr. 14, 2000, provisional application No. 60/175,849, filed on Jan. 13, 2000.

(51) Int. Cl.
C07H 21/02 (2006.01)
C07H 21/04 (2006.01)
A61K 39/00 (2006.01)

(52) U.S. Cl. ...... 536/23.5; 536/23.1; 530/300; 530/350; 424/9.1; 424/9.2; 424/130.1; 424/138.1; 424/184.1; 424/185.1; 424/277.1

(58) Field of Classification Search .................. 424/9.1, 424/9.2, 130.1, 138.1, 184.1, 185.1, 277.1; 530/300, 350; 536/23.1, 23.5
See application file for complete search history.

(56) References Cited

U.S. PATENT DOCUMENTS

| 3,773,919 A | 11/1973 | Boswell et al. |
| 4,179,337 A | 12/1979 | Davis et al. |
| 4,275,149 A | 6/1981 | Litman et al. |
| 4,399,216 A | 8/1983 | Axel et al. |
| 4,485,045 A | 11/1984 | Regen |
| 4,496,689 A | 1/1985 | Mitra |
| 4,544,545 A | 10/1985 | Ryan et al. |
| 4,640,835 A | 2/1987 | Shimizu et al. |
| 4,657,760 A | 4/1987 | Kung et al. |
| 4,670,417 A | 6/1987 | Iwasaki et al. |
| 4,676,980 A | 6/1987 | Segal et al. |
| 4,736,866 A | 4/1988 | Leder et al. |
| 4,791,192 A | 12/1988 | Nakagawa et al. |
| 4,816,567 A | 3/1989 | Cabilly et al. |
| 4,870,009 A | 9/1989 | Evans et al. |
| 4,873,191 A | 10/1989 | Wagner et al. |
| 4,943,529 A | 7/1990 | Van Den Berg et al. |
| 4,975,278 A | 12/1990 | Santer et al. |
| 4,997,852 A | 3/1991 | Minton et al. |
| 5,010,182 A | 4/1991 | Brake et al. |
| 5,013,556 A | 5/1991 | Woodle et al. |
| 5,122,469 A | 6/1992 | Mather et al. |
| 5,206,344 A | 4/1993 | Katre et al. |
| 5,225,212 A | 7/1993 | Martin et al. |
| 5,428,130 A | 6/1995 | Capon et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,654,010 A | 8/1997 | Johnson et al. |
| 5,661,016 A | 8/1997 | Lonberg et al. |
| 6,187,819 B1 | 2/2001 | Fisher et al. |
| 2003/0021788 A1 | 1/2003 | Pennica et al. |
| 2003/0149239 A1 | 8/2003 | Baker et al. |
| 2003/0187201 A1 | 10/2003 | Baker et al. |
| 2003/0187202 A1 | 10/2003 | Baker et al. |
| 2003/0187203 A1 | 10/2003 | Baker et al. |

FOREIGN PATENT DOCUMENTS

| EP | 36776 | 9/1981 |
| EP | 073657 | 3/1983 |
| EP | 117058 | 8/1984 |
| EP | 117060 | 8/1984 |
| EP | 139383 | 5/1985 |
| EP | 307247 | 3/1988 |
| EP | 362 179 | 4/1990 |
| EP | 03089 | 5/1990 |
| EP | 394538 | 10/1990 |
| EP | 404097 | 12/1990 |
| EP | 616 812 | 9/1994 |
| WO | WO 81/01145 | 4/1981 |
| WO | WO 87/05330 | 9/1987 |

(Continued)

OTHER PUBLICATIONS

Bouillet, P. et al. Mechanisms of Development, vol. 63, pp. 173-186, 1997.*
Alberts et al., "Gene Expression Can Be Controlled by a Change in mRNA Stability", *Molecular Biology of the Cell*, Chap. 9, pp. 464-466 (1994).
Alitalo et al., "Oncogene Amplification in Tumor Cells", *Adv. Cancer Res.*, 47:235-281 (1986).
Altschul et al., "Gapped BLAST and PSI-BLAST: a new generation of protein database search programs", *Nucleic Acids Res.* 25(17):3389-3402 (1997).
American Cancer Society, *Cancer Facts and Figures*, Atlanta, Georgia: American Cancer Society, Inc., pp. 1-44 (2002).
Anderson et al., "Direct Interactions of Coxsakievirus B3 with Immune Cells in the Splenic Compartment of Mice Susceptible or Resistant to Myocarditis", *Science* 256, 808-813 (1992).

(Continued)

*Primary Examiner* — Rodney P. Swartz
(74) *Attorney, Agent, or Firm* — Merchant & Gould P.C.

(57) ABSTRACT

The present invention is directed to novel polypeptides having sequence similarity to Stra6, a murine retinoic acid responsive protein, and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

23 Claims, 35 Drawing Sheets

FOREIGN PATENT DOCUMENTS

| WO | WO 88/07378 | 10/1988 |
| --- | --- | --- |
| WO | WO 89/05859 | 6/1989 |
| WO | WO 90/10048 | 9/1990 |
| WO | WO 90/13641 | 11/1990 |
| WO | WO 90/13646 | 11/1990 |
| WO | WO 9L/00360 | 1/1991 |
| WO | WO 91/00357 | 1/1991 |
| WO | WO 91/04753 | 4/1991 |
| WO | WO 93/11161 | 6/1993 |
| WO | WO 93/17041 | 9/1993 |
| WO | WO 93/18186 | 9/1993 |
| WO | WO 94/11026 | 5/1994 |
| WO | WO 84/03564 | 9/1994 |
| WO | WO 95/32221 | 11/1995 |
| WO | WO 96/07399 | 3/1996 |
| WO | WO 96/27011 | 9/1996 |
| WO | WO 96/40072 | 12/1996 |
| WO | WO 97/03692 | 2/1997 |
| WO | WO 97/33551 | 9/1997 |
| WO | WO 98/54963 | 12/1998 |
| WO | WO 99/47162 | 9/1999 |
| WO | WO 01/12660 A2 | 2/2001 |

OTHER PUBLICATIONS

Aquino et al., "Effect of the Combined Treatment with 5-Fluorouracil, γ-Interferon or Folinic Acid on Carcionoembryonic Antigen Expression in Colon Cancer Cells", *Clinical Cancer Research*, 4(10): 2473-2481 (Oct. 1998).

Athauda et al., "Entrapment and Inhibition of Human Immunodeficiency Virus Proteinase by a 2-Macroglobulin and Structural Changes in the Inhibitor", *J. Biochem.*, 113:742-746 (1993).

Ausubel et al., *Current Protocols of Molecular Biology*, John Wiley and Sons (1997).

Barker et al., "The Yin-Yang of TCF/β-Catenin Signaling", *Adv. Cancer Res.*, 77:1-24 (2000).

Baselga et al., "Phase II Study of Weekly Intravenous Recombinant Humanized Anti-pi 85her2 Monoclonal Antibody in Patients With HER2/neu-Overxpressing Metastatic Breast Cancer", *J. Clin. Oncol.*, 14:737-744 (1996).

Baselga et al., "HER2 Overexpression and Paclitaxel Sensitivity in Breast Cancer: Therapeutic implications", *Oncology*, 11(3 Suppl 1):43-48 (1997).

Beach at al., "High-frequency transformation of the fission yeast *Schizosaccharomyces pombe*", *Nature*, 290:140 (1981).

Beal et al., "Second Structural Motif for Recognition of DNA by Oligonucleotide-Directed Triple-Helix Formation", *Science*, 251:1360(1991).

Beckmann et al., "Molecular characterization of a family of ligands for eph-related tyrosine kinase receptors", *EMBO J.*, 13:3657 (1994).

Behrens et al., "Functional Interaction of β-catenin with the transcription factor LEF-1", *Nature*, 382:638-642 (1996).

Bergstein et al., "Isolation of Teo Novel WNT Genes, WNT14 and wnt15, One of Which (WNT15) Is Closely linked to WNT3 on Human Chromosome 17q21", *Genomics*, 46:450-458 (1997).

Bidyut Roy et al., "Synergistic Activation of Retinoic Acid (RA)-Responsive Genes and Induction of Embryonal Carcinoma Cell Differentiation by a RA Receptor α (RARα)-, RARβ- or RARγ-Selective Ligand in Combination with a Retinoid X Receptor-Specific Ligand", *Mol. Cell. Biol.*, 15(12):6481-7 (1995).

Bishop, Michael J., "Molecular Themes in Oncogenesis", *Cell*, 64:235-248 (1991).

Blast Alignments of SEQ ID No. 1 and SEQ ID No. 4 with sequences of AI 684707; AI 760170 and SEQ ID No. 36 of WO 98/54963 dated Jan. 29, 2004.

Boerner et al,, "Production of antigen-specific human monoclonal antibodies from in vitro-primed human splenocytes", *J. Immunol.*, 147(1):86-95 (1991).

Bolivar et al., "Construction and characterization of new cloning vehicles", *Gene*, 2:95-113 (1977).

Boring et al., "Cancer Statistics, 1993", *CA Cancel J. Clin.*, 43:7 (1993).

Bouillet at al., "Efficient Cloning of cDNA of Retinoic Acid-Responsive Genes in P19 Embryonal Carcinoma Cells and Characterization of a Novel Mouse Gene, Stral (Mouse LERK-2/Eplg2)", *Dev. Biol.*, 170:420-433 (1995).

Bouillet at al., "Developmental expression pattern of Stra6, a retinoic acid-responsive gene encoding a new type of membrane protein", *Mechanisms of Development*, 63:173-186 (1997).

Boven and Winograd, eds., *The Nude Mouse in Oncology Research*, CRC Press, Inc., 1991.

Bowie, J. et al., "Deciphering the Message in Protein Sequences: Tolerance to Amino Acid Substitutions", *Science*, 247:1306-1310 (1990).

Bradley, Allan, "Production and analysis of Chimaeric mice" in Teratocarcinomas and Embryonic Stem Cells: A Practical Approach, E. J. Robertson, ed. (IRL. Oxford, 1987), 5:113-152.

Braxton and Wells, "Incorporation of Stabilizing Ca2+-Binding Loop into Subtilisin BPN", *Biochemistry*, 31:7796-7801 (1992).

Brennan et al., "Preparation of Bispecific Antibodies by Chemical Recombination of Monoclonal Immunoglobulin GI Fragments", *Science*, 229:81 (1985).

Brenner et al., "Assessing Sequence Comparison Methods with reliable structurally identified distant evolutionary relationships", *Proc. Natl. Acad. Sci.*, 95:6073-6078 (May 1998).

Brown et al., "Wnt signaling in breast cancer: have we come full circle?", *Breast Cancer Res.*, 3:351-355 (2001).

Bui et al., "A novel human Wnt gene, WNT10B, maps to 12q13 and is expressed in human breast carcinomas", *Oncogene*, 14:1249-1253 (1997).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", *The Journal of Cell Biology*, 111:2129-2138 (1990).

C. Anthony, *The Biochemistry of Methylotropbs*, 269-295 (1982).

Caraglia et al., "5-Axa-2'-deoxycytidine induces growth inhibition and upregulation of epidermal growth factor receptor on human epithelial cancer cells", *Annals of Oncology*, 5(3):269-76 (1994).

Caron et al., "Engineered Humanized Dimeric Forms of IgG Are More Effective Antobodies", *J. Exp Med.*, 176:1191-1195(1992).

Carter et al., "Improved oligonucleotide site-directed mutagenesis using M13 vectors" *Nucl. Acids Res.* 13:4331 (1986).

Case et al., "Efficient Transformation of *Neurospora crassa* by Utilizing Hybrid Plasmid DNA", *Proc. Natl. Sci. USA*, 76:5259-5263 (1979).

Chang et al., "Phenotype expression in *E. coli* of a DNA sequence coding for mouse dihydrofolate reductase", *Nature*, 275:615 (1978).

Chazaud et al., "Restricted Expression of a Novel Retinoic Acid Responsive Gene During Limb Bud Dorsoventral Patterning and Endochondral Ossification", *Dev. Genet.*, 19: 66-73 (1996).

Chevray and Nathans, "Protein interaction cloning in yeast: Identification of mammalian proteins that react with leucine zipper of Jun", *Proc. Natl. Acad. Sci. USA*, 89: 5789-5793 (1991).

Chien et al., "The two-hybrid system: A method to identify and clone genes for proteins that interact with a protein of interest", *Proc. Natl. Acad. Sci. USA*, 88:9578-9582 (1991).

Chothia, Cyrus, "The Nature of the Accessible and Buried Surfaces in Proteins", *J. Mol. Biol.*, 150:1 (1976).

Chu, F-F et al., *J. Nutr.*, 129:1846-1854 (1999).

Clark et al., "Molecular Cloning of the Human Proto-oncogene Wnt-5A and Mapping of the Gene (WNTSA) to Chromosome 3p14-p21", *Genomics*, 18:249-260 (1993).

Cleland, Jeffrey L., "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), Chapter 18 pp. 439-462.

Clotman et al., "All-trans-Retinoic Acid Upregulates the Expression of COUP-TFI in Early-Somite Mouse Embryos Cultured in Vitro", *Neurotoxical Teratol*, 20:591-599 (1998).

Cooney et al., "Site-Specific Oligonucleotide Binding Represses transcription of the Human c-myc Gene in Vitro", *Science*, 241: 456-459 (1988).

Creighton, *Proteins: Structure and Molecular Properties*, W.H. Freeman & Co., San Francisco, (1983).
Cunningham and Wells, "High-Resolution Epitope Mapping of hGH-Receptor Interactions by Alanine-Scanning Mutagenesis", *Science*. 244:1081-1085 (1989).
Database EMBL 'Online! Entry/Acc.No. A17601070 Jun. 30, 1999 Strausberg R.: "wg58f06.X1 Soares-NSF-F8.9W_OT_PA_P_S1 *Homo sapiens* cDNA clone image:2369315 3'. mRNA sequence." XP002174858.
Database EMBL 'Online! Entry/Acc.No. A1684707 May 28, 1999 Strausberg R.: "wa85B10.X1 Saores-NFL_T_GBC_S1 *Homo sapiens* cDNA clone image:2302939 3'. mRNA sequence." XP0021749857.
Database GenEmbl, Accession No. AAV84436 (Mar. 1999).
Database GenEmbl, Accession No. AF062476 (May 1998)n.
David and Reisfeld, "Protein Iodination with Solid State Lactoperoxidase", *Biochemistry*, 13:1014 (1974).
Davis et al., "Ligands for EPH-Related Receptor Tyrosine Kinases That Require Membrane Attachment or Clustering for Activity", *Science*, 266:816 (1994).
deBoer et al., The tac promoter: A functional hybrid derived from the trp and lac promoters' *Proc. Natl. Acad. Sci. USA*, 80:21-25 (1983).
DeLeo et al., "Cell Surface Antigens of Chemically Induced Sarcomas of the Mouse" *J. Exp. Med.*, 146:720-730 (1977).
Dennis et al., "A secreted Frizzled related protein, FrzA, selectively associates with Wnt-1 protein and regulates Wnt-1 signaling", *Journal of Cell Science*, 112:3814-3820 (1999).
Deutscher, Murray P. (Ed.), *Methods in Enzymology*, 182 (1990).
Donehower et al., "Deficiency of p53 accelerates mammary tumorigenesis in Wnt-1 transgenic mice and promotes chromosomal instability", *Genes Dev.*, 9:882-895 (1995).
Drebin et al., "Inhibition of tumor growth by a monoclonal antibody reactive with an oncogene-encoded tumor antigen", *Proc. Natl. Acad. Sci. USA*, 83:9129-9133 (1986).
Drebin et al., "Monoclonal antibodies identify a cell-surface antigen associated with an activated cellular oncogene", *Nature*, 312(5994):545-8 (1984).
Duester, Gregg, "Families of retinoid dehydrogenases regulating vitamin A function production of visual pigment and retinoic acid", *Eur. J. Biochem.*, 267:4315-4324 (2000).
Easwaran et al., "Cross-regulation of -catenin-LEF/TCF and retinoid signaling pathways", *Curr. Biol.*, 9:1415-1418 (1999).
Eberhard et al., "Alterations of Annexin Expression in Pathological Neuronal and Glial Reactions", *Am. J. Pathol.*, 145:640-9 (1994).
Edge et al. "Deglucosylation of Glycoproteins by Trifluoromethanesulfonic Acid", *Anal. Biochem.*, 118:131-137 (1981).
Epstein et al. "Biological activity of liposome encapsulated murine interferon is mediated by a cell membrane receptor", *Proc. Natl. Acad. Sci. USA*, 82: 3688 (1985).
Evan et al., "Isolation of Monoclonal Antibodies Specific for Human c-myc Proto-Oncogene Product", *Molecular and Cellular Biology*, 5:3610-3616 (1985).
Fear et al., "Wnt-16a, a Novel Wnt-16 Isoform, Which Shows Differential Expression in Adult Human Tissues", *Biochem. Biophys. Res. Commun.*, 278:814-820 (2000).
Field et al., "Purification of a RAS-Responsive Adenylyl Cuclase Complez from *Saccharomyces cerevisiae* by Use of an Epitope Addition Method", *Mol. Cell. Biol.*, 8:2159-2165 (1988).
Fields and Song, "A novel genetic system to detect protein-protein interactions", *Nature*, 340:245-246 (1989).
Fishwild et al., "High-avidity human IgGk monoclonal antibodies from a novel strain of minilocus transgenic mice", *Nature Biotechnology*, 14:845-51 (1996).
Fleer et al., "Stable Multicopy Vectors for High Level Secretion of Recombinant Human Serum Albumin by Kluyveromyces Yeasts", *Bio/Technology*, 9:968-975 (1991).
Fournier et al., "Structure and Organization of the Transfer Ribonucleic Acid Genes of *Escherichia coli* K-12", *Microbiol. Rev.*, 49:379-397 (1985).
Freund and Blair "Depression of Natural Killer Activity and Mitogen Responsiveness in Mice Treated With Pristane", *J. Immunol.*, 129:2826-2830 (1982).

Fu et al., "Translational regulation of human p53 gene expression", *EMBO Journal*, 15(16)4392-4401 (1996).
Gabizon et al., "Pharmacokinetics and Tissue Distribution of Doxorubicin Encapsulated in Stable Liposomes With Long Circulation Times", *J. National Cancer Inst.*, 81(19): 1484 (1989).
Gelmini et al., "Quantitative polymarase chain reaction-based homogeneous assay with fluorogenic probes to measure c-erbB-2 oncogene amplification", *Clin. Chem.*, 43:752 (1997).
Gething et al., "Cell-surface expression of influenza haemagglutinin from a cloned DNA copy of the RNA gene", *Nature*, 293:620-625 (1981).
Glennie et al., "Clinical trials of antibody therapy", *Immunol. Today*, 21:403-410 (2000).
Goeddel et al., "Direct expression in *Escherichia coli* of a DNA sequence coding for human growth hormone", *Nature*, 281:544 (1979).
Goeddel et al., "Synthesis of human fibroblast by *E. coli*" Nucleic Acids Res., 8:4057 (1980).
Graham et al. "Characteristics of a Human Cell Line Transformed by DNA from human Adenovirus Type 5", *J. Gen Virol.*, 36:59 (1977).
Gray et al. "Fluorescence in Situ Hybridization in Cancer and Radiation Biology", *Radiation Res.*, 137:275-289 (1994).
Gruber et al "Efficient Tumor Cell Lysis Mediated by a Bispecific Single Chain Antibody Express in *Escherichia coli*", *J. Immunol.*, 152:5368 (1994).
He et al., "Identification of c-MYC as a Target of the APC Pathway", *Science*, 281:1509-1512 (1998).
Heid et al., "Real time quantitative PCR", *Genome Res.*, 6:986-94 (1996).
Hess et al., "Cooperation of Glycolytic Enzymes", *J. Adv. Enzyme Reg.*, 7:149 (1968).
Hitzeman et al., "Isolation and Characterization of the Yeast 3-Phosphoglycerokinase Gene (PGK) by Immunological Screening Technique", *J. Biol. Chem.*, 255:2073 (1980).
Hodgson, John, "Data-Directed Drug Design", *Bio/Technology*, 9: 19-21 (1991).
Holland and Holland, "Isolation and Identification of yeast Messenger Ribonucleic Acids Coding for Enolase, Glyceraldehyde-3-phosphate Dehydrogenase and Phosphoglucerate Kinase", *Biochemistry*, 17:4900-4907 (1978).
Hollinger et al., "Diabodies": Small bivalent and bispecific antibody fragments, *Proc. Natl. Acad. Sci. USA*, 90:6444-6448 (1993).
Hongo et al., "Development and Characterization of Murine Monoclonal Antibodies to the Latency-Associated Peptide of Transforming Growth Factor", *Hybridoma*, 14:253-260 (1995).
Hopp et al., "A short polypeptide marker sequence useful for recombinant protein identification and purification", *BioTechnology*, 6:1204-1210 (1988).
Hora et al., "Controlled Release of Interleukin-2 From Biodegradable Microspheres", *Bio/Technology*, 8:755-758 (1990).
Hsiao et al., "High-frequency transformation of yeast by plasmids containing the cloned yeast ARG4 gene", *Proc. Natl. Acad. Sci. (USA)*, 76:3829 (1979).
Huguet et al., "Differential Expression of Human Wnt Genes 2,3,4 and 7B in Human Breast Cell Lines and Normal and disease States of Human Breast Tissue", *Cancer Res.*, 54:2615-2521 (1994).
Hunter, "Cooperation between Oncogenes", *Cell*, 64:1129 (1991).
Hwang et al. "Hepatic uptake and degradation of unilamellar sphingomyelin/cholesterol liposomes: A kinetic study", *Proc. Natl Acad. Sci. USA*, 77: 4030 (1980).
Hynes and Stern, "The biology of erbB-2/neu/HER-2 and its role in cancer", *Biochim. Biophys. Acta.* 1198:165-184 (1994).
Ikegawa et al., "Isolation, characterization and chromosomal assignment of the human WNT7A gene", *Cytogenet. Cell. Genet.*, 74:149-152 (1996).
Johnson et al., "A month-long effect from a single injection of microencapsulated human growth hormone", *Nat. Med.*, 2:795-799 (1996).
Jones et al., "Replacing the complementary-determining regions in a human antibody with those from a mouse", *Nature*, 321:522-525 (1986).
Jones, Elizabeth W., "Proteinase Mutants of *Saccharomyces cerevisiae*", *Genetics*, 85:12 (1977).

Kantor et al., "Modulation of Carcinoembryonic Antigen Messenger RNA Levels in Human Colon Carcinoma Cells by Recombinant Human y-Interferon", *Cancer Research*, 49(1):2651-5 (1989).

Karmali et al., "Prostaglandins in breast cancer: Relationship to disease stage and hormone status", *Br. J. Cancer*, 48:689-696 (1983).

Katoh et al., "Cloning expression and chromosomal localization of Wnt-13, a novel member of the Wnt gene family", *Oncogene*, 13:873-876 (1996).

Kelly and Hynes, "Transformation osf *Aspergillus niger* by the amdS gene of *Aspergillus nidulans*" *EMBO J.*, 4:475-479(1985).

Keown et al., "Methods for Introducing DNA into Mammalian Cells", *Methods in Enzymology*, 185:527-537 (1990).

Kikuchi et al., "The nucleotide sequence of the promoter and the amino-terminal region of alkaline phosphatase structural gene (phoA) of *Escherichia coli*", *Nucleic Acids Res.*, 9:5671-5678 (1981).

Kim et al., "Anti4-IBB Monoclonal Antibodies Enhance Antitumor Efficacy of Adoptive Immunotherapy Using Tumor-Draining Lymph Node Cells", *Proc. Am. Assoc. Cancer Res.*, 41, 91 Meet., 290, 2000 (Conference abstract:91$^{st}$ Annual Meeting of the American Association for Cancer Research, San Francisco, California, USA, 2001.

Kingsman et al. "Replication In *Saccharomyces cerevisae* of Plasmid Pbr313 Carrying DNA from the Yeast trpl Region", *Gene*, 7:141 (1979).

Kobayashi et al., "Mutations of the β-Catenin Gene in Endometrial Carcinomas" *Jpn. J. Cancer Res.*, 90:55-9 (1999).

Koesters et al., "Mutational Activation of the β-Catenin Proto-Oncogene Is a Common Event in the Development of Wilms' Tumors", *Cancer Res.*, 59:3880-2 (1999).

Koj et al., "Regulation of Synthesis of Some Proteinase Inhibitors in Human Hepatome Cells HepG2 by Cytokines, Hepatocyte Growth Factor", *Biol. Chem. Hoppe. Syler.*, 374:193-201 (1993).

Komine et al., "Genomic Organization and Physical Mapping of the Transfer RNA Genes In *Escherichia coli* K12", *J. Mol. Biol.*, 212:579-598 (1990).

Korinek et al., "Constitutive Transcriptional Activation by a β-Catenin-Tcf Complex in APC-/-Colon Carcinoma", *Science*, 275:1784-1787 (1997).

Korinek et al., "Two members of the Rcf family implicated in Wnt/β-Catenin signaling during Embryogenesis in the Mouse", *Mol. Cell Biol.*, 18:1248-56 (1998).

Kostelny et al. "Formation of a Bispecific Antibody by the Use of Leucine Zippers", *J. Immunol.*, 148(5):1547-1553 (1992).

Lako et al., "Isolation and Characterization of WNT8B, a Novel Human Wnt Gene That Maps to 10q24", *Genomics*, 35:386-388 (1996).

Lako et al., "Isolation, characterization and embryonic expression of WNT11, a gene which maps the 11q13.5 and has possible roles in the development of skeleton, kidney and lung", *Gene*, 219:101-110 (1998).

Lasko et al., "Targeted oncogene activation by site-specific recombination in transgenic mice", *Proc. Natl. Acad. Sci. USA*, 89:6232-636 (1992).

Lassam et al., "Synthesis of DNA, Late Polypeptides, and Infectious Virus by Host-Range Mutants of Aenovirus 5 in Nonpermissive Cells", *Virology*. 87:63-467 (1978).

Lavitrano et al., "Sperm Cells as vectors for Introducing Foreign DNA into Eggs: Genentic Transformation of Mice", *Cell*, 57:717-73 (1989).

Lee et al., "Cloning, Chromosomal Localization, and Tissue Expression of Autotaxin from human Teratocarcinoma Cells", *Biochem. Biophys. Res. Commun.*, 218:714-719 (1996).

Lee et al., "Complexes formed by (pyrimidine)n.(purine)n DNAs on lowering the pH are three-stranded", *Nucl. Acids Res.*, 6:3073 (1979).

Li et al., "Targeted Mutation of the DNA Methytransferase Gene Results in Embryonic Lethality", *Cell*, 69:915 (1992).

Lo, Cecilia W., "Transformation by Iontophoretic Microinjection of DNA: Multiple Integration Without Tandem insertions", *Mol. Cell Biol.*, 3:1803-1814 (1983).

Lonberg and Huszar, "Human Antibodies from transgenic Mice", *Intern. Rev. Immunol.*, 13 65-93 (1995).

Lonberg et al., "Antigen-specific human antibodies from mice comprising four distinct genetic modifications", *Nature*, 368 856-859 (1994).

Louvencourt et al., "Transformation of *Kluyveromyces lactis* by Killer Plasmid DNA", *J. Bacteriol.*, 154(2):1737-1742 (1983).

Lucas et al., "High-Level production of recombinant proteins in CHO cells using a dicistronic DHFR intron expression vector", *Nucl. Acids Res.*, 24(9 );1774-1779 (1996).

Lutz-Freyermulh et al., "Quantitative determination that one of two potentail RNA-binding domains of the A protein component of the U1 small nuclear ribonucleoprotein complex binds with high affinity to stem-loop II OF U1 RNA", *Proc. Natl. Acad. Sci. USA*, 87:6393-6397 (1990).

Mallampalli, R. et al., "Betamethasone modulation of sphingomyelin hydrolysis up-regulates CTP:cholinephosphate cytidylyltransferase activity in adult rat lung", *Biochem. J.*, 318:333-341 (1996).

Mansour et al., "Disruption of the proto-oncogene int-2 in mouse embryo-derived stem cells: a general strategy for targeting mutations to non-selectable genes", *Nature*, 336:348-352 (1988).

Mantei et al., "Rabbit-globin mRNA production in mouse L cells transformed with clone rabbit-globin chromosomal DNA", *Nature*. 281:40-46 (1979).

Marasco et al. "Design, intracellular expression, and activity of a human anti-human immunodeficiency virus type 1 gp120-single-chain antibody", *Proc. Natl. Acad. Sci.* USA, 90: 7889-7893 (1993).

Marks et al., "By-passing Immunization Human Antibodies from V-gene Libraries Displayed on Phage", *J. Mol. Biol.*, 222:581 (1991).

Martin and Papahadjopoulos, "Irreversible Coupling of Immunoglobulin Fragments to Preformed Vesicles", *J. Biol. Chem.*, 257:286-288 (1982).

Martin et al., "GAP Domains Responsible for Ras p21 -Dependent Inhibition of Muscarinic Atrial K+ Channel Current", *Science*, 255:192-194 (1992).

Martin-Satue et al., "Identification of Semaphorin E Gene Expression in Metastatic Human Lung Adenocarcinoma Cells by mRNA Differential Display", *J. Surg. Oncol.*, 72:18-23 (1999).

Massey, "Catalytic antibodies catching on", *Nature*, 328:457-458 (1987).

Mather, Jennie P. "Establishment and Characterization of two Distinct Mouse Testicular Epithelial Cell Lines", *Biol. Reprod.*, 23:243-251 (1980).

McGrew et al., "Direct regulation of the *Xenopus* engrailed- 2 promoter by the Wnt signaling pathway, and a molecular screen for Wnt-responsive genes, confirm a role for Wnt signaling during neural patterning in *Xenopus*", *Mech. Dev.*, 87:21-32(1999).

McWhirter et al., "Oncogenic homeodomain transcription factor E2A-Pbx1 activates a novel WNT gene in pre-B acute lymphoblastoid leukemia", *Proc. Natl. Acad. Sci. USA*, 96:11464-11469 (1999).

Merrifield, R.B., "Solid Phase Peptide Synthesis. I. The Synthesis of Tetrapeptide", *J. Am. Chem, Soc.*, 85:2149-2154 (1963).

Miller et al., "Signal transduction through β-catenin and specification of cell fate during embryogenesis", *Genes & Dev.*, 10:2527-2539 (1996).

Milstein and Cuello, "Hybrid hybridomas and their use in immunohistochemistry", *Nature*, 305:537-539 (1983).

Molenaar et al., "XTcf-3 Transcription Factor Mediates β-Catenin-Induced Axis Formation in *Xenopus* Embryos", *Cell*. 86:391-399 (1996).

Moon, R. et al., "The Promise and Perils of Wnt Signaling Through β-Catenin", *Science*, 296:1644-1646 (2002).

Mordenti, J. and Chappell, W. "The use of interspecies scaling in toxicokinetics", *In Toxicokinetics and New Drug Development*, Yacobi et al., Eds., Pergamon Press, New York 1989, pp. 42-96.

Morin et al., "Activation of β-Catenin-Tcf Signaling in Colon Cancer by Mutations in β-Catenin or APC", *Science*, 275:1787-1790 (1997).

Morrison, Sherrie L., "Success in specification", *Nature*, 368, 812-13 (1994).

Moss, "Nomenclature of Retinoids", *Arch. Biochem. Biophys.*, 224:728-731 (1983).

Moss, "Nomenclature of Retinoids", *Biochemical Nomenclature and Related Documents*, 2$^{nd}$ edition, Portland Press, 1992, pp. 247-251.

Moss, "Nomenclature of Retinoids", *Eur. J. Biochem.*, 129:1-5 (1982).
Moss, "Nomenclature of Retinoids", *J. Biol. Chem.*, 258:5329-5333 (1983).
Moss, "Nomenclature of Retinoids", *Pure App. Chem.*, 55:721-726 (1983).
Murata et al., "cDNA Cloning of the Human Tumor Motility-stimulating Protein, Autotaxin, Reveals a Homology with Phosphodiesterases", *J. Biol. Chem.*, 269:30479-30484 (1994).
Nagasawa et al., "Cloning of the cDNA for a New Member of the Immunoglobulin Superfamily (ISLR) Containing Leucine-Rich Repeat (LRR)", *Genomics*, 44:273-279 (1997).
Nagasawa et al., "Human and Mouse ISLR (Immunoglobulin Superfamily) Containing Leucine-Rich Repeat Genes: Genomic Structure and Tissue Expression", *Genomics*, 61:37-43 (1999).
Nagpal and Chandraratna, "Retinoids as Anti-Cancer Agents", *Current Pharmaceutical Design*, Bentham Science Publishers, 2:295-316 (1996).
Nam et al., "Autotaxin 9ATX, a potent tumor motogen, augments invasive and metastatic potential of ras-transformed cells", *Oncogene*, 19:241-247 (2000).
Neuberger et al., "Recombinant antibodies possessiong novel effector functions", *Nature*, 312:604-608 (1984).
Neuberger, Michael, "Generating high-avidity human Mabs in mice", *Nature Biotechnology*, 14:826 (1996).
Nusse et al., "Many Tumors Induced by the Mouse Mammary Tumor Virus Contain a Provirus Integrated in the Same Region of the Host Genome", *Cell*, 31:99-109 (1982).
Nusse, R. et al., "Wnt Genes", *Cell*, 69:1073-1087 (1992).
Nygren, Hakan, "Conjugation of Horseradish Peroxidase to Fab Fragments with Different Homobifunctional and Heterobifunctional Cross-Linking Reagents", *J. Histochem. and Cytochem.*, 30:407 (1982).
Paborsky et al., "Mammalian cell transient expression of tissue factor for the production of antigen", *Protein Engineering*, 3(6):547-553 (1990).
Pain and Surolia "Preparation of Protein A-Pereoxidase Monoconjugate using a Heterobifunctional Reagent, and its use in Enzyme Immunoassays", *J. Immunol. Meth.*, 40:219 (1981).
Palacios et al., "Mutations in the β-Catenin Gene (CTNNB1) in Endometroid Ovarian Carcinomas", *Cancer Res.*, 58:1344-1347 (1998).
Palladino et al. "Characterization of the Antitumor Activities of Human Tumor Necrosis Factor- and the Comparison with other Cytokines: Induction of Tumor-Specific Immunity", *J. Immunol.*, 138:4023-4032 (1987).
Pearson et al., "Differential Regulation of Biglycan and Decorin by Retinoic Acid in Bovine Chondrocytes", *J. Biol. Chem.*, 267:25364-25370 (1992).
Peifer et al., "Wnt Signaling in Oncogenesis and Embryogenesis- A Look Outside the Nucleus", *Science*, 287:1606-1609 (2000).
Pennica et al., "WISP genes are members of the connective tissue growth factor family that are up-regulated in Wnt-1-transformed cells and aberrantly expressed in human colon tumors", *Proc. Natl. Acad. Sci USA*, 95:14717-22 (1998).
Perry, M.C., Ed., Chemotherapy Source Book, Williams & Wilkins, Baltimore, MD (1992).
Polakis, Paul, "The oncogenic activation of β-catenin", *Curr. Opin. Genet. Dev.*, 9:15-21 (1999).
Polakis, Paul, "Wnt signaling and cancer", *Genes Dev.*, 14:1837-1851 (2000).
Presta, Leonard G., "Antibody engineering", *Curr. Op. Struct. Biol.*, 2:593-596 (1992).
Prete et al., "Drug-Induced Changes of Carcinoembryonic Antigen Expression in Human Cancer Cells: Effect of 5-Fluorouracil", *Journal of Pharmacology and Experimental Therapeutics*, 279(3):1574-1581 (1996).
Rankin et al., "Partial cloning and assignment of WNT6 to human chromosome band 2q35 by in situ hybridization", *Cytogenet. Cell. Genet.*, 84:50-52 (1999).

Ravdin and Chamness, "The c-erbB-2 proto-oncogene as a prognostic and predictive marker in breast cancer: a paradigm for the development of other macromolecular markers-a review", *Gene*, 159:19-27 (1995).
Reichmann et al., "Reshaping human antibodies for therapy", *Nature*, 332:323-329 (1988).
Rimm et al., "Frequent Nuclear/Cytoplasmic Localization of -Catenin without Exon 3 Mutations in Malignant Melanoma", *Am. J. Pathol.*, 154:325-9 (1999).
Rochette-Egly et al., "The AF-1 and AF-2 Activating Domains of Retinoic Acid Receptor-α (RAR-α) and Their Phosphorylation Are Differentially Involved in Parietal Endodermal Differentiation of F9 Cells and Retinois-Induced Expression of Target Genes", *Mol. Endocrinol.*, 14(9):1398-1410 (2000).
Roelink et al., "Molecular Cloning and Chromosomal Localization to 17q21 of the Human WNT3 Gene", *Genomics*, 17:790-792 (1993).
Roose et al., "Synergy Between Tumor Suppressor APC and the β-Catenin-Tcf4 target Tcf1", *Science*, 285:1923-1926 (1999).
Rossi, John J., "Making ribozymes work in cells", *Current Biology*, 4:469-471 (1994).
Rubinfeld et al., "Association of the APC Gene Product with β-Catenin", *Science*, 262:1731-1734 (1993).
Rubinfeld et al., "Stabilization of β-Catenin by Genetic Defects in Melanoma Cell Lines", *Science*, 275:1790-1792 (1997).
Ruppert et al.,"Cloning and Expression of human $TAF_{II}250$: a TBP-associated factor implicated in cell-cycle regulation", *Nature*, 362:175-179(1993).
Sakanaka et al., "New steps in the Wnt/beta-catenin signal transduction pathway", *Recent Prog. Horm. Res.*, 55:225-236 (2000).
Sambrook et al., *Molecular Cloning: A Laboratory Manual* (New York: Cold Spring Harbor Laboratory Press, 1989.
Scholtissek and Grosse, "A cloning cartridge of to terminator", *Nucleic Acids Res.*, 15:3185 (1987).
Schwab et al. "Amplification of Cellular Oncogenes: A Predictor of Clinical outcome in Human Cancer", *Genes Chromosomes Cancer*, 1:181-193 (1990).
Scopes, Robert K., *Protein Purification: Principles and Practice*, Springer-Verlag, New York (1982).
Scott, D. et al., "The Pendred syndrome gene encodes a chloride-iodide transport protein", *Nature Genetics*, 21:440-443 (1999).
Shalaby et al., "Development of Humanized Bispecific Antibodies Reactive with Cytotoxic lymphocytes and Tumor Cells Overexpressing the HER2 Protooncogene", *J. .Exp; Med.*, 175:217-225 (1992).
Shimkets et al., "Gene expression analysis by transcript profiling coupled to a gene database query", *Nat Biotechnol.*, 17:798-803 (1999).
Shopes, Bob, "A Genetically Engineered Human IgG Mutant With Enhanced Cytolytic Activity", *J. lmmunol.*, 148:2918-2922 (1992).
Skolnick et al., *Trends in Biotech*, 18(1):34-39 (2000).
Slamon et al., "Human Breast Cancer Correlation of Relapse and Survival with Amplification of the HER-2/neu Oncogene", *Science*, 235:177-182 (1987).
Small et al., "Analysis of a Transgenic Mouse Containing Simian Virus 40 and v-myc Sequences", *Mol. Cell. Biol.*, 5:642-648 (1985).
Smalley, M. et al., "Wnt Signaling and Mammary Tumorigenesis", *Journal of Mammary Gland Biology and Neoplasia*, 6(1):37-52 (2001).
Smolich et al., "Regulated Expression of Wnt Family Members during Neuroectodermal Differentiation of P19 Embryonal Carcinoma Cells: Overexpression of Wnt-1 Perturbs Normal Differentiation—Specific Properties", *Dev. Biol.*, 166:300-310 (1994).
Sojar and Bahl, et al., "A Chemical Merited for the Deglucosylation of Proteins", *Arch. Biochem. Biophys.*, 259:52-57(1987).
Somparyrac et al., "Efficient infection of monkey cells with DNA of simian virus 40", *Proc. Natl. Acad. Sci.*, 12:7575(1981).
Sreekrishna et al., "High level expression of heterologous proteins in methylotrophic yeast *Pichia pastoris*", *J. Basic Microbiol.*, 28:265-278 (1988).
St-Arnaud et al., "The *int-1* proto-oncogene is transcriptionally activated during neuroectodermal differentiation of P19 mouse embryonal carcinoma cells", *Oncogene*, 4(9):1077-1080 (1989).
Stearns et al., "Liazarole and 13-cis-Retinoid Acid Anti-Prostatic Tumor Activity", *Cancer Research*, 53(13):3072-3077 (Jul. 1993).

Stella et al., "Prodrugs: A Chemical Approach to Targeted Drug Delivery", University of Kansas and Interx Research Corp., Lawrence, Kansas 66045.

Stevenson et al. "A chimeric antibody with dual Fc regions (bisFaFc) prepared by manipulations at the IgG hinge", *Anti-Cancer Drug Design*, 3: 219-230 (1989).

Stewart et al., "An STS-Based Radiation Hybrid Map of the Human Genome", *Genome Research*, 7:422-433 (1997).

Stewart et al., *Solid-Phase Peptide Synthesis*, W.H. Freeman Co., San Francisco, CA (1969).

Stinchcomb et al., "Isolation and characterization of yeast chromosomal replicator", *Nature*, 282:39 (1979).

Suresh et al., "Bispecific Monoclonal Antibodies from Hybrid Hybridomas", *Methods in Enzymology*, 121:210 (1986).

Szeto et al., "Overexpression of the Retinoic Acid-Responsive Gene Stra6 Human Cancers and Its Synergistic Induction by Wnt-1 and Retinoic Acid", *Cancer Research*, 61:4197-4250 (May 15, 2001).

Taneja et al., "Reexpression of retinoic acid receptor (RAR) or overexpression of RAR or RAR in RAR -null F9 cells reveals a partial functional redundancy between the three RAR types", *Proc. Natl. Acad. Sci. USA*, 92:7854-8 (1995).

Tetsu et al., "β-Catenin regulates expression of cyclin D1 in colon carcinoma cells", *Nature*, 398:422-426 (1999).

Thimmappaya et al., "Adenovirus VAI RNA Is Required for Efficient Translation of Viral mRNAs at Late Times after infection", *Cell*, 31:543 (1982).

Thomas and Capecchi, "Site-Directed Mutagenesis by Gene Targeting in Mouse Embryo-Derived Stem Cells", *Cell*, 51:503(1987).

Thomas, Patricia S., "Hybridization of denatured RNA and small DNA fragments transferred to nitrocellulose", *Proc. Natl. Acad. Sci. USA*, 77:5201-5205 (1980).

Thompson et al., "Germ Line Transmission an Expression of a Corrected HPRT Gene Produced by Gene Targeting in Embryonic Stem Cells", *Cell*, 56:313-321 (1989).

Thotakura and Bahl, "Enzymatic Deglycosylation of Glycoproteins", *Meth. Enzymol.*, 138:350 (1987).

Tice et al., "Synergistic Induction of Tumor Antigens by Wnt-1 Signaling and Retinoid Acid Revealed by Gene Expression Profiling", *The Journal of Biological Chemistry*, US 277(16):14329-14335 (Apr. 2002).

Tilburn et al. "Transformation by Integration in *Aspergillus nidulans*", *Gene*. 26:205-221 (1983).

Traunecker et al., "Bispecific single chain molecules (Janusins) target cytotoxic lymphocytes on HIV infected cells", *EMBO J.*, 10:3655-3659 (1991).

Tremblay et al., "Retinoic Acid Stimulates the Expression of 11β-Hydroxysteroid Dehydrogenase Type 2 in Human Choriocarcinoma JEG-3 Cells", *Biol. Reprod.*, 60:541-545 (1999).

Tschumper et al., "Sequence of a yeast DNA fragment containing a chromosomal replicator and the TRP1 gene", *Gene*, 10:157(1980).

Tsukamoto et al., "Expression of the int-1 Gene in Transgenic Mice Is Associated with Mammary Gland Hyperplasia; and Adenocarcinomas in Male and Female Mice", *Cell*, 55:619-625 (1988).

Urlaub and Chasin, "Isolation of Chinese Hamster Cell Mutants Deficient in Dihydrofolate Reductase Activity", *Proc. Natl. Acad. Sci. USA*, 77:4216 (1980).

Van der Krol et al., "Modulation of Eukaryotic Gene Expression by Complementary RNA or DNA Sequences", *BioTechniques*, 6:958 (1988).

Van der Putten et al., "Efficient insertion of genes into the mouse germ line via retroviral vectors", *Proc. Natl. Acad. Sci. USA*, 82:6148-615 (1985).

Van Ooyen et al., "The nucleotide sequence of the human int-1 mammary oncogene; evolutionary conservation of coding and noncoding sequences", *EMBO J.*, 4:2905-2909 (1985).

Van Solingen et al., "Fusion of Yeast Spheroplaste", *J. Bact.*, 130:946 (1977).

Verhoeyen et al., "Reshaping Human Antibodies: Grafting an Antilysozyme Activity", *Science*, 239:1534-1536 (1988).

Vitetta et al., "Redesigning Nature's Poisons to Create Anti-Tumor Reagents", *Science*, 238: 1098 (1987).

Wade et al., "Regulation of the cholesterol efflux gene, ABCAI", *Lancet*, 357:161-163 (2001).

Wagner et al., "Transferrin-polycation conjugates as carriers for DNA uptake into cells", *Proc. Natl. Acad. Sci. USA*, 87:3410-3414 (1990).

Wainwright et al., "Isolation of a human gene with protein sequence similarity to human and murine int-1 and the *Drosophila* segment polarity mutant wingless", *EMBO J.*, 7:1743-1748 (1988).

Warzocha and Wotowiec, "Antisense strategy biological utility and prospects in the treatment of hematological malignancies", *Leuk. Lymphoma*, 24:267-281 (1997).

Wells et al., "Cassette mutagenesis: an efficient method for generation of multiple mutations at defined sites", *Gene*, 34:315 (1985).

Wells et al., "Importance of hydrogen-bond formation in stabilizing the transition state of subtilisin", *Philos. Trans. R. Soc. London SerA*, 317:415-423 (1986).

Willert et al. "Wnt-induced dephosphorylation of Axin releases-catenin from the Axin complex", *Genes Dev.*, 13:1768-73 (1999).

Wilman, Derry E., "Prodrugs in Cancer Chemotherapy", *Biochemical Society Transactions*, 14:375-382, 615th Meeting, Belfast (1986).

Wodarz et al., "Mechanisms of WNT Signaling in Development", *Annu. Rev. Cell. Dev. Biol.*, 14:59-88 (1998).

Wodicka et al., "Genome-wide expression monitoring in *Saccharomyces cerevisiae*", *Nat. Biotechnol.*, 15:1359-1367 (1997).

Wong et al., "Differential Transformation of Mammary Epithelial Cells by Wnt Genes", *Mol. Cell. Biol.*, 14:6278-6286 (1994).

Wright et al. "β-Catenin mutation and expression analysis on ovarian cancer: Excon 3 mutations and nuclear translocation in 16% of endometrioid tumours", *Int. J. Cancer*, 82:625-9 (1999).

Wu et al., "Receptor-mediated in Vitro Gene Transformation by a Soluble DNA Carrier System", *J. Biol. Chem.*, 262:4429-4432 (1987).

Xiang et al., "Expression of Co-stimulatory 4-1BB Ligand Induces Significant Tumor Regression and Protective Immunity", *Cancer Biotherapy and Radiopharmaceuticals*, 14(5):353-361 (1999).

Yamada at al., "Identification of semaphorin E as non-MDR drug resistance gene of human cancers", *Proc. Natl. Acad. Sci. USA*, 94:14713-14718 (1997).

Yelton et al., "Transformation of *Aspergillus nidulans* by using trpCplasmid", *Proc. Natl. Acad. Sci. USA*, 81: 1470-1474 (1984).

Zacharski, Leo R., "Basis for Selection of Anticoagulant Drugs for Therapeutic Trials in Human Malingnancy", *Haemostasis*, 16:300-320 (1986).

Zamecnik et al., "Inhibition of replication and expression of human T-cell lymphotropic virus type 1911 in cultured cells by exogenous synthetic oligonucleotides complementary to viral RNA", *Proc. Natl. Acad. Sci. USA*, 83:4143-4146 (1986).

Zapata et al., "Engineering linear F(ab')2 fragments for efficient production in *Escherichia coli* and enhanced antiproliferative activity", *Protein Eng.*, 8(10):1057-1062 (1995).

Zhang et al., "Gene Expression Profiles in Normal and Cancer Cells", *Science*, 276:1268-1272 (1997).

Zhang et al., "The Retinoic Acid and cAMP-dependent Up-regulation of 3-O-Sulfotransferase-1 Leads to a Dramatic Augmentation of Anticoagulantly Active Heparan Sulfate Biosynthesis in F9 Embryonal Carcinoma Cells", *J. Biol. Chem.*, 273:27998-28003 (1998).

Ziemer et al., "Identification of a Mouse Homolog of the Human BTEB2 Transcription Factor as a β-Catenin-Independent Wnt-1 Responsive Gene", *Mol. Cell. Biol.*, 21:562-574 (2001).

Zola, Heddy, *Monoclonal Antibodies: A Manual of Techniques*, CRC Press, Inc. (1987) pp. 147-158.

Zupi et al. "Cloning in Vitro and in Vivo of Lewis Lung Carcinoma: Properties and Characteristics", *Br. J. Cancer*, 41:suppl. 4:309 (1980).

* cited by examiner

AGTCCCAGACGGGCTTTTCCCAGAGAGCTAAAAGAGAAGGGCCAGAGAATGTCGTCCCAG
CCAGCAGGGAACCAGACCTCCCCCGGGGCCACAGAGGACTACTCCTATGGCAGCTGGTAC
ATCGATGAGCCCCAGGGGGGCGAGGAGCTCCAGCCAGAGGGGGAAGTGCCCTCCTGCCAC
ACCAGCATACCACCCGGCCTGTACCACGCCTGCCTGGCCTCGCTGTCAATCCTTGTGCTG
CTGCTCCTGGCCATGCTGGTGAGGCGCCGCCAGCTCTGGCCTGACTGTGTGCGTGGCAGG
CCCGGCCTGCCCAGCCCTGTGGATTTCTTGGCTGGGGACAGGCCCCGGGCAGTGCCTGCT
GCTGTTTTCATGGTCCTCCTGAGCTCCCTGTGTTTGCTGCTCCCGACGAGGACGCATTG
CCCTTCCTGACTCTCGCCTCAGCACCCAGCCAAGATGGGAAAACTGAGGCTCCAAGAGGG
GCCTGGAAGATACTGGGACTGTTCTATTATGCTGCCCTCTACTACCCTCTGGCTGCCTGT
GCCACGGCTGGCCACACAGCTGCACACCTGCTCGGCAGCACGCTGTCCTGGGCCCACCTT
GGGGTCCAGGTCTGGCAGAGGGCAGAGTGTCCCCAGGTGCCCAAGATCTACAAGTACTAC
TCCCTGCTGGCCTCCCTGCCTCTCCTGCTGGGCCTCGGATTCCTGAGCCTTTGGTACCCT
GTGCAGCTGGTGAGAAGCTTCAGCCGTAGGACAGGAGCAGGCTCCAAGGGGCTGCAGAGC
AGCTACTCTGAGGAATATCTGAGGAACCTCCTTTGCAGGAAGAAGCTGGGAAGCAGCTAC
CACACCTCCAAGCATGGCTTCCTGTCCTGGGCCCGCGTCTGCTTGAGACACTGCATCTAC
ACTCCACAGCCAGGATTCCATCTCCCGCTGAAGCTGGTGCTTTCAGCTACACTGACAGGG
ACGGCCATTTACCAGGTGGCCCTGCTGCTGCTGGTGGGCGTGGTACCCACTATCCAGAAG
GTGAGGGCAGGGGTCACCACGGATGTCTCCTACCTGCTGGCCGGCTTTGGAATCGTGCTC
TCCGAGGACAAGCAGGAGGTGGTGGAGCTGGTGAAGCACCATCTGTGGGCTCTGGAAGTG
TGCTACATCTCAGCCTTGGTCTTGTCCTGCTTACTCACCTTCCTGGTCCTGATGCGCTCA
CTGGTGACACACAGGACCAACCTTCGAGCTCTGCACCGAGGAGCTGCCCTGGACTTGAGT
CCCTTGCATCGGAGTCCCCATCCCTCCCGCCAAGCCATATTCTGTTGGATGAGCTTCAGT
GCCTACCAGACAGCCTTTATCTGCCTTGGGCTCCTGGTGCAGCAGATCATCTTCTTCCTG
GGAACCACGGCCCTGGCCTTCCTGGTGCTCATGCCTGTGCTCCATGGCAGGAACCTCCTG
CTCTTCCGTTCCCTGGAGTCCTCGTGGCCCTTCTGGCTGACTTTGGCCCTGGCTGTGATC
CTGCAGAACATGGCAGCCCATTGGGTCTTCCTGGAGACTCATGATGGACACCCACAGCTG
ACCAACCGGCGAGTGCTCTATGCAGCCACCTTTCTTCTCTTCCCCCTCAATGTGCTGGTG
GGTGCCATGGTGGCCACCTGGCGAGTGCTCCTCTCTGCCCTCTACAACGCCATCCACCTT
GGCCAGATGGACCTCAGCCTGCTGCCACCGAGAGCCGCCACTCTCGACCCCGGCTACTAC
ACGTACCGAAACTTCTTGAAGATTGAAGTCAGCCAGTCGCATCCAGCCATGACAGCCTTC
TGCTCCCTGCTCCTGCAAGCGCAGAGCCTCCTACCCAGGACCATGGCAGCCCCCCAGGAC
AGCCTCAGACCAGGGGAGGAAGACGAAGGGATGCAGCTGCTACAGACAAAGGACTCCATG
GCCAAGGGAGCTAGGCCCGGGGCCAGCCGCGGCAGGGCTCGCTGGGGTCTGGCCTACACG
CTGCTGCACAACCCAACCCTGCAGGTCTTCCGCAAGACGGCCCTGTTGGGTGCCAATGGT
GCCCAGCCCTGAGGGCAGGGAAGGTCAACCCACCTGCCCATCTGTGCTGAGGCATGTTCC
TGCCTACCATCCTCCTCCCTCCCCGGCTCTCCTCCCAGCATCACACCAGCCATGCAGCCA
GCAGGTCCTCCGGATCACTGTGGTTGGGTGGAGGTCTGTCTGCACTGGGAGCCTCAGGAG
GGCTCTGCTCCACCCACTTGGCTATGGGAGAGCCAGCAGGGGTTCTGGAGAAAAAACTG
GTGGGTTAGGGCCTTGGTCCAGGAGCCAGTTGAGCCAGGGCAGCCACATCCAGGCGTCTC
CCTACCCTGGCTCTGCCATCAGCCTTGAAGGCCTCGATGAAGCCTTCTCTGGAACCACT
CCAGCCCAGCTCCACCTCAGCCTTGGCCTTCACGCTGTGGAAGCAGCCAAGGCACTTCCT
CACCCCCTCAGCGCCACGGACCTCTCTGGGGAGTGGCCGGAAAGCTCCCGGTCCTCTGGC
CTGCAGGGCAGCCCAAGTCATGACTCAGACCAGGTCCCACACTGAGCTGCCCACACTCGA
GAGCCAGATATTTTTGTAGTTTTTATGCCTTTGGCTATTATGAAAGAGGTTAGTGTGTTC
CCTGCAATAAACTTGTTCCTGAGAAAAAAAAAAAAAAAAAAAAAAAAAAAAAAAAAAAAA
AAAAAAAAAAAAAAAAAAAAAAAAAAAAAAA

*FIG._1*

MSSQPAGNQTSPGATEDYSYGSWYIDEPQGGEELQPEGEVPSCHTSIPPGLYHACLASLS
ILVLLLLAMLVRRRQLWPDCVRGRPGLPSPVDFLAGDRPRAVPAAVFMVLLSSLCLLLPD
EDALPFLTLASAPSQDGKTEAPRGAWKILGLFYYAALYYPLAACATAGHTAAHLLGSTLS
WAHLGVQVWQRAECPQVPKIYKYYSLLASLPLLLGLGFLSWYPVQLVRSFSRRTGAGSK
GLQSSYSEEYLRNLLCRKKLGSSYHTSKHGFLSWARVCLRHCIYTPQPGFHLPLKLVLSA
TLTGTAIYQVALLLLVGVVPTIQKVRAGVTTDVSYLLAGFGIVLSEDKQEVVELVKHHLW
ALEVCYISALVLSCLLTFLVLMRSLVTHRTNLRALHRGAALDLSPLHRSPHPSRQAIFCW
MSFSAYQTAFICLGLLVQQIIFFLGTTALAFLVLMPVLHGRNLLLFRSLESSWPFWLTLA
LAVILQNMAAHWVFLETHDGHPQLTNRRVLYAATFLLFPLNVLVGAMVATWRVLLSALYN
AIHLGQMDLSLLPPRAATLDPGYYTYRNFLKIEVSQSHPAMTAFCSLLLQAQSLLPRTMA
APQDSLRPGEEDEGMQLLQTKDSMAKGARPGASRGRARWGLAYTLLHNPTLQVFRKTALL
GANGAQP

Important features of the protein:

Signal peptide:

None

Transmembrane domain:

54-69
102-119
148-166
207-222
301-320
364-380
431-451
474-489
560-535

Motif file:
Motif name: N-glycosylation site.

8-12

Motif name: N-myristoylation site.

50-56
   176-182
   241-247
   317-323
   341-347
   525-531
   627-633
   631-637
   640-646
   661-667

Motif name: Prokaryotic membrane lipoprotein lipid attachment site.

364-375

Motif name: ATP/GTP-binding site motif A (P-loop).

PRO                    XXXXXXXXXXXXXXX    (Length = 15 amino acids)
Comparison Protein     XXXXXYYYYYYY       (Length = 12 amino acids)
% amino acid sequence identity =
(the number of identically matching amino acid residues between the two polypeptide
sequences as determined by ALIGN-2) divided by (the total number of amino acid residues
of the PRO polypeptide) =
5 divided by 15 = 33.3%

FIG._3A

PRO                    XXXXXXXXXX         (Length = 10 amino acids)
Comparison Protein     XXXXXYYYYYYZZYZ    (Length = 15 amino acids)
% amino acid sequence identity =
(the number of identically matching amino acid residues between the two polypeptide
sequences as determined by ALIGN-2) divided by (the total number of amino acid residues
of the PRO polypeptide) =
5 divided by 10 = 50%

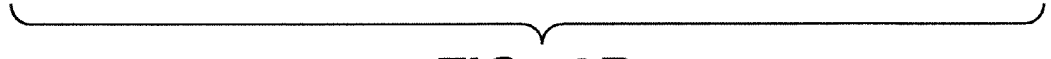

FIG._3B

PRO-DNA                NNNNNNNNNNNNNN     (Length = 14 nucleotides)
Comparison DNA         NNNNNNLLLLLLLLLL   (Length = 16 nucleotides)
% nucleic acid sequence identity =
(the number of identically matching nucleotides between the two nucleic acid sequences
as determined by ALIGN-2) divided by (the total number of nucleotides of the PRO-DNA
nucleic acid sequence) =
6 divided by 14 = 42.9%

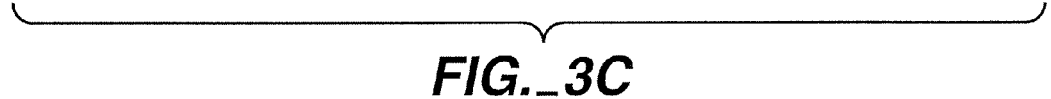

FIG._3C

PRO-DNA                NNNNNNNNNNNN       (Length = 12 nucleotides)
Comparison DNA         NNNNLLLVV          (Length = 9 nucleotides)
% nucleic acid sequence identity =
(the number of identically matching nucleotides between the two nucleic acid sequences
as determined by ALIGN-2) divided by (the total number of nucleotides of the PRO-DNA
nucleic acid sequence) =
4 divided by 12 = 33.3%

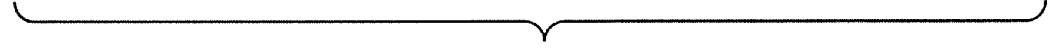

```
/*
 *
 * C-C increased from 12 to 15
 * Z is average of EQ
 * B is average of ND
 * match with stop is _M; stop-stop = 0; J (joker) match = 0
 */
#define _M  -8    /* value of a match with a stop */
int     _day[26][26] = {
/*     A  B  C  D  E  F  G  H  I  J  K  L  M  N  O  P  Q  R  S  T  U  V  W  X  Y  Z*/
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M,0,_M,_M,_M,_M,
         _M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4,-1,-2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

FIG._4B

```
/*
*/
#include <stdio.h>
include <ctype.h> define   MAXJMP   16     /* max jumps in a diag */
define   MAXGAP   24     /* don't continue to penalize gaps larger than this */
#define   JMPS     1024   /* max jmps in an path */
define   MX       4      /* save if there's at least MX-1 bases since last jmp */ define   DMAT     3      /* value of matching bases */
define   DMIS     0      /* penalty for mismatched bases */
#define   DINS0    8      /* penalty for a gap */
#define   DINS1    1      /* penalty per base */
#define   PINS0    8      /* penalty for a gap */
define   PINS1    4      /* penalty per residue */ struct jmp {
          short            n[MAXJMP];       /* size of jmp (neg for dely) */
          unsigned short   x[MAXJMP];       /* base no. of jmp in seq x */
};                                          /* limits seq to 2^16 -1 */ struct diag {
          int       score;     /* score at last jmp */
          long      offset;    /* offset of prev block */
          short     ijmp;      /* current jmp index */
          struct    jmpjp;     /* list of jmps */
};

struct path {
          int       spc;       /* number of leading spaces */
          short     n[JMPS];   /* size of jmp (gap) */
          int       x[JMPS];   /* loc of jmp (last elem before gap) */
};

char          *ofile;           /* output file name */
char          *namex[2];        /* seq names: getseqs() */
char          *prog;            /* prog name for err msgs */
char          *seqx[2];         /* seqs: getseqs() */
int           dmax;             /* best diag: nw() */
int           dmax0;            /* final diag */
int           dna;              /* set if dna: main() */
int           endgaps;          /* set if penalizing end gaps */
int           gapx, gapy;       /* total gaps in seqs */
int           len0, len1;       /* seq lens */
int           ngapx, ngapy;     /* total size of gaps */
int           smax;             /* max score: nw() */
int           *xbm;             /* bitmap for matching */
long          offset;           /* current offset in jmp file */
struct diag   *dx;              /* holds diagonals */
struct path   pp[2];            /* holds path for seqs */ char          *calloc(), *malloc(), *index(), *strcpy();
char          *getseq(), *g_calloc();
```

Page 1 of nw.h

FIG._4C

```
/* Needleman-Wunsch alignment program
 *
 * usage: progs file1 file2
 *  where file1 and file2 are two dna or two protein sequences.
 *  The sequences can be in upper- or lower-case an may contain ambiguity
 *  Any lines beginning with ';', '>' or '<' are ignored
 *  Max file length is 65535 (limited by unsigned short x in the jmp struct)
 *  A sequence with 1/3 or more of its elements ACGTU is assumed to be DNA
 *  Output is in the file "align.out"
 *
 * The program may create a tmp file in /tmp to hold info about traceback.
 * Original version developed under BSD 4.3 on a vax 8650
 */
include "nw.h"
#include "day.h"

static _dbval[26] = {
        1,14,2,13,0,0,4,11,0,0,12,0,3,15,0,0,0,5,6,8,8,7,9,0,10,0
};

static _pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};

main(ac, av)                                                              main
        int     ac;
        char    *av[];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;

endgaps = 0;            /* 1 to penalize endgaps */
        ofile = "align.out";    /* output file */ nw();           /* fill in the matrix, get the possible jmps */
        readjmps();     /* get the actual jmps */
        print();        /* print stats, alignment */ cleanup(0);     /* unlink any tmp files */
}
```

FIG._4D

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                        nw
{
        char        *px, *py;           /* seqs and ptrs */
        int         *ndely, *dely;      /* keep track of dely */
        int         ndelx, delx;        /* keep track of delx */
        int         *tmp;               /* for swapping row0, row1 */
        int         mis;                /* score for each type */
        int         ins0, ins1;         /* insertion penalties */
        register    id;                 /* diagonal index */
        register    ij;                 /* jmp index */
        register    *col0, *col1;       /* score for curr, last row */
        register    xx, yy;             /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely",  len1+1, sizeof(int));
        col0  = (int *)g_calloc("to get col0",  len1+1, sizeof(int));
        col1  = (int *)g_calloc("to get col1",  len1+1, sizeof(int));
        ins0 = (dna)? DINS0 : PINS0;
        ins1 = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;   /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

```
            id = xx - yy + len1 - 1;
            if (mis >= delx && mis >= dely[yy])
                    col1[yy] = mis;
            else if (delx >= dely[yy]) {
                    col1[yy] = delx;
                    ij = dx[id].ijmp;
                    if (dx[id].jp.n[0] && (!dna || (ndelx >= MAXJMP
                            && xx > dx[id].jp.x[ij]+MX) || mis > dx[id].score+DINS0)) {
                            dx[id].ijmp++;
                            if (++ij >= MAXJMP) {
                                    writejmps(id);
                                    ij = dx[id].ijmp = 0;
                                    dx[id].offset = offset;
                                    offset += sizeof(struct jmp) + sizeof(offset);
                            }
                    }
                    dx[id].jp.n[ij] = ndelx;
                    dx[id].jp.x[ij] = xx;
                    dx[id].score = delx;
            }
            else {
                    col1[yy] = dely[yy];
                    ij = dx[id].ijmp;

if (dx[id].jp.n[0] && (!dna || (ndely[yy] >= MAXJMP
            && xx > dx[id].jp.x[ij]+MX) || mis > dx[id].score+DINS0)) {
                            dx[id].ijmp++;
                            if (++ij >= MAXJMP) {
                                    writejmps(id);
                                    ij = dx[id].ijmp = 0;
                                    dx[id].offset = offset;
                                    offset += sizeof(struct jmp) + sizeof(offset);
                            }
                    }
                    dx[id].jp.n[ij] = -ndely[yy];
                    dx[id].jp.x[ij] = xx;
                    dx[id].score = dely[yy];
            }
            if (xx == len0 && yy < len1) {
                    /* last col
                     */
                    if (endgaps)
                            col1[yy] -= ins0+ins1*(len1-yy);
                    if (col1[yy] > smax) {
                            smax = col1[yy];
                            dmax = id;
```

*FIG._4F-1*

```
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;
    }
    (void) free((char *)ndely);
    (void) free((char *)dely);
    (void) free((char *)col0);
    (void) free((char *)col1);
}
```

```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */ include "nw.h"

define SPC        3
#define P_LINE     256     /* maximum output line */
define P_SPC      3       /* space between name or num and seq */ extern    _day[26][26];
int       olen;            /* set output line length */
FILE      *fx;             /* output file */ print()                                                              print
{
        int    lx, ly, firstgap, lastgap;      /* overlap */ if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {        /* leading gap in x */
                pp[0].spc = firstgap = len1 - dmax - 1;
                ly -= pp[0].spc;
        }
        else if (dmax > len1 - 1) {   /* leading gap in y */
                pp[1].spc = firstgap = dmax - (len1 - 1);
                lx -= pp[1].spc;
        }
        if (dmax0 < len0 - 1) {       /* trailing gap in x */
                lastgap = len0 - dmax0 -1;
                lx -= lastgap;
        }
        else if (dmax0 > len0 - 1) {  /* trailing gap in y */
                lastgap = dmax0 - (len0 - 1);
                ly -= lastgap;
        }
        getmat(lx, ly, firstgap, lastgap);
        pr_align();
}
```

FIG._4H

```
/*
 * trace back the best path, count matches
 */
static
getmat(lx, ly, firstgap, lastgap)                                              getmat
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         *  if penalizing endgaps, base is the shorter seq
         *  else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
```

Page 2 of nwprint.c

```
            fprintf(fx, "<gaps in first sequence: %d", gapx);                    ...getmat
            if (gapx) {
                    (void) sprintf(outx, " (%d %s%s)",
                            ngapx, (dna)? "base":"residue", (ngapx == 1)? "":"s");
                    fprintf(fx,"%s", outx);

fprintf(fx, ", gaps in second sequence: %d", gapy);
            if (gapy) {
                    (void) sprintf(outx, " (%d %s%s)",
                            ngapy, (dna)? "base":"residue", (ngapy == 1)? "":"s");
                    fprintf(fx,"%s", outx);
            }
            if (dna)
                    fprintf(fx,
                        "\n<score: %d (match = %d, mismatch = %d, gap penalty = %d + %d per
                        base)\n", smax, DMAT, DMIS, DINS0, DINS1);
            else
                    fprintf(fx,
                        "\n<score: %d (Dayhoff PAM 250 matrix, gap penalty = %d + %d per
                        residue)\n", smax, PINS0, PINS1);
            if (endgaps)
                    fprintf(fx,
                        "<endgaps penalized. left endgap: %d %s%s, right endgap: %d %s%s\n",
                        firstgap, (dna)? "base" : "residue", (firstgap == 1)? "" : "s",
                        lastgap, (dna)? "base" : "residue", (lastgap == 1)? "" : "s");
            else
                    fprintf(fx, "<endgaps not penalized\n");
    }
    static         nm;                    /* matches in core -- for checking */
    static         lmax;                  /* lengths of stripped file names */
    static         ij[2];                 /* jmp index for a path */
    static         nc[2];                 /* number at start of current line */
    static         ni[2];                 /* current elem number -- for gapping */
    static         siz[2];
    static char    *ps[2];                /* ptr to current element */
    static char    *po[2];                /* ptr to next output char slot */
    static char    out[2][P_LINE];        /* output line */
    static char    star[P_LINE];          /* set by stars() */
    /*
     * print alignment of described in struct path pp[]
     */
    static
    pr_align()                                                                   pr_align
```

FIG._4I-1

```
{
    int         nn;    /* char count */
    int         more;
    register    i;

for (i = 0, lmax = 0; i < 2; i++) {
        nn = stripname(namex[i]);
        if (nn > lmax)
            lmax = nn;
        nc[i] = 1;
        ni[i] = 1;
        siz[i] = ij[i] = 0;
        ps[i] = seqx[i];
        po[i] = out[i];
```

FIG._4I-2

```
                for (nn = nm = 0, more = 1; more; ) {                                    ...pr_align
                    for (i = more = 0; i < 2; i++) {
                        /*
                         * do we have more of this sequence?
                         */
                        if (!*ps[i])
                            continue;
                        more++;
                        if (pp[i].spc) {         /* leading space */
                            *po[i]++ = ' ';
                            pp[i].spc--;
                        }
                        else if (siz[i]) {       /* in a gap */
                            *po[i]++ = '-';
                            siz[i]--;
                        }
                        else {        /* we're putting a seq element
                                       */
                            *po[i] = *ps[i];
                            if (islower(*ps[i]))
                                *ps[i] = toupper(*ps[i]);
                            po[i]++;
                            ps[i]++;

/*
                             * are we at next gap for this seq?
                             */
                            if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                    siz[i] += pp[i].n[ij[i]++];
                            }
                            ni[i]++;
                        }
                    }
                    if (++nn == olen || !more && nn) {
                        dumpblock();
                        for (i = 0; i < 2; i++)
                            po[i] = out[i];
                        nn = 0;
                    }
                }
            }
            /*
             * dump a block of lines, including numbers, stars: pr_align()
             */
            static
            dumpblock()                                                                  dumpblock
            {
                register    i;

for (i = 0; i < 2; i++)
                    *po[i]-- = '\0';
```

FIG._4J

```
                (void) putc('\n', fx);
                for (i = 0; i < 2; i++) {
                        if (*out[i] && (*out[i] != ' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star);
                                if (i == 1)
                                        nums(i);
                        }
                }
}
/*
 * put out a number line: dumpblock()                                                       ...dumpblock
 */
static
nums(ix)
        int     ix;     /* index in out[] holding seq line */                               nums
{
        char            nline[P_LINE];
        register        i, j;
        register char   *pn, *px, *py;
        for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}
/*
 * put out a line (name, [num], seq, [num]): dumpblock()
 */
static
putline(ix)                                                                                 putline
        int     ix;
{
```

FIG._4K

```
                                                                              ...putline
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}
/*
 * put a line of stars (seqs always in out[0], out[1]): dumpblock()
 */
static
stars()                                                                       stars
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

FIG._4L

```
/*
 * strip path or prefix from pn, return len: pr_align()
 */
static
stripname(pn)
        char    *pn;    /* file name (may be path) */
{
        register char      *px, *py;

py = 0;
        for (px = pn; *px; px++)
                if (*px == '/')
                        py = px + 1;
        if (py)
                (void) strcpy(pn, py);
        return(strlen(pn));

}
``` stripname

FIG._4M

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char    *jname = "/tmp/homgXXXXXX";       /* tmp file for jmps */
FILE    *fj;
int     cleanup();                         /* cleanup tmp file */
long    lseek();
/*
 * remove any tmp file if we blow
 */
cleanup(i)                                                                      cleanup
        int     i;
{
        if (fj)
                (void) unlink(jname);
        exit(i);
}
/*
 * read, return ptr to seq, set dna, len, maxlen
 * skip lines starting with ';', '<', or '>'
 * seq in upper or lower case
 */
char    *
getseq(file, len)                                                               getseq
        char            *file;   /* file name */
        int             *len;    /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

FIG._4N

Page 1 of nwsubr.c

```
                py = pseq + 4;
                *len = tlen;
                rewind(fp);

while (fgets(line, 1024, fp)) {
                        if (*line == ';' || *line == '<' || *line == '>')
                                continue;
                        for (px = line; *px != '\n'; px++) {
                                if (isupper(*px))
                                        *py++ = *px;
                                else if (islower(*px))
                                        *py++ = toupper(*px);
                                if (index("ATGCU",*(py-1)))
                                        natgc++;
                        }
                }
                *py++ = '\0';
                *py = '\0';
                (void) fclose(fp);
                dna = natgc > (tlen/3);
                return(pseq+4);
}
char    *
g_calloc(msg, nx, sz)                                                                   g_calloc
        char    *msg;           /* program, calling routine */
        int     nx, sz;         /* number and size of elements */
{
        char            *px, *calloc();

if ((px = calloc((unsigned)nx, (unsigned)sz)) == 0) {
                if (*msg) {
                        fprintf(stderr, "%s: g_calloc() failed %s (n=%d, sz=%d)\n", prog, msg,
                         nx, sz);
                        exit(1);
                }
        }
        return(px);
}

/*
* get final jmps from dx[] or tmp file, set pp[], reset dmax: main()
*/
readjmps()                                                                              readjmps
{
        int             fd = -1;
        int             siz, i0, i1;
        register        i, j, xx;

if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
```

FIG._40

```
                                                              ...readjmps
        if (j < 0 && dx[dmax].offset && fj) {
                (void) lseek(fd, dx[dmax].offset, 0);
                (void) read(fd, (char *)&dx[dmax].jp, sizeof(struct jmp));
                (void) read(fd, (char *)&dx[dmax].offset,
                        sizeof(dx[dmax].offset));
                dx[dmax].ijmp = MAXJMP-1;
        }
        else
                break;
}
if (i >= JMPS) {
        fprintf(stderr, "%s: too many gaps in alignment\n", prog);
        cleanup(1);
}
if (j >= 0) {
        siz = dx[dmax].jp.n[j];
        xx = dx[dmax].jp.x[j];
        dmax += siz;
        if (siz < 0) {         /* gap in second seq */
                pp[1].n[i1] = -siz;
                xx += siz;
                /* id = xx - yy + len1 - 1
                 */
                pp[1].x[i1] = xx - dmax + len1 - 1;
                gapy++;
                ngapy -= siz;
/* ignore MAXGAP when doing endgaps */
                siz = (-siz < MAXGAP || endgaps)? -siz : MAXGAP;
                i1++;
        }
        else if (siz > 0) {    /* gap in first seq */
                pp[0].n[i0] = siz;
                pp[0].x[i0] = xx;
                gapx++;
                ngapx += siz;
/* ignore MAXGAP when doing endgaps */
                siz = (siz < MAXGAP || endgaps)? siz : MAXGAP;
                i0++;
        }
}
else
        break;
}
```

FIG._4P-1

```
/* reverse the order of jmps
 */
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}}
```

FIG._4P-2

```
/*
 * write a filled jmp struct offset of the prev one (if any): nw()
 */
writejmps(ix)                                                           writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

FIG._4Q

```
GTGCTCTCCGAGGACAAGCAGGAGGNGGTGGAGCTGGTGAAGCACCATCTGTGGGCTCTG
GAAGTGTGCTACATCTCAGCCTTGGTCTTGTCCTGCTTACTCACCTTCCTGGTCCTGATG
CGCTCACTGGTGACACACAGGACCAACCTTCGAGCTCTGCACCGAGGAGCTGCCCTGGAC
TTGAGTCCCTTGCATCGGAGTCCCCATCCCTCCCGCCAAGCCATATTCTGTTGGATGAGC
TTCAGTGCCTACCAGACAGCCTTTATCTGCCTTGGGCTCCTGGTGCAGCAGATCATCTTC
TTCCTGGGAACCACGGCCCTGGCCTTCCTGGTGCTCATGCCTGTGCTCCATGGCAGGAAC
CTCCTGCTCTTCCGTTCCCTGGAGTCCTCGTGGCCCTTCTGGCTGACTTTGGCCCTGGCT
GTGATCCTGCAGAACATGGCAGCCCATTGGGTCTTCCTGGAGACTCATGATGGACACCCA
CAGCTGACCAACCGGCGAGTGCTCTATGCAGCCACCTTTCTTCTCTTCCCCCTCAATGTG
CTGGTGGGTGCCATGGTGGCCACCTGGCGAGTGCTCCTCTCTGCCCTCTACAACGCCATC
CACCTTGGCCAGATGGACCTCAGCCTGCTGCCACCGAGAGCCGCCACTCTCGACCCCGGC
TACTACACGTACCGAA
```

FIG._5

```
CACAACCAGCCACCCCTCTAGGATCCCAGCCCAGCTGGTGCTGGGCTCAGAGGAGAAGGC
CCCGTGTTGGGAGCACCCTGCTTGCCTGGAGGGACAAGTTTCCGGGAGAGATCAATAAAG
GAAAGGAAAGAGACAAGGAAGGGAGAGGTCAGGAGAGCGCTTGATTGGAGGAGAAGGGCC
AGAGAATGTCGTCCCAGCCAGCAGGGAACCAGACCTCCCCCGGGGCCACAGAGGACTACT
CCTATGGCAGCTGGTACATCGATGAGCCCCAGGGGGGCGAGGAGCTCCAGCCAGAGGGGG
AAGTGCCCTCCTGCCACACCAGCATACCACCCGGCCTGTACCACGCCTGCCTGGCCTCGC
TGTCAATCCTTGTGCTGCTGCTCCTGGCCATGCTGGTGAGGCGCCGCCAGCTCTGGCCTG
ACTGTGTGCGTGGCAGGCCCGGCCTGCCCAGGCCCCGGGCAGTGCCTGCTGCTGTTTTCA
TGGTCCTCCTGAGCTCCCTGTGTTTGCTGCTCCCCGACGAGGACGCATTGCCCTTCCTGA
CTCTCGCCTCAGCACCCAGCCAAGATGGGAAAACTGAGGCTCCAAGAGGGGCCTGGAAGA
TACTGGGACTGTTCTATTATGCTGCCCTCTACTACCCTCTGGCTGCCTGTGCCACGGCTG
GCCACACAGCTGCACACCTGCTCGGCAGCACGCTGTCCTGGGCCCACCTTGGGGTCCAGG
TCTGGCAGAGGGCAGAGTGTCCCCAGGTGCCCAAGATCTACAAGTACTACTCCCTGCTGG
CCTCCCTGCCTCTCCTGCTGGGCCTCGGATTCCTGAGCCTTTGGTACCCTGTGCAGCTGG
TGAGAAGCTTCAGCCGTAGGACAGGAGCAGGCTCCAAGGGGCTGCAGAGCAGCTACTCTG
AGGAATATCTGAGGAACCTCCTTTGCAGGAAGAAGCTGGGAAGCAGCTACCACACCTCCA
AGCATGGCTTCCTGTCCTGGGCCCGCGTCTGCTTGAGACACTGCATCTACACTCCACAGC
CAGGATTCCATCTCCCGCTGAAGCTGGTGCTTTCAGCTACACTGACAGGGACGGCCATTT
ACCAGGTGGCCCTGCTGCTGCTGGTGGGCGTGGTACCCACTATCCAGAAGGTGAGGGCAG
GGGTCACCACGGATGTCTCCTACCTGCTGGCCGGCTTTGGAATCGTGCTCTCCGAGGACA
AGCAGGAGGTGGTGGAGCTGGTGAAGCACCATCTGTGGGCTCTGGAAGTGTGCTACATCT
CAGCCTTGGTCTTGTCCTGCTTACTCACCTTCCTGGTCCTGATGCGCTCACTGGTGACAC
ACAGGACCAACCTTCGAGCTCTGCACCGAGGAGCTGCCCTGGACTTGAGTCCCTTGCATC
GGAGTCCCCATCCCTCCCGCCAAGCCATATTCTGTTGGATGAGCTTCAGTGCCTACCAGA
CAGCCTTTATCTGCCTTGGGCTCCTGGTGCAGCAGATCATCTTCTTCCTGGGAACCACGG
CCCTGGCCTTCCTGGTGCTCATGCCTGTGCTCCATGGCAGGAACCTCCTGCTCTTCCGTT
CCCTGGAGTCCTCGTGGCCCTTCTGCTGACTTTGGCCCTGCTGTGATCCTGCAGAACA
TGGCAGCCCATTGGGTCTTCCTGGAGACTCATGATGGACACCCACAGCTGACCAACCGGC
GAGTGCTCTATGCAGCCACCTTTCTTCTCTTCCCCCTCAATGTGCTGGTGGGTGCCATAG
TGGCCACCTGGCGAGTGCTCCTCTCTGCCCTCTACAACGCCATCCACCTTGGCCAGATGG
ACCTCAGCCTGCTGCCACCGAGAGCCGCCACTCTCGACCCCGGCTACTACACGTACCGAA
ACTTCTTGAAGATTGAAGTCAGCCAGTCGCATCCAGCCATGACAGCCTTCTGCTCCCTGC
TCCTGCAAGCGCAGAGCCTCCTACCCAGGACCATGGCAGCCCCCAGGACAGCCTCAGAC
CAGGGGAGGAAGACGAAGGGATGCAGCTGCTACAGACAAAGGACTCCATGGCCAAGGGAG
CTAGGCCCGGGGCCAGCCGCGGCAGGGCTCGCTGGGGTCTGGCCTACACGCTGCTGCACA
ACCCAACCCTGCAGGTCTTCCGCAAGACGGCCCTGTTGGGTGCCAATGGTGCCCAGCCCT
GAGGGCAGGGAAGGTCAACCCACCTGCCCATCTGTGCTGAGGCATGTTCCTGCCTACCAC
CTCCTCCCTCCCCGGCTCTCCTCCCAGCATCACACCAGCCATGCAGCCAGCAGGTCCTCC
GGATCACTGTGGTTGGGTGGAGGTCTGTCTGCACTGGGAGCCTCAGGAGGGCTCTGCTCC
ACCCACTTGGCTATGGGAGAGCCAGCAGGGGTTCTGGAGAAAGAAACTGGTGGGTTAGGG
CCTTGGTCCAGGAGCCAGTTGAGCCAGGGCAGCCACATCCAGGCGTCTCCCTACCCTGGC
TCTGCCATCAGCCTTGAAGGGCCTCGATGAAGCCTTCTCTGGAACCACTCCAGCCCAGCT
CCACCTCAGCCTTGGCCTTCACGCTGTGGAAGCAGCCAAGGCACTTCCTCACCCCCTCAG
CGCCACGGACCTCTCTGGGGAGTGGCCGGAAAGCTCCCGGGCCTCTGGCCTGCAGGGCAG
CCCAAGTCATGACTCAGACCAGGTCCCACACTGAGCTGCCCACACTCGAGAGCCAGATAT
TTTTGTAGTTTTTATGCCTTTGGCTATTATGAAAGAGGTTAGTGTGTTCCCTGCAATAAA
CTTGTTCCTGAGAAAAA
```

FIG._6

MSSQPAGNQTSPGATEDYSYGSWYIDEPQGGEELQPEGEVPSCHTSIPPGLYHACLASL
SILVLLLLAMLVRRRQLWPDCVRGRPGLPRPRAVPAAVFMVLLSSLCLLLPDEDALPFL
TLASAPSQDGKTEAPRGAWKILGLFYYAALYYPLAACATAGHTAAHLLGSTLSWAHLGV
QVWQRAECPQVPKIYKYYSLLASLPLLLGLGFLSLWYPVQLVRSFSRRTGAGSKGLQSS
YSEEYLRNLLCRKKLGSSYHTSKHGFLSWARVCLRHCIYTPQPGFHLPLKLVLSATLTG
TAIYQVALLLLVGVVPTIQKVRAGVTTDVSYLLAGFGIVLSEDKQEVVELVKHHLWALE
VCYISALVLSCLLTFLVLMRSLVTHRTNLRALHRGAALDLSPLHRSPHPSRQAIFCWMS
FSAYQTAFICLGLLVQQIIFFLGTTALAFLVLMPVLHGRNLLLFRSLESSWPFWLTLAL
AVILQNMAAHWVFLETHDGHPQLTNRRVLYAATFLLFPLNVLVGAIVATWRVLLSALYN
AIHLGQMDLSLLPPRAATLDPGYYTYRNFLKIEVSQSHPAMTAFCSLLLQAQSLLPRTM
AAPQDSLRPGEEDEGMQLLQTKDSMAKGARPGASRGRARWGLAYTLLHNPTLQVFRKTA
LLGANGAQP

Important features of the protein:

Signal peptide:

none

Transmembrane domain:

54-71
93-111
140-157
197-214
291-312
356-371
425-444
464-481
505-522

Motif name: N-glycosylation site.

8-12

Motif name: N-myristoylation site.

50-56
    167-173
    232-238
    308-314
    332-338
    516-522
    618-624
    622-628
    631-637
    652-658

Motif name: Prokaryotic membrane lipoprotein lipid attachment site.

355-366

Motif name: ATP/GTP-binding site motif A (P-loop).

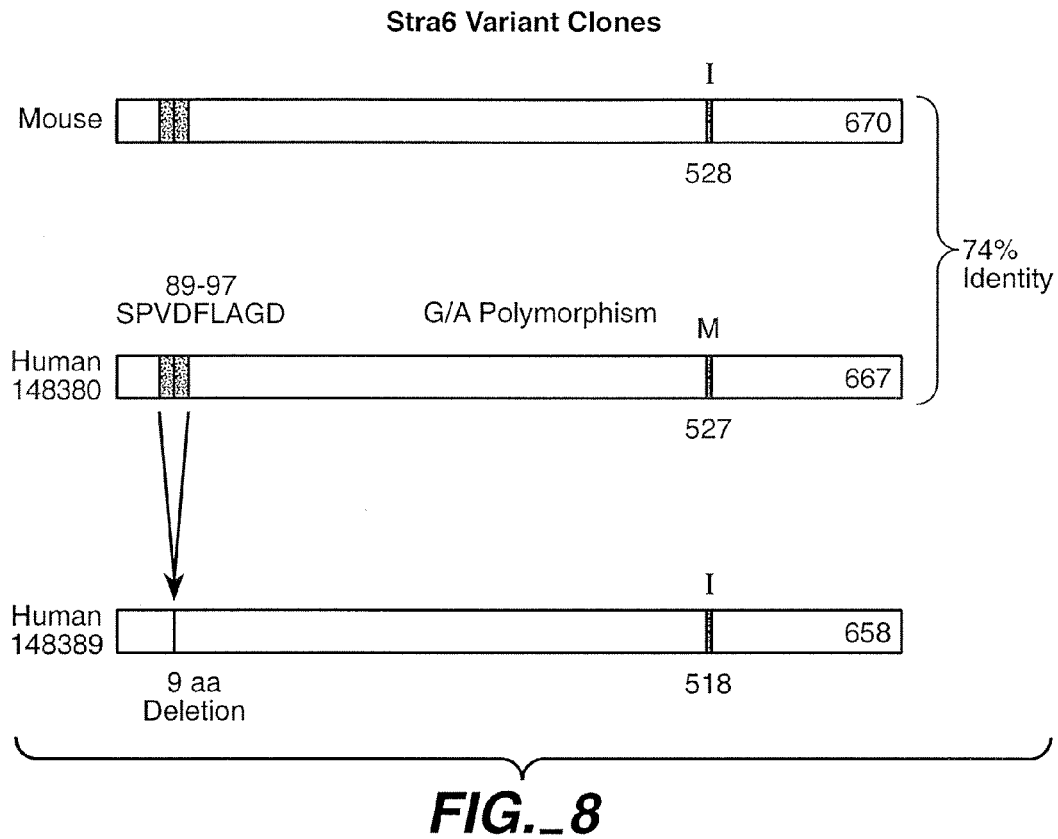
FIG._8
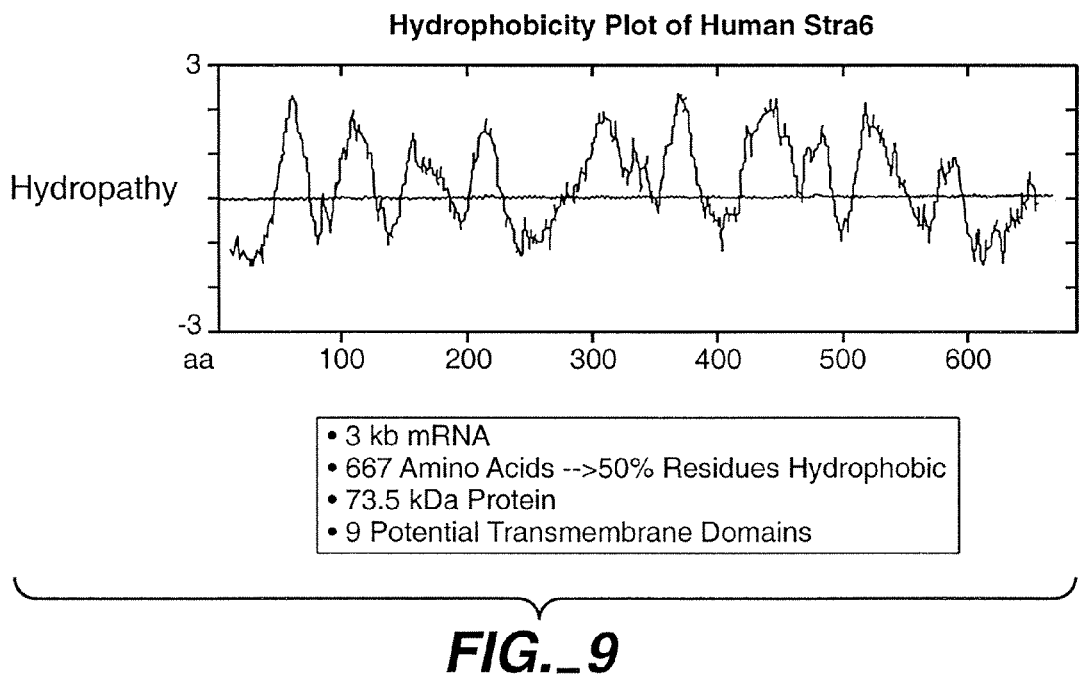
FIG._9

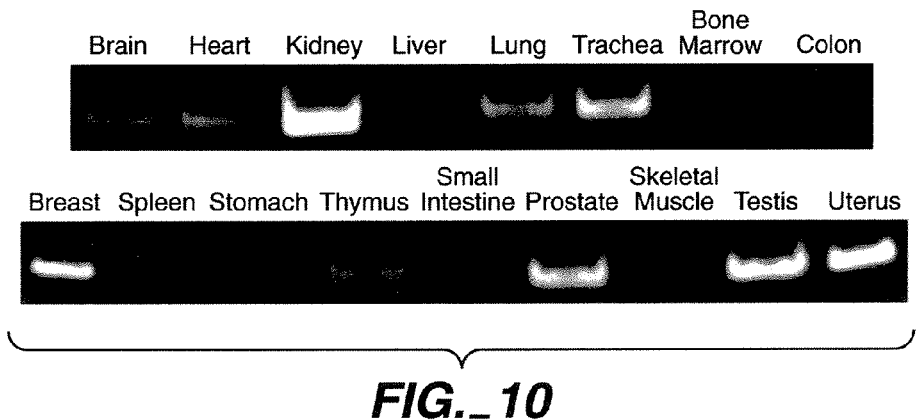
FIG._10
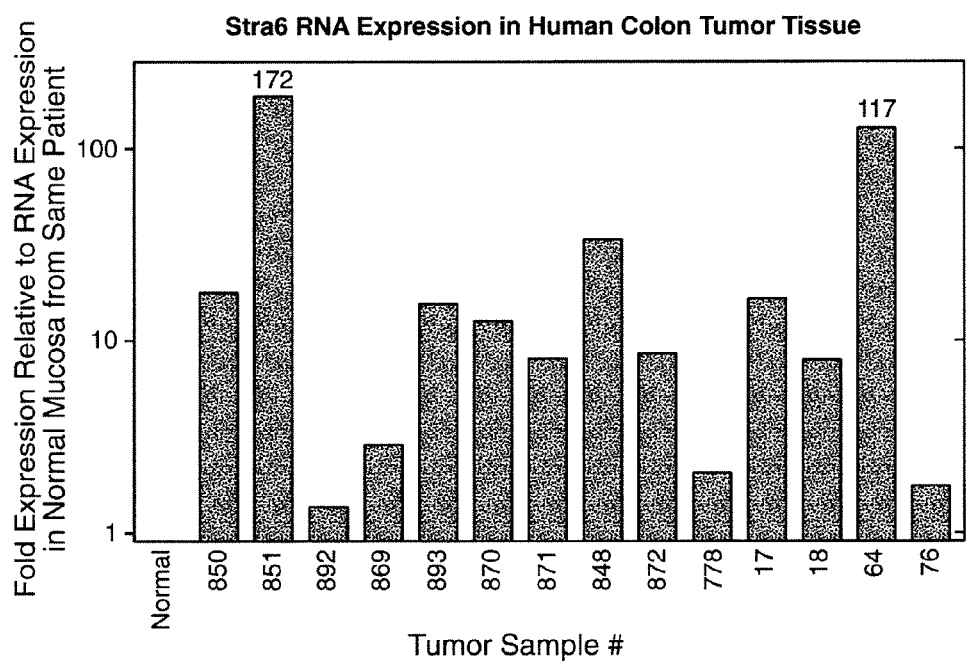
FIG._11

**Stra6 RNA Expression in Human Colon Tumor Tissue
vs Normal Mucosa From the Same Patient**
Taqman Product Analysis After 40 Cycles
*FIG._12A*
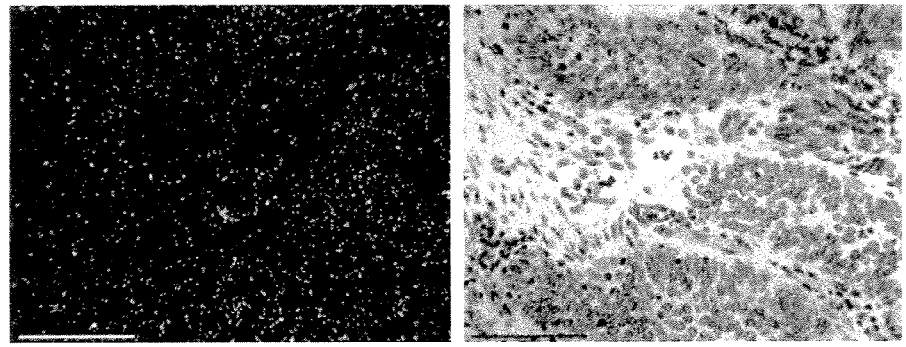
*FIG._12B*

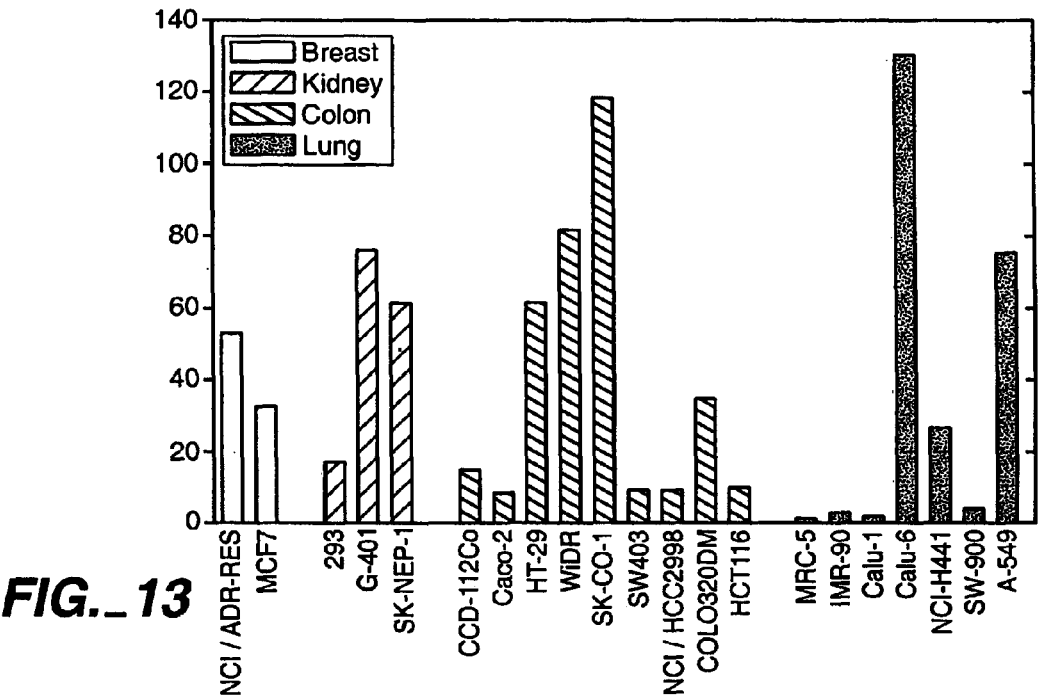
FIG._13
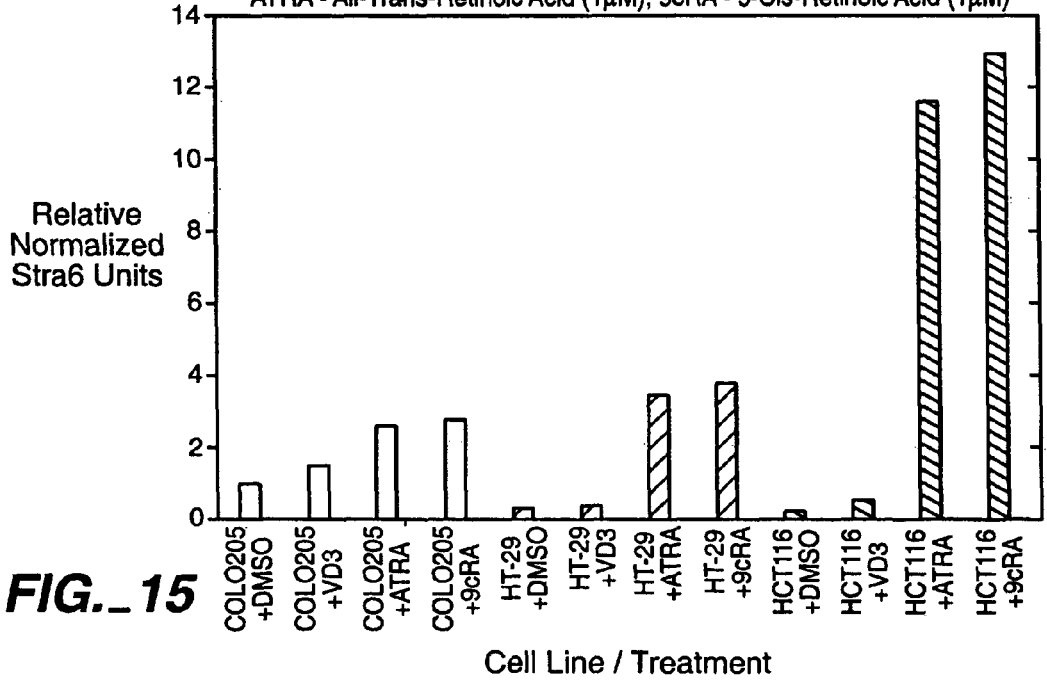
FIG._15

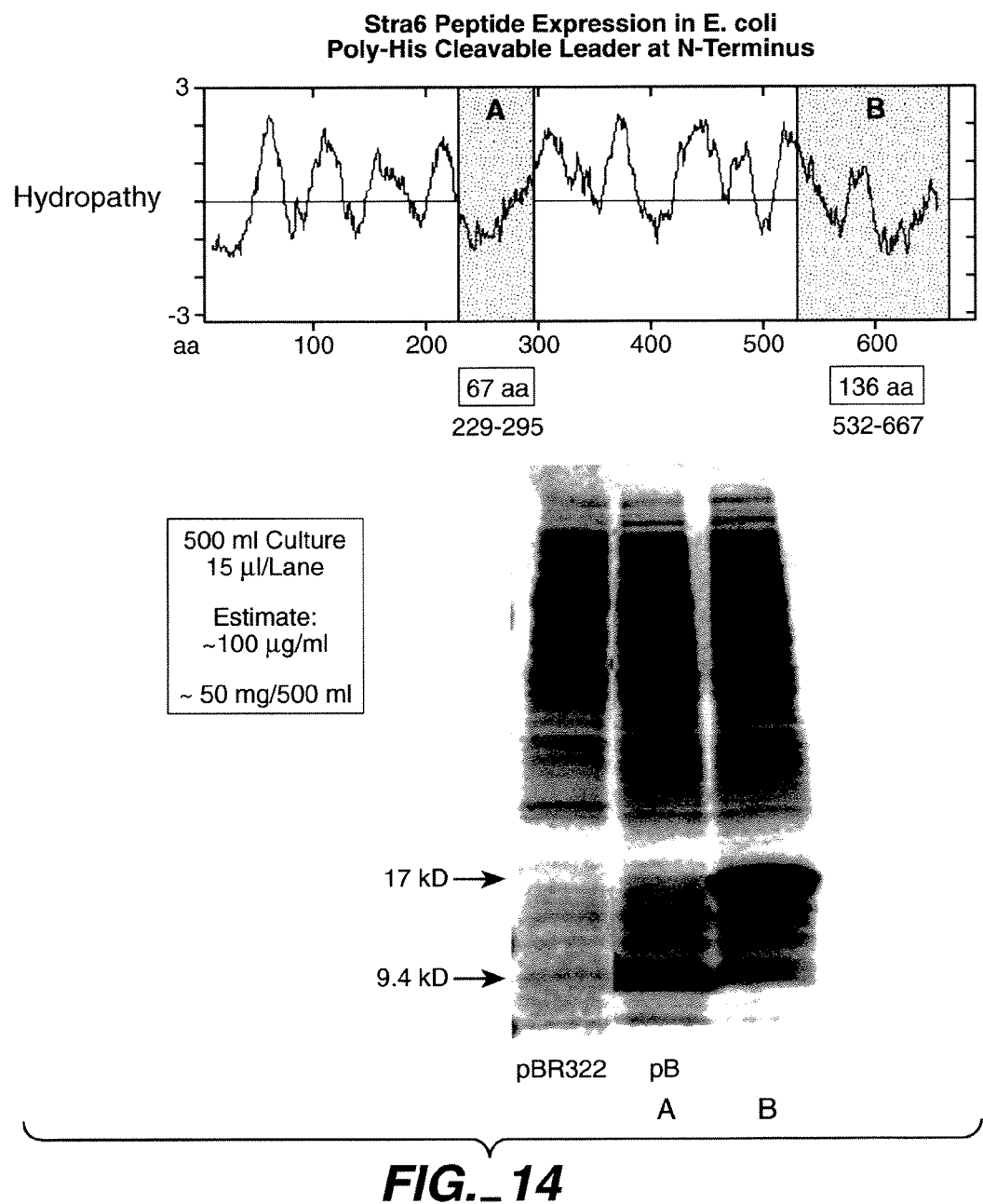
FIG._14

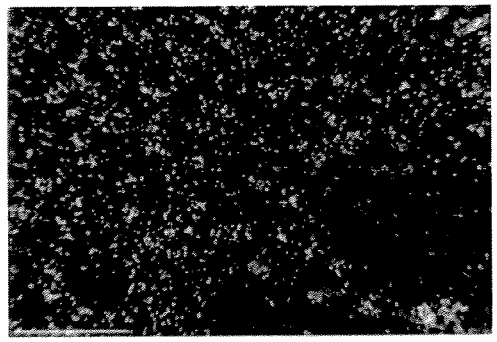
FIG._16A
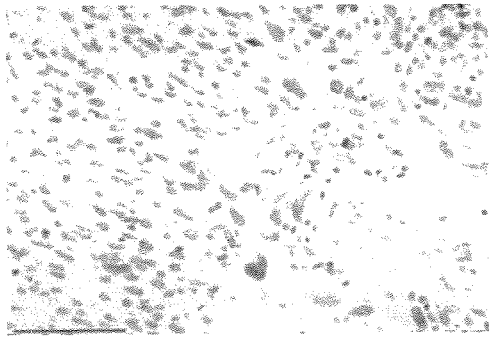
FIG._16B
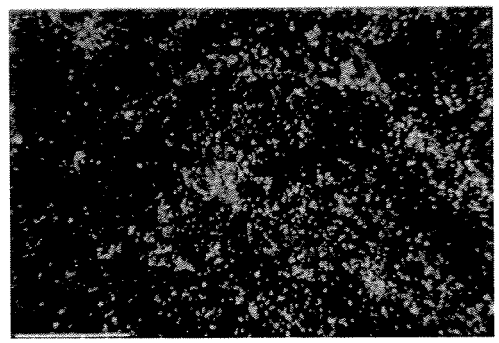
FIG._16C
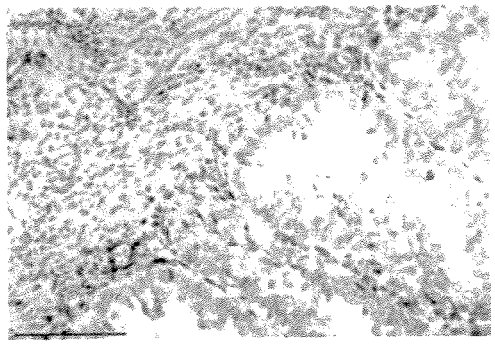
FIG._16D
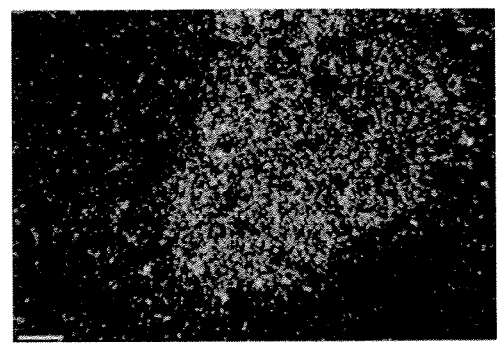
FIG._16E
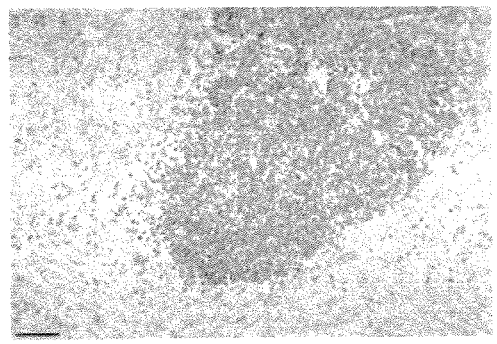
FIG._16F
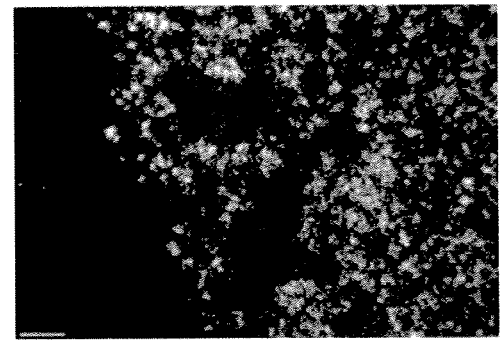
FIG._16G
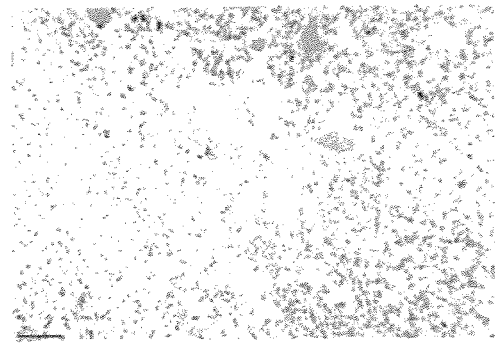
FIG._16H

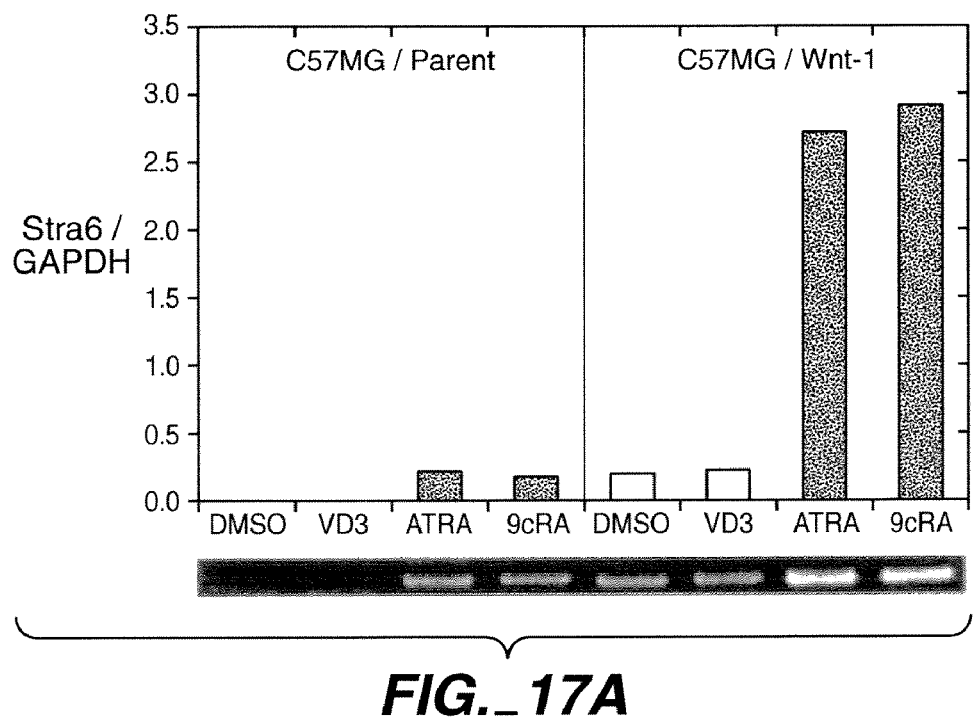
FIG._17A
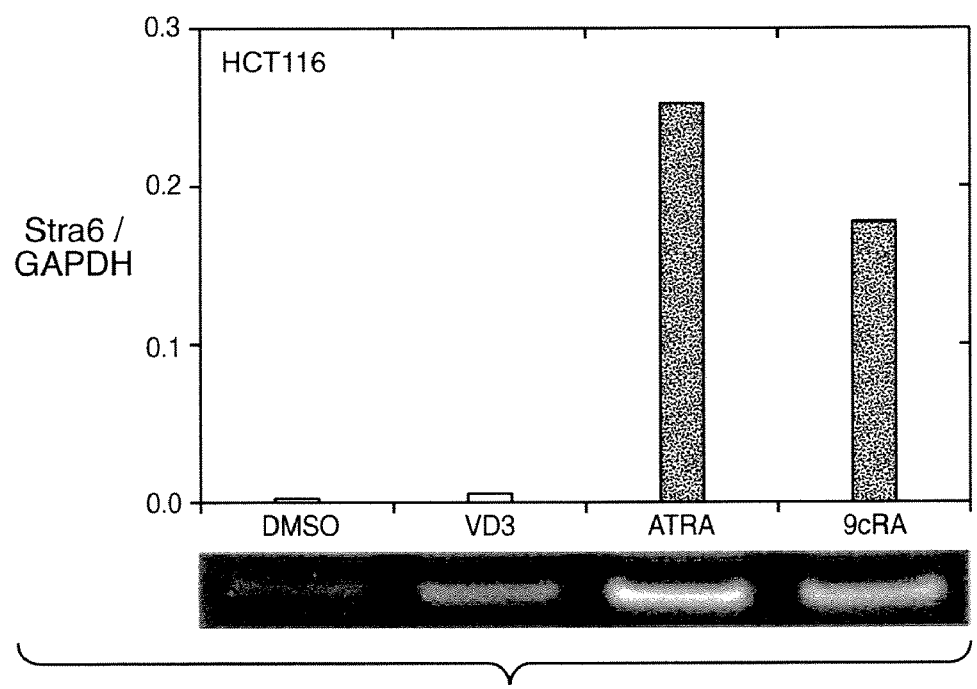
FIG._17C

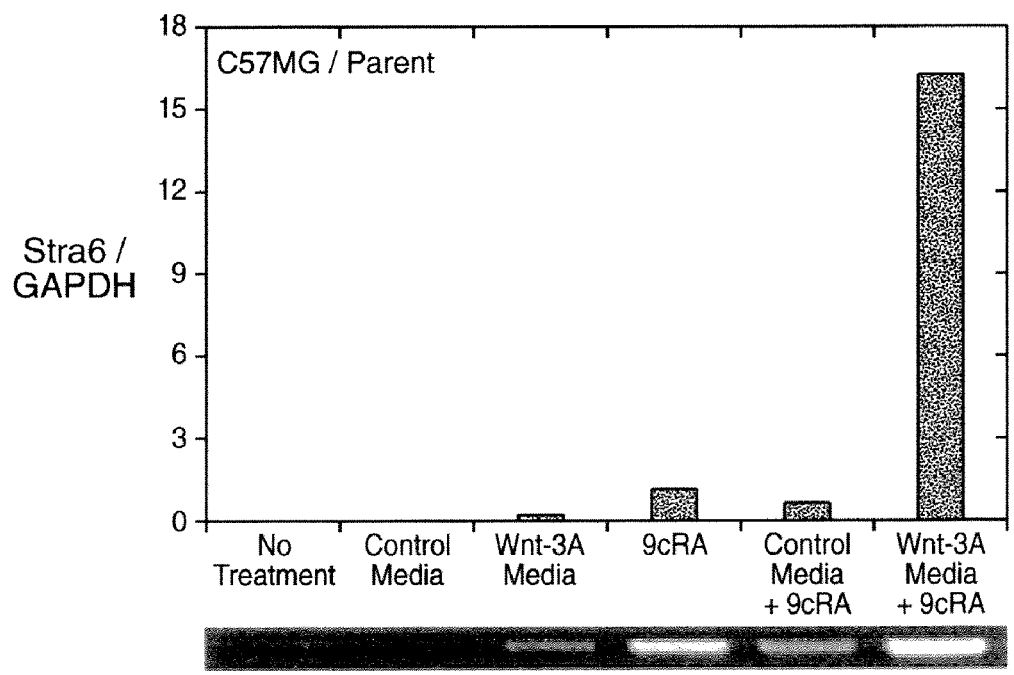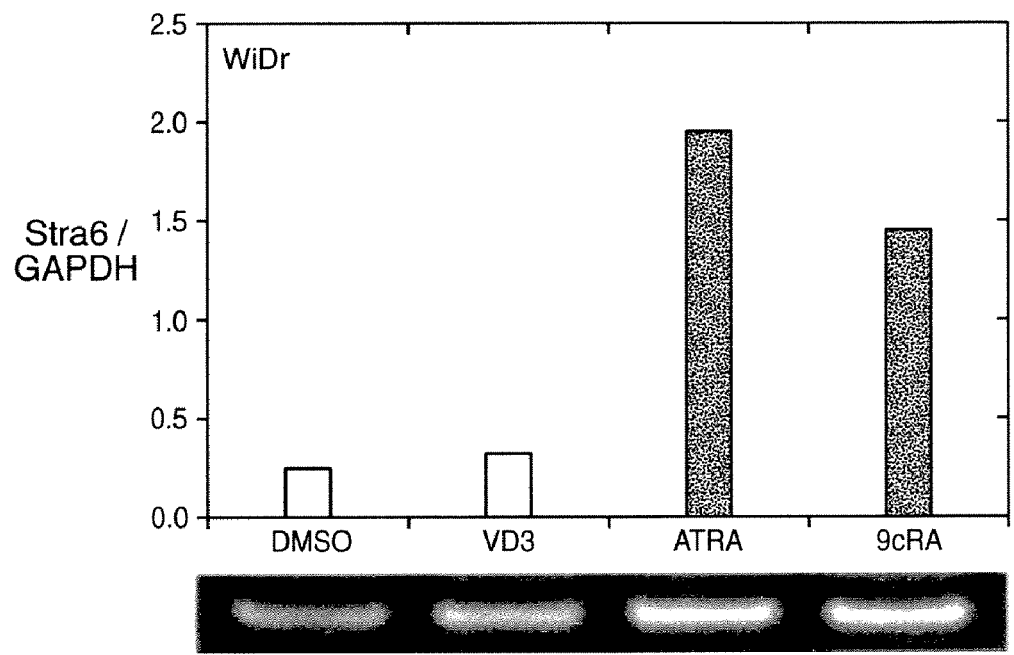
FIG._17B

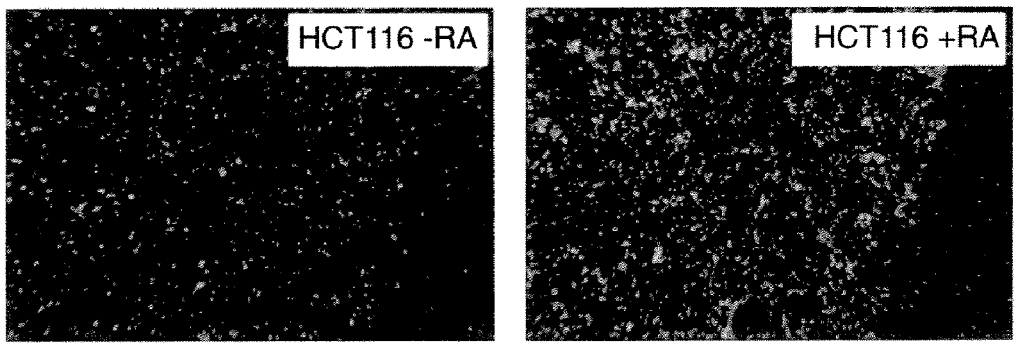
FIG._17D
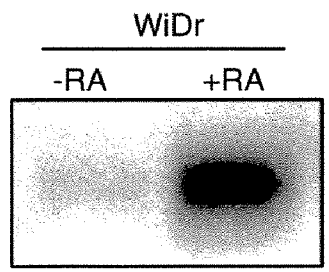
FIG._17E
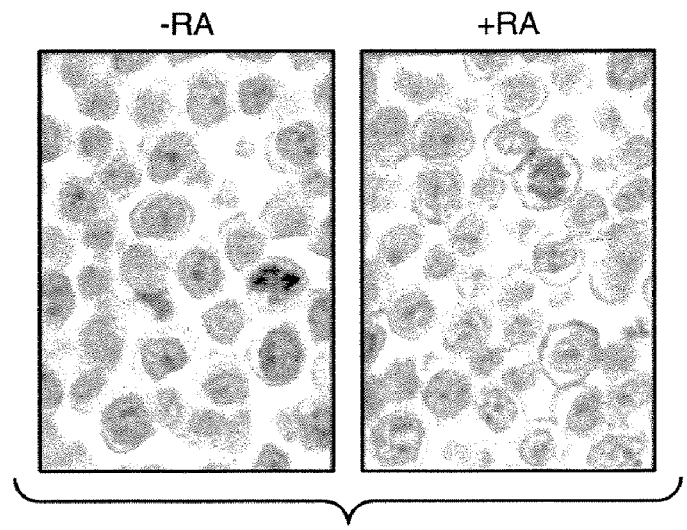
FIG._17F

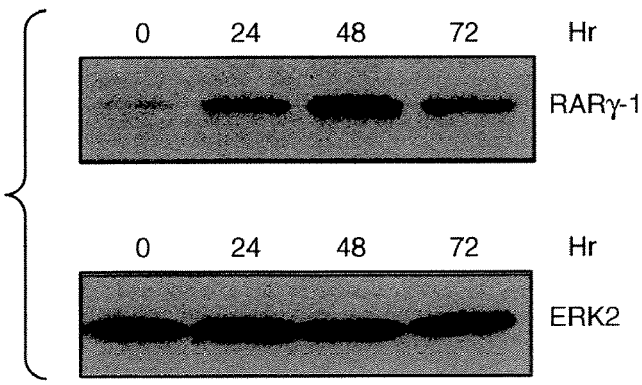
FIG._18A
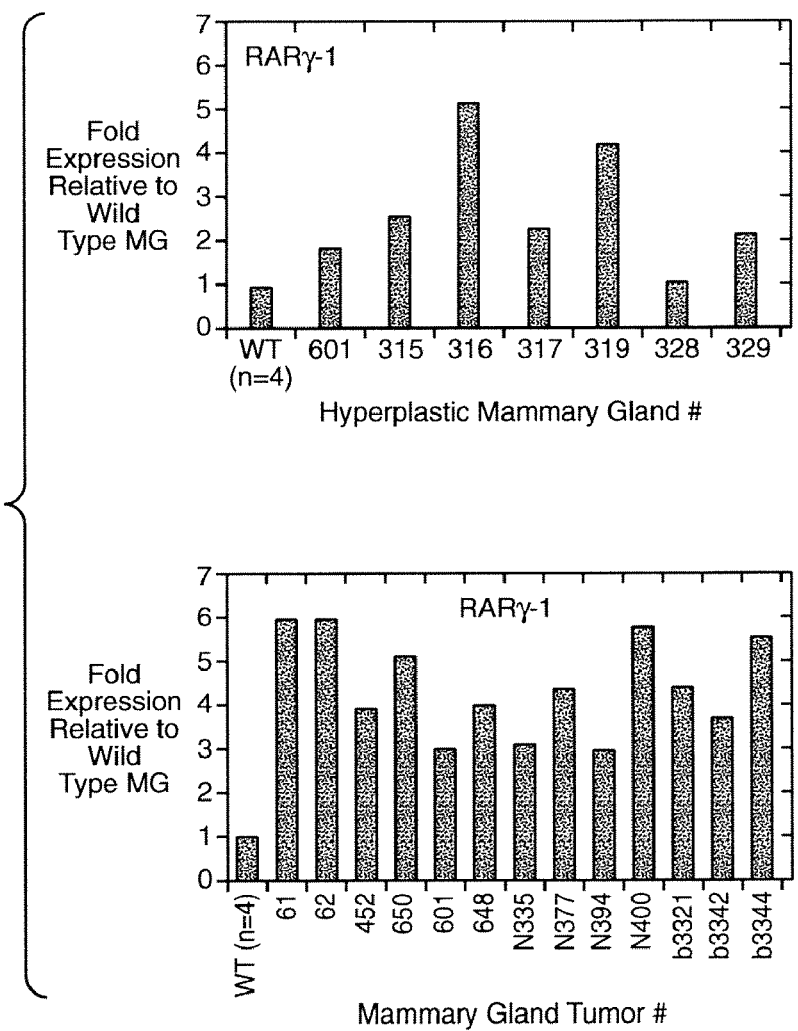
FIG._18B

SEQUENCE LISTING

<160> NUMBER OF SEQ ID NOS: 5

<210> SEQ ID NO 1
<211> LENGTH: 2732
<212> TYPE: DNA
<213> ORGANISM: Homo Sapiens

```
<220> FEATURE:
<221> NAME/KEY: CDS
<222> LOCATION: (49)...(2052)

<400> SEQUENCE: 1
agtcccagac gggcttttcc cagagagcta aaagagaagg gccagaga atg tcg tcc      57
                                                      Met Ser Ser
                                                       1 cag cca gca ggg aac cag acc tcc ccc ggg gcc aca gag gac tac tcc     105
Gln Pro Ala Gly Asn Gln Thr Ser Pro Gly Ala Thr Glu Asp Tyr Ser
     5                  10                  15 tat ggc agc tgg tac atc gat gag ccc cag ggg ggc gag gag ctc cag     153
Tyr Gly Ser Trp Tyr Ile Asp Glu Pro Gln Gly Gly Glu Glu Leu Gln
 20                  25                  30                  35 cca gag ggg gaa gtg ccc tcc tgc cac acc agc ata cca ccc ggc ctg     201
Pro Glu Gly Glu Val Pro Ser Cys His Thr Ser Ile Pro Pro Gly Leu
                 40                  45                  50 tac cac gcc tgc ctg gcc tcg ctg tca atc ctt gtg ctg ctc ctg         249
Tyr His Ala Cys Leu Ala Ser Leu Ser Ile Leu Val Leu Leu Leu
             55                  60                  65 gcc atg ctg gtg agg cgc cgc cag ctc tgg cct gac tgt gtg cgt ggc     297
Ala Met Leu Val Arg Arg Arg Gln Leu Trp Pro Asp Cys Val Arg Gly
         70                  75                  80 agg ccc ggc ctg ccc agc cct gtg gat ttc ttg gct ggg gac agg ccc     345
Arg Pro Gly Leu Pro Ser Pro Val Asp Phe Leu Ala Gly Asp Arg Pro
 85                  90                  95 cgg gca gtg cct gct gct gtt ttc atg gtc ctc ctg agc tcc ctg tgt     393
Arg Ala Val Pro Ala Ala Val Phe Met Val Leu Leu Ser Ser Leu Cys
100                 105                 110                 115 ttg ctg ctc ccc gac gag gac gca ttg ccc ttc ctg act ctc gcc tca     441
Leu Leu Leu Pro Asp Glu Asp Ala Leu Pro Phe Leu Thr Leu Ala Ser
                 120                 125                 130 gca ccc agc caa gat ggg aaa act gag gct cca aga ggg gcc tgg aag     489
Ala Pro Ser Gln Asp Gly Lys Thr Glu Ala Pro Arg Gly Ala Trp Lys
             135                 140                 145 ata ctg gga ctg ttc tat tat gct gcc ctc tac tac cct ctg gct gcc     537
Ile Leu Gly Leu Phe Tyr Tyr Ala Ala Leu Tyr Tyr Pro Leu Ala Ala
         150                 155                 160 tgt gcc acg gct ggc cac aca gct gca cac ctg ctc ggc agc acg ctg     585
Cys Ala Thr Ala Gly His Thr Ala Ala His Leu Leu Gly Ser Thr Leu
165                 170                 175 tcc tgg gcc cac ctt ggg gtc cag gtc tgg cag agg gca gag tgt ccc     633
Ser Trp Ala His Leu Gly Val Gln Val Trp Gln Arg Ala Glu Cys Pro
180                 185                 190                 195 cag gtg ccc aag atc tac aag tac tac tcc ctg ctg gcc tcc ctg cct     681
Gln Val Pro Lys Ile Tyr Lys Tyr Tyr Ser Leu Leu Ala Ser Leu Pro
                 200                 205                 210 ctc ctg ctg ggc ctc gga ttc ctg agc ctt tgg tac cct gtg cag ctg     729
Leu Leu Leu Gly Leu Gly Phe Leu Ser Leu Trp Tyr Pro Val Gln Leu
             215                 220                 225 gtg aga agc ttc agc cgt agg aca gga gca ggc tcc aag ggg ctg cag     777
Val Arg Ser Phe Ser Arg Arg Thr Gly Ala Gly Ser Lys Gly Leu Gln
         230                 235                 240 agc agc tac tct gag gaa tat ctg agg aac ctc ctt tgc agg aag aag     825
Ser Ser Tyr Ser Glu Glu Tyr Leu Arg Asn Leu Leu Cys Arg Lys Lys
245                 250                 255 ctg gga agc agc tac cac acc tcc aag cat ggc ttc ctg tcc tgg gcc     873
Leu Gly Ser Ser Tyr His Thr Ser Lys His Gly Phe Leu Ser Trp Ala
260                 265                 270                 275
```

```
cgc gtc tgc ttg aga cac tgc atc tac act cca cag cca gga ttc cat      921
Arg Val Cys Leu Arg His Cys Ile Tyr Thr Pro Gln Pro Gly Phe His
                280                 285                 290 ctc ccg ctg aag ctg gtg ctt tca gct aca ctg aca ggg acg gcc att      969
Leu Pro Leu Lys Leu Val Leu Ser Ala Thr Leu Thr Gly Thr Ala Ile
                295                 300                 305 tac cag gtg gcc ctg ctg ctg gtg ggc gtg gta ccc act atc cag         1017
Tyr Gln Val Ala Leu Leu Leu Val Gly Val Val Pro Thr Ile Gln
                310                 315                 320 aag gtg agg gca ggg gtc acc acg gat gtc tcc tac ctg ctg gcc ggc     1065
Lys Val Arg Ala Gly Val Thr Thr Asp Val Ser Tyr Leu Leu Ala Gly
                325                 330                 335 ttt gga atc gtg ctc tcc gag gac aag cag gag gtg gtg gag ctg gtg     1113
Phe Gly Ile Val Leu Ser Glu Asp Lys Gln Glu Val Val Glu Leu Val
340                 345                 350                 355 aag cac cat ctg tgg gct ctg gaa gtg tgc tac atc tca gcc ttg gtc     1161
Lys His His Leu Trp Ala Leu Glu Val Cys Tyr Ile Ser Ala Leu Val
                360                 365                 370 ttg tcc tgc tta ctc acc ttc ctg gtc ctg atg cgc tca ctg gtg aca     1209
Leu Ser Cys Leu Leu Thr Phe Leu Val Leu Met Arg Ser Leu Val Thr
                375                 380                 385 cac agg acc aac ctt cga gct ctg cac cga gga gct gcc ctg gac ttg     1257
His Arg Thr Asn Leu Arg Ala Leu His Arg Gly Ala Ala Leu Asp Leu
                390                 395                 400 agt ccc ttg cat cgg agt ccc cat ccc tcc cgc caa gcc ata ttc tgt     1305
Ser Pro Leu His Arg Ser Pro His Pro Ser Arg Gln Ala Ile Phe Cys
                405                 410                 415 tgg atg agc ttc agt gcc tac cag aca gcc ttt atc tgc ctt ggg ctc     1353
Trp Met Ser Phe Ser Ala Tyr Gln Thr Ala Phe Ile Cys Leu Gly Leu
420                 425                 430                 435 ctg gtg cag cag atc atc ttc ttc ctg gga acc acg gcc ctg gcc ttc     1401
Leu Val Gln Gln Ile Ile Phe Phe Leu Gly Thr Thr Ala Leu Ala Phe
                440                 445                 450 ctg gtg ctc atg cct gtg ctc cat ggc agg aac ctc ctg ctc ttc cgt     1449
Leu Val Leu Met Pro Val Leu His Gly Arg Asn Leu Leu Leu Phe Arg
                455                 460                 465 tcc ctg gag tcc tcg tgg ccc ttc tgg ctg act ttg gcc ctg gct gtg     1497
Ser Leu Glu Ser Ser Trp Pro Phe Trp Leu Thr Leu Ala Leu Ala Val
                470                 475                 480 atc ctg cag aac atg gca gcc cat tgg gtc ttc ctg gag act cat gat     1545
Ile Leu Gln Asn Met Ala Ala His Trp Val Phe Leu Glu Thr His Asp
                485                 490                 495 gga cac cca cag ctg acc aac cgg cga gtg ctc tat gca gcc acc ttt     1593
Gly His Pro Gln Leu Thr Asn Arg Arg Val Leu Tyr Ala Ala Thr Phe
500                 505                 510                 515 ctt ctc ttc ccc ctc aat gtg ctg gtg ggt gcc atg gtg gcc acc tgg     1641
Leu Leu Phe Pro Leu Asn Val Leu Val Gly Ala Met Val Ala Thr Trp
                520                 525                 530 cga gtg ctc ctc tct gcc ctc tac aac gcc atc cac ctt ggc cag atg     1689
Arg Val Leu Leu Ser Ala Leu Tyr Asn Ala Ile His Leu Gly Gln Met
                535                 540                 545 gac ctc agc ctg ctg cca ccg aga gcc gcc act ctc gac ccc ggc tac     1737
Asp Leu Ser Leu Leu Pro Pro Arg Ala Ala Thr Leu Asp Pro Gly Tyr
                550                 555                 560 tac acg tac cga aac ttc ttg aag att gaa gtc agc cag tcg cat cca     1785
Tyr Thr Tyr Arg Asn Phe Leu Lys Ile Glu Val Ser Gln Ser His Pro
                565                 570                 575 gcc atg aca gcc ttc tgc tcc ctg ctc ctg caa gcg cag agc ctc cta     1833
Ala Met Thr Ala Phe Cys Ser Leu Leu Leu Gln Ala Gln Ser Leu Leu
580                 585                 590                 595
```

```
ccc agg acc atg gca gcc ccc cag gac agc ctc aga cca ggg gag gaa   1881
Pro Arg Thr Met Ala Ala Pro Gln Asp Ser Leu Arg Pro Gly Glu Glu
            600                 605                 610 gac gaa ggg atg cag ctg cta cag aca aag gac tcc atg gcc aag gga   1929
Asp Glu Gly Met Gln Leu Leu Gln Thr Lys Asp Ser Met Ala Lys Gly
            615                 620                 625 gct agg ccc ggg gcc agc cgc ggc agg gct cgc tgg ggt ctg gcc tac   1977
Ala Arg Pro Gly Ala Ser Arg Gly Arg Ala Arg Trp Gly Leu Ala Tyr
            630                 635                 640 acg ctg ctg cac aac cca acc ctg cag gtc ttc cgc aag acg gcc ctg   2025
Thr Leu Leu His Asn Pro Thr Leu Gln Val Phe Arg Lys Thr Ala Leu
            645                 650                 655 ttg ggt gcc aat ggt gcc cag ccc tga gggcagggaa ggtcaaccca          2072
Leu Gly Ala Asn Gly Ala Gln Pro  *
660                 665 cctgcccatc tgtgctgagg catgttcctg cctaccatcc tcctccctcc ccggctctcc  2132
tcccagcatc acaccagcca tgcagccagc aggtcctccg gatcactgtg gttgggtgga  2192
ggtctgtctg cactgggagc ctcaggaggg ctctgctcca cccacttggc tatgggagag  2252
ccagcagggg ttctggagaa aaaaactggt gggttagggc cttggtccag gagccagttg  2312
agccagggca gccacatcca ggcgtctccc taccctggct ctgccatcag ccttgaaggg  2372
cctcgatgaa gccttctctg gaaccactcc agcccagctc cacctcagcc ttggccttca  2432
cgctgtggaa gcagccaagg cacttcctca ccccctcagc gccacggacc tctctgggga  2492
gtggccggaa agctcccggt cctctggcct gcagggcagc ccaagtcatg actcagacca  2552
ggtcccacac tgagctgccc acactcgaga gccagatatt tttgtagttt ttatgccttt  2612
ggctattatg aaagaggtta gtgtgttccc tgcaataaac ttgttcctga gaaaaaaaaa  2672
aaaaaaaaaa aaaaaaaaaa aaaaaaaaaa aaaaaaaaaa aaaaaaaaaa aaaaaaaaaa  2732

<210> SEQ ID NO 2
<211> LENGTH: 667
<212> TYPE: PRT
<213> ORGANISM: Homo Sapiens

<400> SEQUENCE: 2

Met Ser Ser Gln Pro Ala Gly Asn Gln Thr Ser Pro Gly Ala Thr Glu
1               5                   10                  15

Asp Tyr Ser Tyr Gly Ser Trp Tyr Ile Asp Glu Pro Gln Gly Gly Glu
                20                  25                  30

Glu Leu Gln Pro Glu Gly Glu Val Pro Ser Cys His Thr Ser Ile Pro
            35                  40                  45

Pro Gly Leu Tyr His Ala Cys Leu Ala Ser Leu Ser Ile Leu Val Leu
        50                  55                  60

Leu Leu Leu Ala Met Leu Val Arg Arg Gln Leu Trp Pro Asp Cys
65                  70                  75                  80

Val Arg Gly Arg Pro Gly Leu Pro Ser Pro Val Asp Phe Leu Ala Gly
                85                  90                  95

Asp Arg Pro Arg Ala Val Pro Ala Ala Val Phe Met Val Leu Leu Ser
                100                 105                 110

Ser Leu Cys Leu Leu Pro Asp Glu Asp Ala Leu Pro Phe Leu Thr
            115                 120                 125

Leu Ala Ser Ala Pro Ser Gln Asp Gly Lys Thr Glu Ala Pro Arg Gly
        130                 135                 140

Ala Trp Lys Ile Leu Gly Leu Phe Tyr Tyr Ala Ala Leu Tyr Tyr Pro
145                 150                 155                 160
```

-continued

```
Leu Ala Ala Cys Ala Thr Ala Gly His Thr Ala Ala His Leu Leu Gly
                165                 170                 175
Ser Thr Leu Ser Trp Ala His Leu Gly Val Gln Val Trp Gln Arg Ala
            180                 185                 190
Glu Cys Pro Gln Val Pro Lys Ile Tyr Lys Tyr Tyr Ser Leu Leu Ala
        195                 200                 205
Ser Leu Pro Leu Leu Leu Gly Leu Gly Phe Leu Ser Leu Trp Tyr Pro
    210                 215                 220
Val Gln Leu Val Arg Ser Phe Ser Arg Arg Thr Gly Ala Gly Ser Lys
225                 230                 235                 240
Gly Leu Gln Ser Ser Tyr Ser Glu Glu Tyr Leu Arg Asn Leu Leu Cys
                245                 250                 255
Arg Lys Lys Leu Gly Ser Ser Tyr His Thr Ser Lys His Gly Phe Leu
            260                 265                 270
Ser Trp Ala Arg Val Cys Leu Arg His Cys Ile Tyr Thr Pro Gln Pro
        275                 280                 285
Gly Phe His Leu Pro Leu Lys Leu Val Leu Ser Ala Thr Leu Thr Gly
    290                 295                 300
Thr Ala Ile Tyr Gln Val Ala Leu Leu Leu Val Gly Val Val Pro
305                 310                 315                 320
Thr Ile Gln Lys Val Arg Ala Gly Val Thr Thr Asp Val Ser Tyr Leu
                325                 330                 335
Leu Ala Gly Phe Gly Ile Val Leu Ser Glu Asp Lys Gln Glu Val Val
            340                 345                 350
Glu Leu Val Lys His His Leu Trp Ala Leu Glu Val Cys Tyr Ile Ser
        355                 360                 365
Ala Leu Val Leu Ser Cys Leu Leu Thr Phe Leu Val Leu Met Arg Ser
    370                 375                 380
Leu Val Thr His Arg Thr Asn Leu Arg Ala Leu His Arg Gly Ala Ala
385                 390                 395                 400
Leu Asp Leu Ser Pro Leu His Arg Ser Pro His Pro Ser Arg Gln Ala
                405                 410                 415
Ile Phe Cys Trp Met Ser Phe Ser Ala Tyr Gln Thr Ala Phe Ile Cys
            420                 425                 430
Leu Gly Leu Leu Val Gln Gln Ile Ile Phe Phe Leu Gly Thr Thr Ala
        435                 440                 445
Leu Ala Phe Leu Val Leu Met Pro Val Leu His Gly Arg Asn Leu Leu
    450                 455                 460
Leu Phe Arg Ser Leu Glu Ser Ser Trp Pro Phe Trp Leu Thr Leu Ala
465                 470                 475                 480
Leu Ala Val Ile Leu Gln Asn Met Ala Ala His Trp Val Phe Leu Glu
                485                 490                 495
Thr His Asp Gly His Pro Gln Leu Thr Asn Arg Arg Val Leu Tyr Ala
            500                 505                 510
Ala Thr Phe Leu Leu Phe Pro Leu Asn Val Leu Val Gly Ala Met Val
        515                 520                 525
Ala Thr Trp Arg Val Leu Leu Ser Ala Leu Tyr Asn Ala Ile His Leu
    530                 535                 540
Gly Gln Met Asp Leu Ser Leu Leu Pro Pro Arg Ala Ala Thr Leu Asp
545                 550                 555                 560
Pro Gly Tyr Tyr Thr Tyr Arg Asn Phe Leu Lys Ile Glu Val Ser Gln
                565                 570                 575
Ser His Pro Ala Met Thr Ala Phe Cys Ser Leu Leu Leu Gln Ala Gln
            580                 585                 590
```

```
Ser Leu Leu Pro Arg Thr Met Ala Ala Pro Gln Asp Ser Leu Arg Pro
        595                 600                 605

Gly Glu Glu Asp Glu Gly Met Gln Leu Leu Gln Thr Lys Asp Ser Met
610                 615                 620

Ala Lys Gly Ala Arg Pro Gly Ala Ser Arg Gly Arg Ala Arg Trp Gly
625                 630                 635                 640

Leu Ala Tyr Thr Leu Leu His Asn Pro Thr Leu Gln Val Phe Arg Lys
                645                 650                 655

Thr Ala Leu Leu Gly Ala Asn Gly Ala Gln Pro
            660                 665

<210> SEQ ID NO 3
<211> LENGTH: 676
<212> TYPE: DNA
<213> ORGANISM: Homo sapiens
<220> FEATURE:
<221> NAME/KEY: misc_feature
<222> LOCATION: (26)...(26)
<223> OTHER INFORMATION: n = A, T, C or G

<400> SEQUENCE: 3
gtgctctccg aggacaagca ggaggnggtg gagctggtga agcaccatct gtgggctctg      60
gaagtgtgct acatctcagc cttggtcttg tcctgcttac tcaccttcct ggtcctgatg     120
cgctcactgg tgacacacag gaccaacctt cgagctctgc accgaggagc tgccctggac     180
ttgagtccct tgcatcggag tccccatccc tcccgccaag ccatattctg ttggatgagc     240
ttcagtgcct accagacagc ctttatctgc cttgggctcc tggtgcagca gatcatcttc     300
ttcctgggaa ccacggccct ggccttcctg gtgctcatgc ctgtgctcca tggcaggaac     360
ctcctgctct tccgttccct ggagtcctcg tggcccttct ggctgacttt ggccctggct     420
gtgatcctgc agaacatggc agcccattgg gtcttcctgg agactcatga tggacaccca     480
cagctgacca accggcgagt gctctatgca gccacctttc ttctcttccc cctcaatgtg     540
ctggtgggtg ccatggtggc cacctggcga gtgctcctct ctgccctcta caacgccatc     600
caccttggcc agatggacct cagcctgctg ccaccgagag ccgccactct cgaccccggc     660
tactacacgt accgaa                                                     676

<210> SEQ ID NO 4
<211> LENGTH: 2777
<212> TYPE: DNA
<213> ORGANISM: Homo sapiens
<220> FEATURE:
<221> NAME/KEY: CDS
<222> LOCATION: (186)...(2160)

<400> SEQUENCE: 4
cacaaccagc caccctcta ggatcccagc ccagctggtg ctgggctcag aggagaaggc       60
cccgtgttgg gagcaccctg cttgcctgga gggacaagtt ccggagagag atcaataaag     120
gaaaggaaag agacaaggaa gggagaggtc aggagagcgc ttgattggag gagaagggcc     180 agaga atg tcg tcc cag cca gca ggg aac cag acc tcc ccc ggg gcc aca     230
      Met Ser Ser Gln Pro Ala Gly Asn Gln Thr Ser Pro Gly Ala Thr
      1               5                   10                  15 gag gac tac tcc tat ggc agc tgg tac atc gat gag ccc cag ggg ggc      278
Glu Asp Tyr Ser Tyr Gly Ser Trp Tyr Ile Asp Glu Pro Gln Gly Gly
                20                  25                  30 gag gag ctc cag cca gag ggg gaa gtg ccc tcc tgc cac acc agc ata      326
Glu Glu Leu Gln Pro Glu Gly Glu Val Pro Ser Cys His Thr Ser Ile
            35                  40                  45
```

```
cca ccc ggc ctg tac cac gcc tgc ctg gcc tcg ctg tca atc ctt gtg      374
Pro Pro Gly Leu Tyr His Ala Cys Leu Ala Ser Leu Ser Ile Leu Val
         50                  55                  60 ctg ctg ctc ctg gcc atg ctg gtg agg cgc cgc cag ctc tgg cct gac      422
Leu Leu Leu Leu Ala Met Leu Val Arg Arg Arg Gln Leu Trp Pro Asp
 65                  70                  75 tgt gtg cgt ggc agg ccc ggc ctg ccc agg ccc cgg gca gtg cct gct      470
Cys Val Arg Gly Arg Pro Gly Leu Pro Arg Pro Arg Ala Val Pro Ala
 80                  85                  90                  95 gct gtt ttc atg gtc ctc ctg agc tcc ctg tgt ttg ctc ctc ccc gac      518
Ala Val Phe Met Val Leu Leu Ser Ser Leu Cys Leu Leu Leu Pro Asp
                100                 105                 110 gag gac gca ttg ccc ttc ctg act ctc gcc tca gca ccc agc caa gat      566
Glu Asp Ala Leu Pro Phe Leu Thr Leu Ala Ser Ala Pro Ser Gln Asp
            115                 120                 125 ggg aaa act gag gct cca aga ggg gcc tgg aag ata ctg gga ctg ttc      614
Gly Lys Thr Glu Ala Pro Arg Gly Ala Trp Lys Ile Leu Gly Leu Phe
        130                 135                 140 tat tat gcc ctc tac tac cct ctg gct gcc tgt gcc acg gct ggc          662
Tyr Tyr Ala Ala Leu Tyr Tyr Pro Leu Ala Ala Cys Ala Thr Ala Gly
145                 150                 155 cac aca gct gca cac ctg ctc ggc agc acg ctg tcc tgg gcc cac ctt      710
His Thr Ala Ala His Leu Leu Gly Ser Thr Leu Ser Trp Ala His Leu
160                 165                 170                 175 ggg gtc cag gtc tgg cag agg gca gag tgt ccc cag gtg ccc aag atc      758
Gly Val Gln Val Trp Gln Arg Ala Glu Cys Pro Gln Val Pro Lys Ile
                180                 185                 190 tac aag tac tac tcc ctg ctg gcc tcc ctg cct ctc ctg ggc ctc          806
Tyr Lys Tyr Tyr Ser Leu Leu Ala Ser Leu Pro Leu Leu Gly Leu
            195                 200                 205 gga ttc ctg agc ctt tgg tac cct gtg cag ctg gtg aga agc ttc agc      854
Gly Phe Leu Ser Leu Trp Tyr Pro Val Gln Leu Val Arg Ser Phe Ser
        210                 215                 220 cgt agg aca gga gca ggc tcc aag ggg ctg cag agc agc tac tct gag      902
Arg Arg Thr Gly Ala Gly Ser Lys Gly Leu Gln Ser Ser Tyr Ser Glu
225                 230                 235 gaa tat ctg agg aac ctc ctt tgc agg aag aag ctg gga agc agc tac      950
Glu Tyr Leu Arg Asn Leu Leu Cys Arg Lys Lys Leu Gly Ser Ser Tyr
240                 245                 250                 255 cac acc tcc aag cat ggc ttc ctg tcc tgg gcc cgc gtc tgc ttg aga      998
His Thr Ser Lys His Gly Phe Leu Ser Trp Ala Arg Val Cys Leu Arg
                260                 265                 270 cac tgc atc tac act cca cag cca gga ttc cat ctc ccg ctg aag ctg     1046
His Cys Ile Tyr Thr Pro Gln Pro Gly Phe His Leu Pro Leu Lys Leu
            275                 280                 285 gtg ctt tca gct aca ctg aca ggg acg gcc att tac cag gtg gcc ctg     1094
Val Leu Ser Ala Thr Leu Thr Gly Thr Ala Ile Tyr Gln Val Ala Leu
        290                 295                 300 ctg ctg ctg gtg ggc gtg gta ccc act atc cag aag gtg agg gca ggg     1142
Leu Leu Leu Val Gly Val Val Pro Thr Ile Gln Lys Val Arg Ala Gly
305                 310                 315 gtc acc acg gat gtc tcc tac ctg ctg gcc ggc ttt gga atc gtg ctc     1190
Val Thr Thr Asp Val Ser Tyr Leu Leu Ala Gly Phe Gly Ile Val Leu
320                 325                 330                 335 tcc gag gac aag cag gag gtg gtg gag ctg gtg aag cac cat ctg tgg     1238
Ser Glu Asp Lys Gln Glu Val Val Glu Leu Val Lys His His Leu Trp
                340                 345                 350 gct ctg gaa gtg tgc tac atc tca gcc ttg gtc ttg tcc tgc tta ctc     1286
Ala Leu Glu Val Cys Tyr Ile Ser Ala Leu Val Leu Ser Cys Leu Leu
            355                 360                 365
```

```
acc ttc ctg gtc ctg atg cgc tca ctg gtg aca cac agg acc aac ctt    1334
Thr Phe Leu Val Leu Met Arg Ser Leu Val Thr His Arg Thr Asn Leu
    370                 375                 380 cga gct ctg cac cga gga gct gcc ctg gac ttg agt ccc ttg cat cgg    1382
Arg Ala Leu His Arg Gly Ala Ala Leu Asp Leu Ser Pro Leu His Arg
385                 390                 395 agt ccc cat ccc tcc cgc caa gcc ata ttc tgt tgg atg agc ttc agt    1430
Ser Pro His Pro Ser Arg Gln Ala Ile Phe Cys Trp Met Ser Phe Ser
400                 405                 410                 415 gcc tac cag aca gcc ttt atc tgc ctt ggg ctc ctg gtg cag cag atc    1478
Ala Tyr Gln Thr Ala Phe Ile Cys Leu Gly Leu Leu Val Gln Gln Ile
        420                 425                 430 atc ttc ttc ctg gga acc acg gcc ctg gcc ttc ctg gtg ctc atg cct    1526
Ile Phe Phe Leu Gly Thr Thr Ala Leu Ala Phe Leu Val Leu Met Pro
            435                 440                 445 gtg ctc cat ggc agg aac ctc ctg ctc ttc cgt tcc ctg gag tcc tcg    1574
Val Leu His Gly Arg Asn Leu Leu Leu Phe Arg Ser Leu Glu Ser Ser
                450                 455                 460 tgg ccc ttc tgg ctg act ttg gcc ctg gct gtg atc ctg cag aac atg    1622
Trp Pro Phe Trp Leu Thr Leu Ala Leu Ala Val Ile Leu Gln Asn Met
465                 470                 475 gca gcc cat tgg gtc ttc ctg gag act cat gat gga cac cca cag ctg    1670
Ala Ala His Trp Val Phe Leu Glu Thr His Asp Gly His Pro Gln Leu
480                 485                 490                 495 acc aac cgg cga gtg ctc tat gca gcc acc ttt ctt ctc ttc ccc ctc    1718
Thr Asn Arg Arg Val Leu Tyr Ala Ala Thr Phe Leu Leu Phe Pro Leu
                500                 505                 510 aat gtg ctg gtg ggt gcc ata gtg gcc acc tgg cga gtg ctc ctc tct    1766
Asn Val Leu Val Gly Ala Ile Val Ala Thr Trp Arg Val Leu Leu Ser
            515                 520                 525 gcc ctc tac aac gcc atc cac ctt ggc cag atg gac ctc agc ctg ctg    1814
Ala Leu Tyr Asn Ala Ile His Leu Gly Gln Met Asp Leu Ser Leu Leu
        530                 535                 540 cca ccg aga gcc gcc act ctc gac ccc ggc tac tac acg tac cga aac    1862
Pro Pro Arg Ala Ala Thr Leu Asp Pro Gly Tyr Tyr Thr Tyr Arg Asn
545                 550                 555 ttc ttg aag att gaa gtc agc cag tcg cat cca gcc atg aca gcc ttc    1910
Phe Leu Lys Ile Glu Val Ser Gln Ser His Pro Ala Met Thr Ala Phe
560                 565                 570                 575 tgc tcc ctg ctc ctg caa gcg cag agc ctc cta ccc agg acc atg gca    1958
Cys Ser Leu Leu Leu Gln Ala Gln Ser Leu Leu Pro Arg Thr Met Ala
                580                 585                 590 gcc ccc cag gac agc ctc aga cca ggg gag gaa gac gaa ggg atg cag    2006
Ala Pro Gln Asp Ser Leu Arg Pro Gly Glu Glu Asp Glu Gly Met Gln
            595                 600                 605 ctg cta cag aca aag gac tcc atg gcc aag gga gct agg ccc ggg gcc    2054
Leu Leu Gln Thr Lys Asp Ser Met Ala Lys Gly Ala Arg Pro Gly Ala
        610                 615                 620 agc cgc ggc agg gct cgc tgg ggt ctg gcc tac acg ctg ctg cac aac    2102
Ser Arg Gly Arg Ala Arg Trp Gly Leu Ala Tyr Thr Leu Leu His Asn
625                 630                 635 cca acc ctg cag gtc ttc cgc aag acg gcc ctg ttg ggt gcc aat ggt    2150
Pro Thr Leu Gln Val Phe Arg Lys Thr Ala Leu Leu Gly Ala Asn Gly
640                 645                 650                 655 gcc cag ccc t gagggcaggg aaggtcaacc cacctgccca tctgtgctga         2200
Ala Gln Pro ggcatgttcc tgcctaccac ctcctccctc cccggctctc ctcccagcat cacaccagcc    2260
atgcagccag caggtcctcc ggatcactgt ggttgggtgg aggtctgtct gcactgggag    2320
cctcaggagg gctctgctcc acccacttgg ctatgggaga gccagcaggg gttctggaga    2380
```

-continued

```
aagaaactgg tgggttaggg ccttggtcca ggagccagtt gagccagggc agccacatcc    2440
aggcgtctcc ctaccctggc tctgccatca gccttgaagg gcctcgatga agccttctct    2500
ggaaccactc cagcccagct ccacctcagc cttggccttc acgctgtgga agcagccaag    2560
gcacttcctc acccctcag cgccacggac ctctctgggg agtggccgga aagctcccgg    2620
gcctctggcc tgcagggcag cccaagtcat gactcagacc aggtcccaca ctgagctgcc    2680
cacactcgag agccagatat ttttgtagtt tttatgcctt tggctattat gaaagaggtt    2740
agtgtgttcc ctgcaataaa cttgttcctg agaaaaa                             2777
```

```
<210> SEQ ID NO 5
<211> LENGTH: 658
<212> TYPE: PRT
<213> ORGANISM: Homo sapiens

<400> SEQUENCE: 5

Met Ser Ser Gln Pro Ala Gly Asn Gln Thr Ser Pro Gly Ala Thr Glu
 1               5                  10                  15

Asp Tyr Ser Tyr Gly Ser Trp Tyr Ile Asp Glu Pro Gln Gly Gly Glu
                20                  25                  30

Glu Leu Gln Pro Glu Gly Glu Val Pro Ser Cys His Thr Ser Ile Pro
            35                  40                  45

Pro Gly Leu Tyr His Ala Cys Leu Ala Ser Leu Ser Ile Leu Val Leu
        50                  55                  60

Leu Leu Leu Ala Met Leu Val Arg Arg Gln Leu Trp Pro Asp Cys
 65                  70                  75                  80

Val Arg Gly Arg Pro Gly Leu Pro Arg Pro Arg Ala Val Pro Ala Ala
                 85                  90                  95

Val Phe Met Val Leu Leu Ser Ser Leu Cys Leu Leu Pro Asp Glu
                100                 105                 110

Asp Ala Leu Pro Phe Leu Thr Leu Ala Ser Ala Pro Ser Gln Asp Gly
            115                 120                 125

Lys Thr Glu Ala Pro Arg Gly Ala Trp Lys Ile Leu Gly Leu Phe Tyr
        130                 135                 140

Tyr Ala Ala Leu Tyr Tyr Pro Leu Ala Ala Cys Ala Thr Ala Gly His
145                 150                 155                 160

Thr Ala Ala His Leu Leu Gly Ser Thr Leu Ser Trp Ala His Leu Gly
                165                 170                 175

Val Gln Val Trp Gln Arg Ala Glu Cys Pro Gln Val Pro Lys Ile Tyr
            180                 185                 190

Lys Tyr Tyr Ser Leu Leu Ala Ser Leu Pro Leu Leu Gly Leu Gly
        195                 200                 205

Phe Leu Ser Leu Trp Tyr Pro Val Gln Leu Val Arg Ser Phe Ser Arg
    210                 215                 220

Arg Thr Gly Ala Gly Ser Lys Gly Leu Gln Ser Ser Tyr Ser Glu Glu
225                 230                 235                 240

Tyr Leu Arg Asn Leu Leu Cys Arg Lys Lys Leu Gly Ser Ser Tyr His
                245                 250                 255

Thr Ser Lys His Gly Phe Leu Ser Trp Ala Arg Val Cys Leu Arg His
            260                 265                 270

Cys Ile Tyr Thr Pro Gln Pro Gly Phe His Leu Pro Leu Lys Leu Val
        275                 280                 285

Leu Ser Ala Thr Leu Thr Gly Thr Ala Ile Tyr Gln Val Ala Leu Leu
    290                 295                 300
```

-continued

```
Leu Leu Val Gly Val Val Pro Thr Ile Gln Lys Val Arg Ala Gly Val
305                 310                 315                 320

Thr Thr Asp Val Ser Tyr Leu Leu Ala Gly Phe Gly Ile Val Leu Ser
                325                 330                 335

Glu Asp Lys Gln Glu Val Val Glu Leu Val Lys His His Leu Trp Ala
                340                 345                 350

Leu Glu Val Cys Tyr Ile Ser Ala Leu Val Leu Ser Cys Leu Leu Thr
                355                 360                 365

Phe Leu Val Leu Met Arg Ser Leu Val Thr His Arg Thr Asn Leu Arg
370                 375                 380

Ala Leu His Arg Gly Ala Ala Leu Asp Leu Ser Pro Leu His Arg Ser
385                 390                 395                 400

Pro His Pro Ser Arg Gln Ala Ile Phe Cys Trp Met Ser Phe Ser Ala
                405                 410                 415

Tyr Gln Thr Ala Phe Ile Cys Leu Gly Leu Leu Val Gln Gln Ile Ile
                420                 425                 430

Phe Phe Leu Gly Thr Thr Ala Leu Ala Phe Leu Val Leu Met Pro Val
                435                 440                 445

Leu His Gly Arg Asn Leu Leu Leu Phe Arg Ser Leu Glu Ser Ser Trp
450                 455                 460

Pro Phe Trp Leu Thr Leu Ala Leu Ala Val Ile Leu Gln Asn Met Ala
465                 470                 475                 480

Ala His Trp Val Phe Leu Glu Thr His Asp Gly His Pro Gln Leu Thr
                485                 490                 495

Asn Arg Arg Val Leu Tyr Ala Ala Thr Phe Leu Leu Phe Pro Leu Asn
                500                 505                 510

Val Leu Val Gly Ala Ile Val Ala Thr Trp Arg Val Leu Leu Ser Ala
                515                 520                 525

Leu Tyr Asn Ala Ile His Leu Gly Gln Met Asp Leu Ser Leu Leu Pro
530                 535                 540

Pro Arg Ala Ala Thr Leu Asp Pro Gly Tyr Tyr Thr Tyr Arg Asn Phe
545                 550                 555                 560

Leu Lys Ile Glu Val Ser Gln Ser His Pro Ala Met Thr Ala Phe Cys
                565                 570                 575

Ser Leu Leu Leu Gln Ala Gln Ser Leu Leu Pro Arg Thr Met Ala Ala
                580                 585                 590

Pro Gln Asp Ser Leu Arg Pro Gly Glu Glu Asp Glu Gly Met Gln Leu
                595                 600                 605

Leu Gln Thr Lys Asp Ser Met Ala Lys Gly Ala Arg Pro Gly Ala Ser
                610                 615                 620

Arg Gly Arg Ala Arg Trp Gly Leu Ala Tyr Thr Leu Leu His Asn Pro
625                 630                 635                 640

Thr Leu Gln Val Phe Arg Lys Thr Ala Leu Leu Gly Ala Asn Gly Ala
                645                 650                 655

Gln Pro
```

STRA6 POLYPEPTIDES

CROSS REFERENCE TO RELATED APPLICATION

This application is a divisional of U.S. patent application Ser. No. 09/759,056, filed Jan. 11, 2001, now U.S. Pat. No. 7,173,115, which application claims priority under 35 U.S.C. §119(e) to U.S. Provisional Patent Application Ser. No. 60/228,914, filed Aug. 29, 2000, U.S. Provisional Patent Application Ser. No. 60/197,089, filed Apr. 14, 2000, and U.S. Provisional Patent Application Ser. No. 60/175,849, filed Jan. 13, 2000, the entire disclosure of these applications are hereby incorporated by reference.

FIELD OF THE INVENTION

The present invention relates generally to the identification and isolation of novel DNA and to the recombinant production of novel polypeptides having sequence similarity to murine Stra6, a retinoic acid responsive protein. Some of these molecules were earlier designated as "PRO10282", but will hereinafter also be referred to as "Stra6" polypeptides.

BACKGROUND OF THE INVENTION

Membrane-bound Proteins

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

The Stra6 polypeptides of the present invention share sequence homology (73% identity and 81% similarity) with the murine protein Stra6, whose expression is induced by retinoic acid (Bouillet et al., Dev. Biol. 170:420-433 [1995]; Bouillet et al., Mech. Dev. 63: 173-186 [1997]; Chazaud et al., Dev. Genet. 19: 66-73 [1996]). Since retinoic acid is an important signaling molecule during vertebrate development, the genes induced in response to retinoic acid are thought to play a crucial role in growth and differentiation during embryonic development. The murine Stra6 cDNA was isolated from P19 murine embyonal carcinoma cells using a subtractive hybridization approach designed to identify and isolate retinoic acid inducible genes, and does not show similarity with previously characterized proteins. It contains highly hydrophobic stretches of amino acid residues that correspond to multiple trans-membrane domains, a characteristic of a membrane integral protein. Based on its expression pattern, Stra6 is thought to play an important role in early dorsoventral limb patterning during embyonic development and later in the control of endochondral ossification (Chazaud et al., Dev. Genet. 19: 66-73 [1996]).

The Stra6 polypeptides disclosed herein contain multiple highly hydrophobic regions that likely constitute trans-membrane domains indicating that the Stra6 polypeptides are membrane integral proteins. They may function as receptors for an unknown ligand and may be a part of signal transduction pathway with impact on cell growth, development or differentiation.

Gene Amplification in Tumor Cells

Malignant tumors (cancers) are the second leading cause of death in the United States, after heart disease (Boring et al. CA Cancel J. Clin. 43:7 [1993]).

Cancer is characterized by an increase in the number of abnormal, or neoplastic cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites (metastasis). In a cancerous state, a cell proliferates under conditions in which normal cells would not grow. Cancer manifests itself in a wide variety of forms, characterized by different degrees of invasiveness and aggressiveness.

Alteration of gene expression is intimately related to the uncontrolled cell growth and de-differentiation, which are a common feature of all cancers. The genomes of certain well studied tumors have been found to show decreased expression of recessive genes, usually referred to as tumor suppression genes, which would normally function to prevent malignant cell growth, and/or overexpression of certain dominant genes, such as oncogenes, that act to promote malignant growth. Each of these genetic changes appears to be responsible for importing some of the traits that, in aggregate, represent the full neoplastic phenotype (Hunter, Cell, 64:1129 [1991] and Bishop, Cell, 64:235-248 [1991]).

A well-known mechanism of gene (e.g., oncogene) overexpression in cancer cells is gene amplification. This is a process where in the chromosome of the ancestral cell multiple copies of a particular gene are produced. The process involves unscheduled replication of the region of chromosome comprising the gene, followed by recombination of the replicated segments back into the chromosome (Alitalo et al., Adv. Cancer Res., 47:235-281 [1986]). It is believed that the overexpression of the gene parallels gene amplification, i.e., is proportionate to the number of copies made.

Proto-oncogenes that encode growth factors and growth factor receptors have been identified to play important roles in the pathogenesis of various human malignancies, including breast cancer. For example, it has been found that the human ErbB2 gene (erbB2, also known as her2, or c-erbB-2), which encodes a 185-kd transmembrane glycoprotein receptor (p185$^{HER2}$; HER2) related to the epidermal growth factor receptor EGFR), is overexpressed in about 25% to 30% of human breast cancer (Slamon et al., *Science*, 235:177-182 [1987]; Slamon et al., *Science*, 244:707-712 [1989]).

It has been reported that gene amplification of a proto-oncogene is an event typically involved in the more malignant forms of cancer, and could act as a predictor of clinical outcome (Schwab et al., *Genes Chromosomes Cancer*, 1:181-193 [1990]; Alitalo et al., supra). Thus, erbB2 overexpression is commonly regarded as a predictor of a poor prognosis, especially in patients with primary disease that involves axillary lymph nodes (Slamon et al., [1987] and [1989], supra; Ravdin and Chamness, *Gene*, 159:19-27 [1995]; and Hynes and Stern, *Biochim. Biophys. Acta*, 1198:165-184 [1994]), and has been linked to sensitivity and/or resistance to hormone therapy and chemotherapeutic regimens, including CMF (cyclophosphamide, methotrexate, and fluoruracil) and anthracyclines (Baselga et al., *Oncology*, 11 (3 Suppl I):43-48 [1997]). However, despite the association of erbB2 overexpression with poor prognosis, the odds of HER2-positive patients responding clinically to treatment with taxanes were greater than three times those of HER2-negative patients (Ibid). A recombinant humanized anti-ErbB2 (anti-HER2) monoclonal antibody (a humanized version of the murine anti-ErbB2 antibody 4D5, referred to as rhuMAb HER2 or Herceptin™) has been clinically active in patients with ErbB2-overexpressing metastatic breast cancers that had received extensive prior anticancer therapy. (Baselga et al., *J. Clin. Oncol.*, 14:737-744 [1996]).

In light of the above, there is obvious interest in identifying novel molecules, methods and compositions which are useful for diagnosing and treating tumors which are associated with gene amplification.

SUMMARY OF THE INVENTION

A human cDNA clone (designated herein as DNA 148380-2827) has been identified that has homology to nucleic acid encoding a murine retinoic acid responsive protein Stra6 and that encodes a 667 amino acid novel polypeptide, designated in the present application as full-length native-sequence human "PRO10282". An additional human cDNA clone (designated herein as DNA 148389-2827-1) has been identified that encodes a 658 amino acid novel polypeptide (PRO19578), showing significant sequence homology to both murine Stra6 and native sequence human PRO10282, which is believed to be an alternatively spliced variant of native sequence human PRO10282. As discussed hereinafter, in view of their homology with murine Stra6, the PRO10282 polypeptides of the present invention (including native sequence and variant molecules) will be also referred to as "Stra6" polypeptides.

In one embodiment, the invention provides an isolated nucleic acid molecule comprising a nucleotide sequence that encodes a PRO10282 polypeptide.

In one aspect, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule encoding a PRO10282 polypeptide having the sequence of amino acid residues from about 1 to about 667, inclusive, of FIG. 2 (SEQ ID NO:2), or (b) a DNA molecule encoding a PRO19578 polypeptide having the sequence of amino acid residues from about 1 to about 658, inclusive, of FIG. 7 (SEQ ID NO: 5), or (c) the complement of the DNA molecule of (a) or (b).

In another aspect, the isolated nucleic acid molecule comprises (a) a nucleotide sequence encoding a PRO10282 polypeptide having the sequence of amino acid residues from about 1 to about 667, inclusive, of FIG. 2 (SEQ ID NO:2), or (b) a nucleotide sequence encoding a PRO19578 polypeptide having the sequence of amino acid residues from about 1 to about 658, inclusive of FIG. 7 (SEQ ID NO: 5), or (c) the complement of the nucleotide sequence of (a) or (b).

In other aspects, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule having the sequence of nucleotides from about 49 to about 2049, inclusive, of FIG. 1 (SEQ ID NO:1), or (b) a DNA molecule having the sequence of nucleotides from about 186 to about 2159, inclusive, of FIG. 6 (SEQ ID NO: 4), or (c) the complement of the DNA molecule of (a) or (b).

In another aspect, the isolated nucleic acid molecule comprises (a) the nucleotide sequence of from about 49 to about 2049, inclusive, of FIG. 1 (SEQ ID NO:1), or (b) the nucleotide sequence of from about 186 to about 2159 of FIG. 6 (SEQ ID NO: 4), or (c) the complement of the nucleotide sequence of (a) or (b).

In a further aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule that encodes the same mature polypeptide encoded by the human protein cDNA deposited with the ATCC on Jan. 11, 2000 under ATCC Deposit No. PTA-1181 (DNA 148380-2827), (b) a DNA molecule that encodes the same mature polypeptide encoded by the human protein cDNA deposited with the ATCC on Feb. 23, 2000 under ATCC Deposit No. PTA-1405 (DNA148389-2827-1), or (c) the complement of the DNA molecule of (a) or (b). In a preferred embodiment, the isolated nucleic acid molecule comprises (a) a nucleotide sequence encoding the same mature polypeptide encoded by the human protein cDNA deposited with the ATCC on Jan. 11, 2000 under ATCC Deposit No. PTA-1181 (DNA148380-2827), (b) a nucleotide sequence encoding the same mature polypeptide encoded by the human protein cDNA deposited with the ATCC on Feb. 23, 2000 under ATCC Deposit No. PTA-1405 (DNA148389-2827-1), or (c) the complement of the nucleotide sequence of (a) or (b).

In another aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) the full-length polypeptide coding sequence of the human protein cDNA deposited with the ATCC on Jan. 11, 2000 under ATCC Deposit No. PTA-1181 (DNA148380-2827), (b) the full-length polypeptide coding sequence of the human protein cDNA deposited with the ATCC on Feb. 23, 2000 under ATCC No. PTA-1405 (DNA148389-2827-1), or (c) the complement of the nucleotide sequence of (a) or (b).

In a preferred embodiment, the isolated nucleic acid molecule comprises (a) the full-length polypeptide coding sequence of the DNA deposited with the ATCC on Jan. 11, 2000 under ATCC Deposit No. PT-1181 (DNA148380-2827), or (b) the full-length polypeptide coding sequence of the DNA deposited with the ATCC on Feb. 23, 2000 under ATCC Deposit No. PTA 1405 (DNA148389-2827-1), or (c) the complement of the nucleotide sequence of (a) or (b).

In another aspect, the invention concerns an isolated nucleic acid molecule which encodes an active PRO10282 polypeptide as defined below comprising a nucleotide sequence that hybridizes to the complement of a nucleic acid sequence that encodes amino acids 1 to about 667, inclusive, of FIG. 2 (SEQ ID NO:2), or to the complement of a nucleic acid sequence that encodes amino acids 1 to about 658, inclusive, of FIG. 7 (SEQ ID NO: 5), wherein the isolated nucleic acid molecule is other than DNA encoding murine Stra6. Preferably, hybridization occurs under high stringency (stringent) hybridization and wash conditions.

In yet another aspect, the invention concerns an isolated nucleic acid molecule which encodes an active PRO10282 polypeptide as defined below comprising a nucleotide sequence that hybridizes to the complement of the nucleic acid sequence between about nucleotides 49 and about 2049, inclusive, of FIG. 1 (SEQ ID NO: 1), or to the complement of the nucleic acid sequence between about nucleotides 186 to about 2159, inclusive, or FIG. 6 (SEQ ID NO: 4), wherein the isolated nucleic acid is other than DNA encoding murine Stra 6. Preferably, hybridization occurs under high stringency (stringent) hybridization and wash conditions.

In a further aspect, the invention concerns an isolated nucleic acid molecule having at least about 765 nucleotides and which is produced by hybridizing a test DNA molecule under stringent conditions with (a) a DNA molecule encoding a PRO10282 polypeptide having the sequence of amino acid residues from about 1 to about 667, inclusive, of FIG. 2 (SEQ ID NO:2), or (b) a DNA molecule encoding a PRO19578 polypeptide having the sequence of amino acid residues from about 1 to about 658, inclusive, of FIG. 7 (SEQ ID NO: 5), or (c) the complement of the DNA molecule of (a) or (b), and, if the test DNA molecule has at least about an 80% sequence identity, preferably at least about an 81% sequence identity, more preferably at least about an 82% sequence identity, yet more preferably at least about an 83% sequence identity, yet more preferably at least about an 84% sequence identity, yet more preferably at least about an 85% sequence identity, yet more preferably at least about an 86% sequence identity, yet more preferably at least about an 87% sequence identity, yet more preferably at least about an 88% sequence identity, yet more preferably at least about an 89% sequence identity, yet more preferably at least about a 90% sequence identity, yet more preferably at least about a 91% sequence identity, yet more preferably at least about a 92% sequence identity, yet more preferably at least about a 93% sequence identity, yet more preferably at least about a 94% sequence identity, yet more preferably at least about a 95% sequence identity, yet more preferably at least about a 96% sequence identity, yet more preferably at least about a 97% sequence identity, yet more preferably at least about a 98% sequence identity and yet more preferably at least about a 99% sequence identity to (a), (b) or (c), isolating the test DNA molecule.

In another aspect, the invention concerns an isolated nucleic acid molecule comprising a nucleotide sequence encoding a polypeptide scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with (a) the amino acid sequence of residues about 1 to 667, inclusive, of FIG. 2 (SEQ ID NO:2), or (b) the amino acid sequence of residues about 1 to about 658 of FIG. 7 (SEQ ID NO: 5), or (c) the complement of the nucleotide sequence of (a) or (b).

Another aspect the invention provides an isolated nucleic acid molecule comprising a nucleotide sequence encoding a PRO10282 polypeptide which is either transmembrane domain-deleted or transmembrane domain-inactivated, or is complementary to such encoding nucleotide sequence, wherein the transmembrane domains have been tentatively identified as extending from about amino acid position 54 to about amino acid position 69, about amino acid position 102 to about amino acid position 119, about amino acid position 148 to about amino acid position 166, about amino acid position 207 to about amino acid position 222, about amino acid position 301 to about amino acid position 320, about amino acid position 364 to about amino acid position 380, about amino acid position 431 to about amino acid position 451, about amino acid position 474 to about amino acid position 489 and about amino acid position 512 to about amino acid position 531 in the sequence of FIG. 2 (SEQ ID NO:2); and about amino acid position S4 to about amino acid position 71, about amino acid position 93 to about amino acid position 11, about amino acid position 140 to about amino acid position 157, about amino acid position 197 to about amino acid position 214, about amino acid position 291 to about amino acid position 312, about amino acid position 356 to about amino acid position 371, about amino acid position 425 to about amino acid position 481, about amino acid position 505 to about amino acid position 522 of FIG. 7 (SEQ ID NO: 5). Therefore, soluble extracellular domains of the herein described PRO10282 polypeptides are contemplated.

In this regard, another aspect of the present invention is directed to an isolated nucleic acid molecule which comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule encoding amino acids 1 to X of FIG. 2 (SEQ ID NO:2), where X is any amino acid from 49 to 59 of FIG. 2 (SEQ ID NO:2), or (b) the complement of the DNA molecule of (a). In a specific aspect, the isolated nucleic acid molecule comprises a nucleotide sequence which (a) encodes amino acids 1 to X of FIG. 2 (SEQ ID NO:2), or of FIG. 7 (SEQ ID NO: 5), where X is any amino acid from 49 to 59 of FIG. 2 (SEQ ID NO:2), or (b) is the complement of the DNA molecule of (a). In a specific aspect, the isolated nucleic acid molecule comprises a nucleotide sequence which (a) encodes amino acids 1 to X of FIG. 2 (SEQ ID NO: 2), or of FIG. 7 (SEQ ID NO: 5), where X is any amino acid from 49 to 59, inclusive, of FIG. 2 (SEQ ID NO: 2), or FIG. 7 (SEQ ID NO: 5), or (b) is the complement of the DNA molecule of (a).

In yet another aspect of the present invention, the isolated nucleic acid molecule (a) encodes a polypeptide scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues about 1 to X of FIG. 2 (SEQ ID NO:2), or of FIG. 7 (SEQ ID NO: 5), where X is any amino acid from 49 to 59 of FIG. 2 (SEQ ID NO:2), or (b) is the complement of the DNA molecule of (a).

Another embodiment is directed to fragments of a PRO10282 polypeptide coding sequence that may find use as, for example, hybridization probes or for encoding fragments of a PRO10282 polypeptide that may optionally encode a polypeptide comprising a binding site for an anti-PRO10282 antibody. Such nucleic acid fragments are usually at least about 20 nucleotides in length, preferably at least about 30 nucleotides in length, more preferably at least about 40 nucleotides in length, yet more preferably at least about 50 nucleotides in length, yet more preferably at least about 60 nucleotides in length, yet more preferably at least about 70 nucleotides in length, yet more preferably at least about 80 nucleotides in length, yet more preferably at least about 90 nucleotides in length, yet more preferably at least about 100 nucleotides in length, yet more preferably at least about 110 nucleotides in length, yet more preferably at least about 120 nucleotides in length, yet more preferably at least about 130 nucleotides in length, yet more preferably at least about 140 nucleotides in length, yet more preferably at least about 150 nucleotides in length, yet more preferably at least about 160 nucleotides in length, yet more preferably at least about 170 nucleotides, in length, yet more preferably at least about 180 nucleotides in length, yet more preferably at least about 190 nucleotides in length, yet more preferably at least about 200 nucleotides in length, yet more preferably at least about 250 nucleotides in length, yet more preferably at least about 300 nucleotides in length, yet more preferably at least about 350 nucleotides in length, yet more preferably at least about 400 nucleotides in length, yet more preferably at least about 450 nucleotides in length, yet more preferably at least about 500 nucleotides in length, yet more preferably at least about 600 nucleotides in length, yet more preferably at least about 700 nucleotides in length, yet more preferably at least about 800 nucleotides in length, yet more preferably at least about 900 nucleotides in length and yet more preferably at least about 1000 nucleotides in length, wherein in this context the term "about" means the referenced nucleotide sequence length plus or minus 10% of that referenced length. The nucleic acid fragments of the present invention are different from fragments of the native coding sequence of mouse Stra6. In a preferred embodiment, the nucleotide sequence fragment is derived from any coding region of the nucleotide sequence shown in FIG. 1 (SEQ ID NO:1), or of the nucleotide sequence shown in FIG. 6 (SEQ ID NO: 4). It is noted that novel fragments of a PRO10282 polypeptide-encoding nucleotide sequence may be determined in a routine manner by aligning the PRO10282 polypeptide-encoding nucleotide sequence with other known nucleotide sequences using any of a number of well known sequence alignment programs and determining which PRO10282 polypeptide-encoding nucleotide sequence fragment(s) are novel. All of such PRO10282 polypeptide-encoding nucleotide sequences are contemplated herein and can be determined without undue experimentation. Also contemplated are the PRO10282 polypeptide fragments encoded by these nucleotide molecule fragments, preferably those PRO10282 polypeptide fragments that comprise a binding site for an anti-PRO10282 antibody.

In another embodiment, the invention provides a vector comprising a nucleotide sequence encoding PRO10282 or its variants. The vector may comprise any of the isolated nucleic acid molecules hereinabove identified.

A host cell comprising such a vector is also provided. By way of example, the host cells may be CHO cells, *E. coli*, or yeast. A process for producing PRO10282 polypeptides is further provided and comprises culturing host cells under conditions suitable for expression of PRO10282 and recovering PRO10282 from the cell culture.

In another embodiment, the invention provides isolated PRO10282 polypeptide encoded by any of the isolated nucleic acid sequences hereinabove identified.

In a specific aspect, the invention provides isolated native sequence PRO10282 polypeptide, which in certain embodiments, includes an amino acid sequence comprising residues from about 1 to about 667 of FIG. 2 (SEQ ID NO:2), or residues from about 1 to about 658 of FIG. 7 (SEQ ID NO: 5).

In another aspect, the invention concerns an isolated PRO10282 polypeptide, comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to the sequence of amino acid residues from about 1 to about 667, inclusive, of FIG. 2 (SEQ ID NO:2), or to the sequence of amino acid residues from about 1 to about 658, inclusive, of FIG. 7 (SEQ ID NO: 5).

In a further aspect, the invention concerns an isolated PRO10282 polypeptide comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence encoded by the human protein cDNA deposited with the ATCC on Jan. 11, 2000 under ATCC Deposit No. PTA-1181 (DNA148380-2827), or to an amino acid sequence encoded by the human protein cDNA deposited with the ATCC on Feb. 23, 2000 under ATCC Deposit No. PTA 1405 (DNA14389-2827-1). In a preferred embodiment, the isolated PRO10282 polypeptide comprises an amino acid sequence encoded by the human protein cDNA deposited with the ATCC on Jan. 11, 2000 under ATCC Deposit No. PTA-1181 (DNA148380-2827), or by the human protein cDNA deposited with the A TCC on Feb. 23, 2000 under ATCC Deposit No. PTA 1405 (DNA 148389-2827-1).

In a further aspect, the invention concerns an isolated PRO10282 polypeptide comprising an amino acid sequence scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues from about 1 to about 667, inclusive, of FIG. 2 (SEQ ID NO:2), or with the amino acid sequence of residues from about 1 to about 659, inclusive, of FIG. 7 (SEQ ID NO: 5).

Another aspect the invention provides an isolated PRO10282 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO10282 polypeptide and recovering the PRO10282 polypeptide from the cell culture.

As such, one aspect of the present invention is directed to an isolated soluble PRO10282 polypeptide which comprises an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to amino acids 1 to X of FIG. 2 (SEQ ID NO:2), or of FIG. 7 (SEQ ID NO: 5), where X is any amino acid from 49 to 59 of FIG. 2 (SEQ ID NO:2), or of FIG. 7 (SEQ ID NO: 5). In a preferred aspect, the isolated soluble PRO10282 polypeptide comprises amino acids 1 to X of FIG. 2 (SEQ ID NO:2), or of FIG. 7 (SEQ ID NO: 5), where X is any amino acid from 49 to 59 of FIG. 2 (SEQ ID NO:2) or of FIG. 7 (SEQ ID NO: 5).

In yet another aspect of the present invention, the isolated soluble PRO10282 polypeptide comprises an amino acid sequence which scores at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of residues about 1 to X of FIG. 2 (SEQ ID NO:2), or of FIG. 7 (SEQ ID NO: 5), where X is any amino acid from 49 to 59 of FIG. 2 (SEQ ID NO:2) or of FIG. 7 (SEQ ID NO: 5).

In yet another aspect, the invention concerns an isolated PRO10282 polypeptide, comprising the sequence of amino acid residues from about 1 to about 667, inclusive, of FIG. 2 (SEQ ID NO:2), or of amino acid residues from about 1 to about 658, inclusive, of FIG. 7 (SEQ ID NO: 5), or a fragment thereof which is biologically active or sufficient to provide a binding site for an anti-PRO10282 antibody, wherein the identification of PRO10282 polypeptide fragments that possess biological activity or provide a binding site for an anti-PRO10282 antibody may be accomplished in a routine manner using techniques which are well known in the art. The fragment herein is other than a fragment of a mouse Stra6 polypeptide. Preferably, the PRO10282 fragment retains a qualitative biological activity of a native PRO10282 polypeptide.

In a still further aspect, the invention provides a polypeptide produced by (i) hybridizing a test DNA molecule under stringent conditions with (a) a DNA molecule encoding a PRO10282 polypeptide having the sequence of amino acid residues from about 1 to about 667, inclusive, of FIG. 2 (SEQ ID NO:2), or (b) a DNA molecule encoding a PRO19578 polypeptide having the sequence of amino acid residues from about 1 to about 658, inclusive, of FIG. 7 (SEQ ID NO: 5), or (c) the complement of the DNA molecule of (a) or (b), and if the test DNA molecule has at least about an 80% sequence identity, preferably at least about an 81% sequence identity, more preferably at least about an 82% sequence identity, yet more preferably at least about an 83% sequence identity, yet more preferably at least about an 84% sequence identity, yet more preferably at least about an 85% sequence identity, yet more preferably at least about an 86% sequence identity, yet more preferably at least about an 87% sequence identity, yet more preferably at least about an 88% sequence identity, yet more preferably at least about an 89% sequence identity, yet more preferably at least about a 90% sequence identity, yet more preferably at least about a 91% sequence identity, yet more preferably at least about a 92% sequence identity, yet, more preferably at least about a 93% sequence identity, yet more preferably at least about a 94% sequence identity, yet more preferably at least about a 95% sequence identity, yet more preferably at least about a 96% sequence identity, yet more preferably at least about a 97% sequence identity, yet more preferably at least about a 98% sequence identity and yet more preferably at least about a 99% sequence identity to (a), (b) or (c), (ii) culturing a host cell comprising the test DNA molecule under conditions suitable for expression of the polypeptide, and (iii) recovering the polypeptide from the cell culture.

In another embodiment, the invention provides chimeric molecules comprising a PRO10282 polypeptide fused to a heterologous polypeptide or amino acid sequence, wherein the PRO10282 polypeptide may comprise any PRO10282 polypeptide, variant or fragment thereof as hereinbefore described. An example of such a chimeric molecule comprises a PRO10282 polypeptide fused to an epitope tag sequence or a Fc region of an immunoglobulin.

In another embodiment, the invention provides an antibody as defined below which specifically binds to a PRO10282 polypeptide as hereinbefore described. Optionally, the antibody is a monoclonal antibody, an antibody fragment or a single chain antibody.

In yet another embodiment, the invention concerns agonists and antagonists of a native PRO10282 polypeptide as defined below. In a particular embodiment, the agonist or antagonist is an anti-PRO10282 antibody or a small molecule.

In a further embodiment, the invention concerns a method of identifying agonists or antagonists to a PRO10282 polypeptide which comprise contacting the PRO10282 polypeptide with a candidate molecule and monitoring a biological activity mediated by said PRO10282 polypeptide. Preferably, the PRO10282 polypeptide is a native PRO10282 polypeptide.

In a still further embodiment, the invention concerns a composition of matter comprising a PRO10282 polypeptide, or an agonist or antagonist of a PRO10282 polypeptide as herein described, or an anti-PRO10282 antibody, in combination with a carrier. Optionally, the carrier is a pharmaceutically acceptable carrier.

Another embodiment of the present invention is directed to the use of a PRO10282 polypeptide, or an agonist or antagonist thereof as herein described, or an anti-PRO10282 antibody, for the preparation of a medicament useful in the treatment of a condition which is responsive to the PRO10282 polypeptide, an agonist or antagonist thereof or an anti-PRO10282 antibody.

In a further aspect, the invention concerns an antibody which specifically binds to a PRO10282 polypeptide. The antibody preferably induces the death of a cell that expresses the PRO10282 polypeptide. In a particularly preferred embodiment, the cell is a cancer cell that overexpresses a PRO10282 polypeptide as compared to a normal cell of the same tissue type. The antibody preferably is humanized or human, and includes antibody fragments and single-chain antibodies.

In another aspect, the invention concerns a composition of matter comprising an antibody specifically binding to a PRO10282 polypeptide.

In yet another aspect, the invention concerns an isolated nucleic acid molecule encoding an antibody specifically binding to a PRO10282 polypeptide, a vector comprising such nucleic acid, and a host cell comprising such vector. The invention also concerns a method for producing anti-PRO10282 antibodies.

In a still further embodiment, the invention concerns a method for determining the presence of a PRO10282 polypeptide in a sample suspected of containing such polypeptide by exposing the sample to an anti-PRO10282 antibody (or another antagonist of PRO10282), and determining the binding of such antibody (or antagonist) to the PRO10282 polypeptide in the sample. In a particularly important embodiment, the sample is from a cancer cell.

In a different embodiment, the invention concerns a method of diagnosing tumor in a mammal, comprising detecting the level of expression of a gene encoding a PRO10282 polypeptide (a) in a test sample of tissue obtained from the mammal, and (b) in a control sample of known normal tissue cells of the same cell type. Higher expression level in the test sample, as compared to the control sample, indicates the presence of tumor in the mammal from which the test tissue cells were taken.

According to another method of the invention, tumor is diagnosed in a mammal by (a) contacting an anti-PRO10282 antibody with a test sample of tissue cells obtained from the mammal, and (b) detecting the formation of a complex between the antibody and a PRO10282 polypeptide in the test sample. Formation of a complex is indicative of the presence of a tumor in the mammal.

In another aspect, the invention concerns a cancer diagnostic kit comprising an anti-PRO10282 antibody (or a different antagonist of PRO10282) and a carrier in suitable packaging. Optionally, the kit also contains instructions for using the antibody or other antagonist to detect the presence of a PRO10282 polypeptide in a sample.

In yet another aspect, the invention concerns a method of inhibiting the growth of tumor cells by exposing tumor cells that express a PRO10282 polypeptide to an effective amount of an agent that inhibits a biological activity of the PRO10282 polypeptide, thereby inhibiting the growth of tumor cells. The agent may, for example, be an anti-PRO10282 antibody or another antagonist of PRO10282. The tumor cells may be further exposed to conventional tumor treatments, such as radiation treatment, treatment with a cytotoxic agent and/or chemotherapeutic agent, etc.

In a different aspect, the invention concerns a method of inhibiting the growth of tumor cells by exposing tumor cells that express a PRO10282 polypeptide to an effective amount of an agent that inhibits the expression of the polypeptide, thereby inhibiting tumor growth.

The invention further concerns analogous methods to prevent or slow down (lessen) the development, growth, or spread of tumor characterized by the overexpression of a PRO10282 polypeptide. Such treatment may directly decrease the pathology of tumor cells, or render the tumor cells more susceptible to treatment by other therapeutic agents, e.g., radiation and/or chemotherapy. The invention specifically includes methods that control abnormal or otherwise metastasis, interference with the normal functioning of neighboring cells, release of cytokines or other secretory products at abnormal levels, suppression or aggravation of inflammatory or immunological response, etc.

The invention further concerns articles of manufacture comprising a container, a label on a container, and a composition comprising an active agent, where the composition is effective for inhibiting tumor growth and the label on the container indicates that the composition is effective for treating a condition characterized by overexpression of a PRO10282 polypeptide in tumor cells.

In a still further aspect, the invention concerns a method of identifying a compound that inhibits the biological or immunological activity of a PRO10282 polypeptide, by contacting a candidate compound with a PRO10282 polypeptide under conditions and for a time sufficient to allow the two components to interact, and determining whether a biological or immunological activity of the PRO10282 polypeptide is inhibited.

In yet another aspect, the invention concerns a method of identifying a compound that inhibits an activity of a PRO10282 polypeptide, comprising the following steps: (a) contacting cells and a candidate compound to be screened in the presence of a PRO10282 polypeptide under conditions suitable for the induction of a cellular response normally induced by a PRO10282 polypeptide and (b) determining the induction of said cellular response to determine if the test compound is an effective antagonist. The lack of induction of a cellular response indicates that the test compound is an effective antagonist.

The invention further concerns a method for identifying a compound that inhibits the expression of a PRO10282 polypeptide in cells expressing it, by contacting the cells with a candidate compound and determining whether the expression is inhibited.

The invention specifically concerns PRO10282 agonists and antagonists identified by the screening methods herein. Such agonists and antagonists include, without limitation, anti-PRO10282 antibodies, polypeptides, peptides, and small organic molecules with agonist or antagonist properties.

BRIEF DESCRIPTION OF THE DRAWINGS

FIG. 1 shows the nucleotide sequence (SEQ ID NO:1) of a cDNA containing a nucleotide sequence (nucleotides 1-2732) encoding native sequence PRO10282, wherein the nucleotide sequence (SEQ ID NO:1) is a clone designated herein as "DNA 148380-2827." Also presented in bold font and underlined are the positions of the respective start and stop codons.

FIG. 2 shows the amino acid sequence (SEQ ID NO:2) of a native sequence PRO10282 polypeptide as derived from the coding sequence of SEQ ID NO:1. Also shown are the approximate locations of various other important polypeptide domains.

FIGS. 3A-D show hypothetical exemplifications for using the below described method to determine % amino acid sequence identity (FIGS. 3A-B) and % nucleic acid sequence identity (FIGS. 3C-D) using the ALIGN-2 sequence comparison computer program, wherein "PRO" represents the amino acid sequence of a hypothetical PRO10282 polypeptide of interest, "Comparison Protein" represents the amino acid sequence of a polypeptide against which the "PRO" polypeptide of interest is being compared, "PRO-DNA" represents a hypothetical PRO10282-encoding nucleic acid sequence of interest, "Comparison DNA" represents the nucleotide sequence of a nucleic acid molecule against which the "PRO-DNA" nucleic acid molecule of interest is being compared, "X," "Y" and "Z" each represent different hypothetical amino acid residues and "N". "L" and "V" each represent different hypothetical nucleotides.

FIGS. 4A-Q provide the complete source code for the ALIGN-2 sequence comparison computer program. This source code may be routinely compiled for use on a UNIX operating system to provide the ALIGN-2 sequence comparison computer program.

FIG. 5 shows a nucleotide sequence designated herein as DNA 100038 (SEQ ID NO:3).

FIG. 6 shows the nucleotide sequence (SEQ ID NO: 4) of a cDNA containing a nucleotide sequence (nucleotides 1-2778) encoding a native sequence human Stra6 polypeptide variant, wherein the nucleotide sequence (SEQ ID NO:4) is a clone designated herein as "DNA148389-2827-1." Also presented in bold font and underlined are the positions of the respective start and stop codons.

FIG. 7 shows the amino acid sequence (SEQ ID NO:5) of a native sequence human Stra6 polypeptide variant as derived from the coding sequence of SEQ ID NO:4. Also shown are the approximate locations of various other important polypeptide domains.

FIG. 8 is a schematic representation of mouse Stra6, and the human Stra6 protein encoded by DNA 148380-2827 (native human PRO10282).

FIG. 9 shows the hydrophobicity plot of the native sequence human Stra6 protein encoded by DNA 148380-2827 (native human PRO10282).

FIG. 10 shows the relative RNA expression profile for the native sequence human Stra 6 protein encoded by DNA 148380-2827 in various normal human tissues.

FIG. 11 shows the RNA fold expression for the native sequence human Stra6 protein encoded by DNA 148380-2827 in human colon tumor tissue relative to RNA expression in normal mucose from the same patient assayed by quantitative PCR. The data are from one experiment done in triplicate. The experiment was repeated at least twice with a different set of PCR primers.

FIG. 12A shows the RNA expression for the native sequence human Stra6 protein encoded by DNA 148380-2827 in human colon tissue relative to RNA expression in normal mucose from the same patient, using the housekeeping gene, GAPDH as a control.

FIG. 12B shows the localization of Stra6 to the epithelial tumor cells in a colon adenocarcinoma by in situ hybridization.

FIG. 13 shows the RNA expression for the native human Stra6 protein encoded by DNA 148380-2827 in human breast, kidney, colon and lung tumor cell lines, relative to corresponding normal cell lines.

FIG. 14 illustrates the expression of peptide fragments derived from the native sequence human Stra 6 protein encoded by DNA 148380-2827 in *E. coli*.

FIG. 15 illustrates Stra6 RNA expression in human colon carcinoma cells in the presence and absence of all-trans-retinoic acid (ATRA) and 9-cis-retinoic acid (9cRA), respectively.

FIG. 16 In situ hybridization for Stra6 in tumor sections. Darkfield images demonstrating silver grains (A, C, E, G) are shown with corresponding hematoxylin/eosin-stained brightfield images (B, D, F, H). Moderate densities of silver grains overlie tumor cells but not a blood vessel in a malignant melanoma (A, B). Neoplastic epithelium in an endometrial adenocarcinoma is moderately labeled whereas tumor stroma is negative (C, D). Blastemal regions in a Wilm's tumor display high expression levels whereas tumor stroma is negative (E, F). A pheochromocytoma shows very high Stra6 mRNA expression while adjacent normal adrenal cortex is negative (G, H). Scale bars= 100 microns.

FIG. 17 (A) Induction of Stra6 mRNA expression in response to 9-m-RA or all-trans-RA in C57MG/Parent and C57MG/Wnt-1 cells. (B) Induction of Stra6 mRNA expression in C57MG/Parent cells in response to Wnt-3A conditioned media and 9-m-RA. (C) Induction of Stra6 mRNA expression after retinoic acid treatment in HCT116 and WiDr colon adenocarcinoma cells. (D) Darkfield images demonstrating Stra6 expression by in situ hybridization in HCT116 cells before (top panel) and after (lower panel) treatment with retinoic acid. (E) Stra6 protein expression in WiDr cells before (−RA) and after (+RA) treatment with retinoic acid as visualized by Western blot with a monoclonal antibody directed against human Stra6 peptide B. (F) Stra6 membrane localization in WiDr cells untreated (left panel) or treated (right panel) with retinoic acid. Immunohistochemistry was performed with an anti-human Stra6 peptide B monoclonal hybridoma culture supernatant (clone 12F4.2H9.1D5). For the experiments shown in A-F, cells were treated with retinoic acid for 48 hours. Stra6 products obtained after completion of the quantitative PCR reactions (40 cycles each) are shown below each graph A-C.

FIG. 18 (A) Wnt-1 induces RARγ-1 expression. Protein-equivalent amounts of whole cell lysate from tetracycline repressible C57MG/Wnt-1 cells in the absence of tetracycline for 0, 24, 48, or 72 hours, were subjected to SDS-PAGE and immunoblotted for RARγ-1 and ERK2. (B) RARγ-1 mRNA expression in hyperplastic mammary glands and mammary gland tumors from Wnt-1 transgenic mice. mRNA expression was determined by quantitative RT-PCR and the data are expressed as fold expression relative to mRNA expression in wild-type mammary glands.

DETAILED DESCRIPTION OF THE PREFERRED EMBODIMENTS

I. Definitions

The terms "PRO10282 polypeptide", "PRO10282 protein", "PRO10282", "Stra6 polypeptide", "Stra6 protein" and "Stra6" are used interchangeably, and encompass native sequence PRO10282 (Stra6) and PRO10282 (Stra6) polypeptide variants (which are further defined herein). The PRO10282 (Stra6) polypeptide may be isolated from a variety of sources, such as from human tissue types or from another source, or prepared by recombinant and/or synthetic methods.

A "native sequence PRO10282" or "native sequence Stra6" comprises a polypeptide having the same amino acid sequence as a PRO10282 derived from nature. Such native sequence PRO10282 (Stra6) can be isolated from nature or can be produced by recombinant and/or synthetic means. The term "native sequence PRO10282" or "native sequence Stra6" specifically encompasses naturally-occurring truncated or secreted forms (e.g., an extracellular domain sequence), naturally-occurring variant forms (e.g., alternatively spliced forms) and naturally-occurring allelic variants of the PRO10282. In one embodiment of the invention, the native sequence PRO10282 is a mature or full-length native sequence PRO10282 comprising amino acids 1 to 667 of FIG. 2 (SEQ ID NO:2). In another embodiment of the invention, the native sequence PRO10282 polypeptide is a mature or full-length PRO19578 polypeptide comprising amino acids 1 to 658 of SEQ ID NO: 5, which is believed to be an alternatively spliced form of the native sequence PRO10282 polypeptide of SEQ ID NO: 2. Also, while the PRO10282 polypeptides disclosed in FIG. 2 (SEQ ID NO:2) and in FIG. 7, SEQ ID NO: 5 are shown to begin with the methionine residue designated herein as amino acid position 1, it is conceivable and possible that another methionine residue located either upstream or downstream from amino acid position 1 in FIG. 2 (SEQ ID NO:2) or in FIG. 7 (SEQ ID NO. 5) may be employed as the starting amino acid residue for the PRO10282 polypeptide.

The PRO10282 (Stra6) polypeptide "extracellular domain" or "ECD" refers to a form of the PRO10282 (Stra6) polypeptide which is essentially free of the transmembrane and cytoplasmic domains. Ordinarily, a PRO10282 polypeptide ECD will have less than about 1% of such transmembrane and/or cytoplasmic domains and preferably, will have less than about 0.5% of such domains. It will be understood that any transmembrane domain(s) identified for the PRO10282 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified. As such, in one embodiment of the present invention, the extracellular domain of a PRO10282 polypeptide comprises amino acids 1 to X, wherein X is any amino acid from amino acid 49 to 59 of FIG. 2 (SEQ ID NO:2) or of FIG. 7 (SEQ ID NO: 5).

"PRO10282 variant polypeptide" or "Stra6 variant polypeptide", which terms are used interchangeably, means an active PRO10282 (Stra6) polypeptide as defined below having at least about 80% amino acid sequence identity with the amino acid sequence of (a) residues 1 to 667 of the PRO10282 polypeptide shown in FIG. 2 (SEQ ID NO:2), or residues 1 to 658 of FIG. 7 (SEQ ID NO: 5), (b) 1 to X of FIG. 2 (SEQ ID NO:2) or FIG. 7 (SEQ ID NO: 5), wherein X is any amino acid from amino acid 49 to amino acid 59 of FIG. 2 (SEQ ID NO:2) or of FIG. 7 (SEQ ID NO: 5), or (c) another specifically derived fragment of the amino acid sequence shown in FIG. 2 (SEQ ID NO:2), or FIG. 7 (SEQ ID NO: 5). Such PRO10282 (Stra6) variant polypeptides include, for instance, PRO10282 (Stra6) polypeptides wherein one or more amino acid residues are added, or deleted, at the N- and/or C-terminus, as well as within one or more internal domains, of the sequence of FIG. 2 (SEQ ID NO:2) or FIG. 7 (SEQ ID NO: 5). Ordinarily, a PRO10282 variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% ammo acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with (a) residues 1 to 667 of the PRO10282 polypeptide shown in FIG. 2 (SEQ ID NO:2) or residues 1 to 658 of the PRO19578 polypeptide of FIG. 7 (SEQ ID NO: 5), (b) 1 to X of FIG. 2 (SEQ ID NO:2) or FIG. 7 (SEQ ID NO: 5), wherein X is any amino acid from amino acid 49 to amino acid 59 of FIG. 2 (SEQ ID NO:2) or FIG. 7 (SEQ ID NO: 5), or (c) another specifically derived fragment of the amino acid sequence shown in FIG. 2 (SEQ ID NO:2) or FIG. 7 (SEQ ID NO: 5). PRO10282 variant polypeptides do not encompass the native PRO10282 polypeptide sequence. Ordinarily, PRO10282 variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 250 amino acids in length, more often at least about 300 amino acids in length, or more, and are different from fragments of the murine Stra6 sequence, as disclosed in Bouillet et al., *Mechanisms of Development* 63, 173-186 (1997).

"Percent (%) amino acid sequence identity" with respect to the PRO10282 (Stra6) polypeptide sequences identified herein is defined as the percentage of amino acid residues in a candidate sequence that are identical with the amino acid residues in a PRO10282 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2. ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in FIGS. 4A-Q. The ALIGN-2 sequence comparison computer program was authored by Genentech, Inc. and the source code shown in FIGS. 4A-Q has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in FIGS. 4A-Q. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations, FIGS. 3A-B demonstrate how to calculate the % amino acid sequence identity of the amino acid sequence designated "Comparison Protein" to the amino acid sequence designated "PRO".

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.* 25:3389-3402 (1997)). The NCB1-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO10282 (Stra6) variant polynucleotide" or "PRO10282 (Stra6) variant nucleic acid sequence" means a nucleic acid molecule which encodes an active PRO10282 polypeptide as defined below and which has at least about 80% nucleic acid sequence identity with either (a) a nucleic acid sequence which encodes residues 1 to 667 of the PRO10282 polypeptide shown in FIG. 2 (SEQ ID NO:2), or residues 1 to 658 of FIG. 7 (SEQ ID NO: 5), (b) a nucleic acid sequence which encodes amino acids 1 to X of FIG. 2 (SEQ ID NO:2) or FIG. 7 (SEQ ID NO: 5), wherein X is any amino acid from amino acid 49 to amino acid 59 of FIG. 2 (SEQ ID NO:2) or of FIG. 7 (SEQ ID NO: 5), or (c) a nucleic acid sequence which encodes another specifically derived fragment of the amino acid sequence shown in FIG. 2 (SEQ ID NO:2) or in FIG. 7 (SEQ ID NO: 5). Ordinarily, a PRO10282 variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about > 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with either (a) a nucleic acid sequence which encodes residues 1 to 667 of the PRO10282 polypeptide shown in FIG. 2 (SEQ ID NO:2), or residues 1 to 658 of the PRO19678 polypeptide shown in FIG. 7 (SEQ ID NO: 5), (b) a nucleic acid sequence which encodes amino acids 1 to X of FIG. 2 (SEQ ID NO:2) or of FIG. 7 (SEQ ID NO: 5), wherein X is any amino acid from amino acid 49 to amino acid 59 of FIG. 2 (SEQ ID NO:2) or FIG. 7 (SEQ ID NO: 5), or (c) a nucleic acid sequence which encodes another specifically derived fragment of the amino acid sequence shown in FIG. 2 (SEQ ID NO:2) or in FIG. 7 (SEQ ID NO: 5). PRO10282 polynucleotide variants do not encompass the native PRO10282 nucleotide sequence, or the native PRO19578 nucleotide sequence.

Ordinarily, PRO10282 (Stra6) variant polynucleotides are at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more, and specifically exclude polynucleotides that are included in the nucleotide sequence of murine Stra6, as disclosed in Bouillet et al., *Mechanisms of Development* 63, 173-186 (1997).

"Percent (%) nucleic acid sequence identity" with respect to the PRO10282 (Stra6) polypeptide-encoding nucleic acid sequences identified herein is defined as the percentage of nucleotides in a candidate sequence that are identical with the nucleotides in a PRO10282 polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST 2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % nucleic acid sequence identity values are obtained as described below by using the sequence comparison computer program ALIGN-2, wherein the complete source code for the ALIGN-2 program is provided in FIGS. 4A-Q. The ALIGN-2 sequence comparison computer program was authored by Genentech, Inc. and the source code shown in FIGS. 4A-Q has been filed with user documentation in the U.S. Copyright Office, Washington D.C., 20559, where it is registered under U.S. Copyright Registration No.

TXU510087. The ALIGN-2 program is publicly available through Genentech, Inc., South San Francisco, Calif. or may be compiled from the source code provided in FIGS. 4A-Q. The ALIGN-2 program should be compiled for use on a UNIX operating system, preferably digital UNIX V4.0D. All sequence comparison parameters are set by the ALIGN-2 program and do not vary.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, FIGS. 3C-D demonstrate how to calculate the % nucleic acid sequence identity of the nucleic acid sequence designated "Comparison DNA" to the nucleic acid sequence designated "PRO-DNA".

Unless specifically stated otherwise, all % nucleic acid sequence identity values used herein are obtained as described above using the ALIGN-2 sequence comparison computer program. However, % nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO10282 (Stra6) variant polynucleotides are nucleic acid molecules that encode an active PRO10282 polypeptide and which are capable of hybridizing, preferably under stringent hybridization and wash conditions, to nucleotide sequences encoding the full-length PRO10282 polypeptides shown in FIG. 2 (SEQ ID NO:2) or FIG. 7 (SEQ ID NO: 5). PRO10282 variant polypeptides may be those that are encoded by a PRO10282 variant polynucleotide.

The term "positives", in the context of the amino acid sequence identity comparisons performed as described above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 1 below) of the amino acid residue of interest.

For purposes herein, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Preferably, the isolated polypeptide is free of association with all components with which it is naturally associated. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO10282 (Stra6) natural environment will not be present. Ordinarily, however, isolated polypeptide will be prepared by at least one purification step.

An "isolated" nucleic acid molecule encoding a PRO10282 (Stra6) polypeptide is a nucleic acid molecule that is identified and separated from at least one contaminant nucleic acid molecule with which it is ordinarily associated in the natural source of the PRO10282-encoding nucleic acid. Preferably, the isolated nucleic is free of association with all components with which it is naturally associated. An isolated PRO10282-encoding nucleic acid molecule is other than in the form or setting in which it is found in nature. Isolated nucleic acid molecules therefore are distinguished from the PRO10282-encoding nucleic acid molecule as it exists in natural cells. However, an isolated nucleic acid molecule encoding a PRO10282 (Stra6) polypeptide includes PRO10282-encoding nucleic acid molecules contained in cells that ordinarily express PRO10282 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include, a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO10282 monoclonal antibodies (including agonist, antagonist, and neutralizing antibodies), anti-PRO10282 antibody compositions with polyepitopic specificity, single chain anti-PRO10282 antibodies, and fragments of antPPRO10282 antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO10282 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

The term "antibody" is used in the broadest sense and specifically covers, for example, single anti-PRO10282 (anti-Stra6) monoclonal antibodies (including agonist, antagonist, and neutralizing antibodies), anti-PRO10282 antibody compositions with polyepitopic specificity, single chain anti-PRO10282 antibodies, and fragments of anti-PRO10282 antibodies (see below).

The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen binding or variable region of the intact antibody. Examples of antibody fragments include Fab, Fab', F(ab'), and Fv fragments; diabodies; linear antibodies (Zapata et al., *Protein Eng.*, 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment, which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa ( ) and lambda ( ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the difference classes of immunoglobulins are called α, δ, ε, γ, and μ, respectively. The subunit structures and three-dimensional configurations of difference classes of immunoglobulins are well known.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR) regions.

The variable domains of native heavy and light chains each comprise four FR regions, largely adopting a -sheet configuration, connected by three CDRs, which form loops connecting, and in some cases forming part of the sheet structure. The CDRs in each chain are held together in close proximity by the FR regions and, with the CDRs from the other chain, contribute to the formation of the antigen-binding site of antibodies (see Kabat et al., *NIH Publ. No.* 91-3242, Vol. 1, pages 647-669 (1991)). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institute of Health, Bethesda, Md. [1991]) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Clothia and Lesk, *J. Mol. Biol.*, 196: 901-917 [1987]). "Framework" or "FR" residues are those variable domain residues other than the hypervariable region residues as herein defined.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see, Jones et. al., *Nature*, 321:522-525 (1986); Reichmann et al., *Nature*, 332:323-329 [1988]; and Presta, *Curr. Op. Struct. Biol.*, 2:593-596 (1992). The humanized antibody includes a PRIMATIZED™ antibody wherein the antigen-binding region of the antibody is derived from an antibody produced by immunizing macaque monkeys with the antigen of interest.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of PRO10282 which retain a biological and/or an immunological activity of native or naturally-occurring PRO10282, wherein "biological" activity refers to a biological function (either inhibitory or stimulatory) caused by a native or naturally-occurring PRO10282 other than the ability to induce the production of an antibody against an antigenic epitope possessed by a native or naturally-occurring PRO10282 and an "immunological" activity refers to the ability to induce the production of an antibody against an antigenic epitope possessed by a native or naturally-occurring PRO10282. A preferred biological activity includes, for example, a role in growth, development or differentiation in response to retinoic acid. Based on close similarity with Stra6, a murine protein induced in response to retinoic acid, PRO10282 polypeptide disclosed herein may play an important role, for example, in early dorsoventral limb patterning and later in the control of endochondral ossification. Another biological activity is involvement in tumor development and growth.

"Immunological activity" preferably is "immunological cross-reactivity," which is used to mean that the candidate polypeptide is capable of competitively inhibiting the qualitative biological activity of a PRO10282 (Stra6) polypeptide having this activity with polyclonal antisera raised against the known active PRO10282 (Stra6) polypeptide. Such antisera are prepared in conventional fashion by injecting goats or rabbits, for example, subcutaneously with the known active analogue in complete Freund's adjuvant, followed by booster intraperitoneal or subcutaneous injection in incomplete Freund's. The immunological cross-reactivity is preferably "specific", which means that the binding affinity of the immunologically cross-reactive molecule (e.g. antibody) identified, to the corresponding Stra6 polypeptide is significantly higher (preferably at least about 2-times, more preferably at least about 4-times, even more preferably at least about 8-times, most preferably at least about 10-times higher) than the binding affinity of that molecule to any other known native polypeptide.

The term "antagonist" is used in the broadest sense, and includes any molecule that partially or fully blocks, inhibits, or neutralizes a biological activity of a native PRO10282 polypeptide disclosed herein. In a similar manner, the term "agonist" is used in the broadest sense and includes any molecule that mimics a biological activity of a native PRO10282 polypeptide disclosed herein. Suitable agonist or antagonist molecules specifically include agonist or antagonist antibodies or antibody fragments, fragments or amino acid sequence variants of native PRO10282 polypeptides, peptides, small organic molecules, etc. Methods for identifying agonists or antagonists of a PRO10282 polypeptide may comprise contacting a PRO10282 polypeptide with a candidate agonist or antagonist molecule and measuring a detectable change in one or more biological activities normally associated with the PRO10282 polypeptide.

"Tumor", as used herein, refers to all neoplastic cell growth and proliferation, whether malignant or benign, and all precancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PROT0282 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

The phrases "gene amplification" and "gene duplication" are used interchangeably and refer to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhone-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al., (WB Saunders: Philadelphia, 1995), especially p. 13.

"Doxorubicin" is an anthracycline antibiotic. The full chemical name of doxorubicin is (8S-cis)-10-[(3-amino-2,3, 6-trideoxy-1-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is generic term for proteins released by one cell population which act on another cell as intercellular mediators. Examples of such cytokines are lymphokines. monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon -α, -β, and -γ, colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL).

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy", *Biochemical Society Transactions*, 14:375-382, 615th Meeting, Belfast (1986), and Stella et al., "Prodrugs: A Chemical Approach to Targeted Drug Delivery", *Directed Drug Delivery*, Borchardt et al., (ed.), pp. 147-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glysocylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrugs form for use in this invention include, but are not limited to, those chemotherapeutic agents described above.

An "effective amount" of a polypeptide disclosed herein or an antagonist thereof, in reference to inhibition of neoplastic cell growth, tumor growth or cancer cell growth, in an amount capable of inhibiting, to some extent, the growth of target cells. The term includes an amount capable of invoking a growth inhibitory, cytostatic and/or cytotoxic effect and/or apoptosis of the target cells. A "therapeutically effective amount" of a PRO10282 polypeptide antagonist for purpose of treatment of tumor may be determined empirically and in a routine manner.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder. A "therapeutically effective amount" of a PRO10282 polypeptide antagonist for purpose of treatment of tumor may be determined empirically and in a routine manner.

A "growth inhibitory amount" of a PRO10282 antagonist is an amount capable of inhibiting the growth of a cell, especially tumor, e.g. cancer cell, either in vitro or in vivo. A "cytotoxic amount" of a PRO10282 antagonist for purposes of inhibiting neoplastic cell growth may be determined empirically and in a routine manner.

A "cytotoxic amount" or a PRO10282 antagonist is an amount capable of causing the destruction of a cell, especially tumor, e.g. cancer cell, either in vitro or in vivo. A "cytotoxic amount" of a PRO10282 antagonist for purposes of inhibiting neoplastic cell growth may be determined empirically and in a routine manner.

"Antisense oligodeoxynucleotides" or "antisense oligonucleotides" (which terms are used interchangeably) are defined as nucleic acid molecules that can inhibit the transcription and/or translation of target genes in a sequence-specific manner. The tern "antisense" refers to the fact that the nucleic acid is complementary to the coding ("sense") genetic sequence of the target gene. Antisense oligonucleotides hybridize in an antiparallel orientation to nascent mRNA through Watson-Crick base-pairing. By binding the target mRNA template, antisense oligonucleotides block the successful translation of the encoded protein. The term specifically includes antisense agents called "ribozomes" that have been designated to induce catalytic cleavage of a target RNA by addition of a sequence that has natural self-splicing activity (Warzocha and Wotowiec, "Antisense strategy" biological utility and prospects in the treatment of hematological malignancies." *Leuk. Lymphoma* 24:267-281 [1997]).

II. Compositions and Methods of the Invention

A. Full-length Native Sequence Human PRO10282 and PRO 19578 (Stra6) Polypeptides The present invention provides newly identified and isolated nucleotide sequences encoding polypeptides referred to in the present application as native sequence human PRO10282 (or also UNQ3126) and PRO19578, respectively. In particular, cDNA encoding the native human PRO10282 and PRO19578 polypeptides has been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by DNA 148380-2827 as well as all further native homologues and variants included in the foregoing definition of PRO10282, will be referred to as "PRO10282", regardless of their origin or mode of preparation. The polypeptide encoded by DNA 148389-2827-1, which is a native variant of "PRO10282," will be specifically referred to as "PRO19578."

As disclosed in the Examples below, cDNA clones designated herein as DNA 148380-2827 and DNA 148389-2827-1 have been deposited with the ATCC. The actual nucleotide sequence of the clone can readily be determined by the skilled artisan by sequencing of the deposited clone using routine methods in the art. The predicted amino acid sequence can be determined from the nucleotide sequence using routine skill. For the full-length native human PRO10282 and PRO19578 polypeptides and encoding nucleic acid described herein, Applicants have identified what is believed to be the reading frame best identifiable with the sequence information available at the time.

Using the ALIGN-2 sequence alignment computer program referenced above, it has been found that the full-length native sequence PRO10282 (shown in FIG. 2 and SEQ ID NO:2) has certain amino acid sequence identity with Slra6, a murine protein induced in response to relinoic acid (AF062476). Accordingly, it is presently believed that the PRO10282 polypeptide disclosed in the present application is a newly identified member of the Stra6 protein family and may possess one or more biological and/or immunological activities or properties typical of that protein family. PRO19578 is currently believed to be an alternatively spliced variant of native, full-length human PRO10282, which has 9 amino acids (SPVDFLAGD) deleted at positions 89-97 of the native human PRO10282 amino acid sequence (SEQ ID NO: 2), and contains Ile (I) instead of Met (M) at position 518, which corresponds to position 527 of PRO10282. This indicates that Stra6 may be polymorphic.

B. PRO10282 (Stra6) Variants

Two specific native sequence human Stra6 polypeptides (native sequence human PRO10282 and PRO19578) are disclosed herein. As noted above, PRO19578 is believed to be an alternatively spliced nativa variant of native sequence human PRO10282 and is, therefore, a "PRO10282 variant." In addition to the full-length native sequence PRO10282 and PRO19578 polypeptides described herein, it is contemplated that PRO10282 and PRO19578 variants can be prepared. PRO10282 and PRO19578 variants can be prepared by introducing appropriate nucleotide changes into the PRO10282 or PRO19578 DNA, and/or by synthesis of the desired PRO10282 variant polypeptide. Those skilled in the art will appreciate that amino acid changes may alter post-translational processes of the PRO10282 or PRO19578, such as changing the number or position of glycosylation sites or altering the membrane anchoring characteristics.

Variations in the native full-length sequence PRO10282, PRO19578 or in various domains of the PRO10282 or PRO19578 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO10282 or PRO19578 that results in a change in the amino acid sequence of the PRO10282 or PRO19578 as compared with the native sequence PRO10282 or PRO19578. Optionally the variation is by substitution of at least one amino acid with any other amino acid in one or more of the domains of the PRO10282 or PRO19578. Guidance in determining which amino acid residue may be inserted, substituted or deleted without adversely affecting the desired activity may be found by comparing the sequence of the PRO10282 or PRO19578 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO10282 polypeptide fragments are provided herein. Such fragments may be truncated at the N-terminus or C-terminus, or may lack internal residues, for example, when compared with a full-length native protein. Certain fragments lack amino acid residues that are not essential for a desired biological activity of the PRO10282 or PRO19578 polypeptide.

PRO10282 or PRO19578 fragments may be prepared by any of a number of conventional techniques. Desired peptide fragments may be chemically synthesized. An alternative approach involves generating PRO10282 or PRO19578 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO10282 or PRO19578 polypeptide fragments share at least one biological and/or immunological activity with the native PRO10282 or PRO19578 polypeptide shown in FIG. 2 (SEQ ID NO:2).

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO10282 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: tip, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34-315 (1985)], restriction selection mutagenesis [Wells et al., *Philos. Trans. R. Soc. London SerA,* 317:415 (1986)] or other known techniques can be performed on the cloned DNA to produce the PRO10282 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins,* (W.H. Freeman & Co., N.Y.); Chothia, *J. Mol. Biol.,* 150:1 (1976)]. If alanine substitution does not yield adequate amounts of variant, an isoteric amino acid can be used.

C. Modifications of Native and Variant PRO10282 (Stra6)

Covalent modifications of PRO10282 and PRO10282 variants, including PRO19578, are included within the scope of this invention. One type of covalent modification includes reacting targeted amino acid residues of a PRO10282 polypeptide with an organic derivatizing agent that is capable of reacting with selected side chains or the N- or C-terminal residues of the PRO10282. Derivatization with bifunctional agents is useful, for instance, for crosslinking PRO10282 to a water-insoluble support matrix or surface for use in the method for purifying anti-PRO10282 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO10282 polypeptides included within the scope of this invention comprises altering the native glycosylation pattern of the polypeptide. Native sequence PRO10282 and PRO19578 polypeptides contain an N-linked glycosylation site at positions 8-12 of their amino acid sequence. "Altering the native glycosylation pattern" is intended for purposes herein to mean deleting one or more carbohydrate moieties found in a native sequence PRO10282 or PRO19578 (either by removing the underlying glycosylation site or by deleting the glycosylation by chemical and/or enzymatic means), and/or adding one or more glycosylation sites that are not present in the native sequence PRO10282 or PRO19578. In addition, the phrase includes qualitative changes in the glycosylation of the native proteins, involving a change in the nature and proportions of the various carbohydrate moieties present.

Addition of glycosylation sites to a native or variant PRO10282 polypeptide may be accomplished by altering the amino acid sequence. The alteration may be made, for example, by the addition of, or substitution by, one or more serine or threonine residues to the native sequence PRO10282 (for O-linked glycosylation sites). The PRO10282 amino acid sequence may optionally be altered through changes at the DNA level, particularly by mutating the DNA encoding the PRO10282 polypeptide at preselected bases such that codons are generated that will translate into the desired amino acids.

Another means of increasing the number of carbohydrate moieties on the PRO10282 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO10282 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 1J8:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO10282 comprises linking the PRO10282 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The PRO10282 polypeptides of the present invention may also be modified in a way to form a chimeric molecule comprising a PRO10282 fused to another, heterologous polypeptide or amino acid sequence.

In one embodiment, such a chimeric molecule comprises a fusion of the PRO10282 with a tag polypeptide which provides an epitope to which an anti-tag antibody can selectively bind. The epitope tag is generally placed at the amino- or carboxyl-terminus of the PRO10282. The presence of such epitope-tagged forms of the PRO10282 can be detected using an antibody against the tag polypeptide. Also, provision of the epitope tag enables the PRO10282 to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags: the flu HA tag polypeptide and its antibody 12CA5 [Field et al., *Mol. Cell. Biol.* 8:2159-2165 (1988)]: the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an -tubulin epitope peptide [Skinner et al., *J. Biol. Chem.*, 266:5163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO10282 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO10282 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of Naitge or Variant PRO10282 (Stra6) Polypeptide

The description below relates primarily to production of native sequence and variant PRO10282 (Stra6) polypeptides, specifically including PRO19578, by culturing cells transformed or transfected with a vector containing PRO10282 nucleic acid. It is, of course, contemplated that alternative methods, which are well known in the art, may be employed to prepare PRO10282. For instance, the PRO10282 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO10282 may be chemically synthesized separately and combined using chemical or enzymatic methods to produce the full-length PRO10282.

1. Isolation of DNA Encoding PRO10282 (Stra6)

DNA encoding PRO10282 may be obtained from a cDNA library prepared from tissue believed to possess the PRO10282 mRNA and to express it at a detectable level. Accordingly, human PRO10282 DNA can be conveniently obtained from a cDNA library prepared from human tissue, such as described in the Examples. The PRO10282-encoding gene may also be obtained from a genomic library or by known synthetic procedures (e.g., automated nucleic acid synthesis).

Libraries can be screened with probes (such as antibodies to the PRO10282 or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO10282 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first lime, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO10282 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*. 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, poly ornithine, may also be used. For various techniques for transforming mammalian cells, see Keown et al., *Methods in Enzymology*. 185:527-537 (1990) and Mansour et al., *Nature*. 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac) 169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO10282-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol*. 154(2): 737-1742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)). *K. thermotolerans*, and K. marxtanus; *yarrowia* (EP 402, 226); *Pichia pastoris* (EP 183,070: Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwannomyces* such as *Schwannomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112: 284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, EMBO J., 4:475A [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO10282 are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells⁻/-DHFR (CHO, Urlaub and Chasin, *Proc. Natl. Acad. Sci. USA*, 77:4216 (1980)); mouse Sertoli cells (TM4, Mather, *Biol. Reprod.*, 23:243-251 (1980)); human lung cells (W138, ATCC CCL 75); human liver cells (Hep G2, HB 8065); and mouse mammary rumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding a PRO10282 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO10282 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO10282-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces*-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO10282-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*. 85:12 (1977)].

Expression and cloning vectors usually contain a promoter operably linked to the PRO10282-encoding nucleic acid sequence to direct mRNA synthesis. Promoters recognized by a variety of potential host cells are well known. Promoters suitable for use with prokaryotic hosts include the -lactamase and lactose promoter systems [Chang et al., *Nature*, 275:615 (1978); Goeddel et al., *Nature*, 281:544 (1979)], alkaline phosphatase, a tryptophan (tip) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding PRO10282.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucoses-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO10282 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO10282 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, -fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO10282 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO10282.

Still other methods, vectors, and host cells suitable for adaptation to the synthesis of PRO10282 in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO10282 polypeptide or against a synthetic peptide based on the DNA sequences provided herein or against exogenous sequence fused to PRO10282 DNA and encoding a specific antibody epitope.

5. Purification of Polypeptide

Forms of PRO10282 may be recovered from culture medium or from host cell lysates. If membrane-bound, it can be released from the membrane using a suitable detergent solution (e.g. Triton-X 100) or by enzymatic cleavage. Cells employed in expression of PRO10282 can be disrupted by various physical or chemical means, such as freeze-thaw cycling, sonication, mechanical disruption, or cell lysing agents.

It may be desired to purify PRO10282 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO10282. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO10282 produced.

E. Amplification of Genes Encoding the PRO10282 (Stra6) Polypeptides in Tumor Tissues and Cell Lines In one aspect, the present invention is based on the identification and characterization of genes that are amplified in certain cancer cells.

The genome of prokaryotic and eukaryotic organisms is subjected to two seemingly conflicting requirements. One is the preservation and propagation of DNA as the genetic information in its original form, to guarantee stable inheritance through multiple generations. On the other hand, cells or organisms must be able to adapt to lasting environmental changes. The adaptive mechanisms can include qualitative or quantitative modifications of the genetic material. Qualitative modifications include DNA mutations, in which coding sequences are altered resulting in a structurally and/or functionally different protein. Gene amplification is a quantitative modification, whereby the actual number of complete coding sequence, i.e., a gene, increases, leading to an increased number of available templates for transcription, an increased number of translatable transcripts, and, ultimately, to an increased abundance of the protein encoded by the amplified gene.

The phenomenon of gene amplification and its underlying mechanisms have been investigated in vitro in several prokaryotic and eukaryotic culture systems. The best-characterized example of gene amplification involves the culture of eukaryotic cells in medium containing variable concentrations of the cytotoxic drug methotrexate (MTX). MTX is a folic acid analogue and interferes with DNA synthesis by blocking the enzyme dihydrofolate reductase (DHFR). During the initial exposure to low concentrations of MTX most cells (>99.9%) will die. A small number of cells survive, and are capable of growing in increasing concentrations of MTX by producing large amounts of DHFR-RNA and protein. The basis of this overproduction is the amplification of the single DHFR gene. The additional copies of the gene are found as extrachromosomal copies in the form of small, supernumerary chromosomes (double minutes) or as integrated chromosomal copies.

Gene amplification is most commonly encountered in the development of resistance to cytotoxic drugs (antibiotics for bacteria and chemotherapeutic agents for eukaryotic cells) and neoplastic transformation. Transformation of a eukaryotic cell as a spontaneous event or due to a viral or chemical/environmental insult is typically associated with changes in the genetic material of that cell. One of the most common genetic changes-observed in human malignancies are mutations of the p53 protein. p53 controls the transition of cells from the stationary (G1) to the replicative (S) phase and prevents this transition in the presence of DNA damage. In other words, one of the main consequences of disabling p53 mutations is the accumulation and propagation of DNA damage, i.e., genetic changes. Common types of genetic changes in neoplastic cells are, in addition to point mutations, amplifications and gross, structural alterations, such as translocations.

The amplification of DNA sequences may indicate a specific functional requirement as illustrated in the DHFR experimental system. Therefore, the amplification of certain oncogenes in malignancies points toward a causative role of these genes in the process of malignant transformation and maintenance of the transformed phenotype. This hypothesis has gained support in recent studies. For example, the bcl-2 protein was found to be amplified in certain types of non-Hodgkin's lymphoma. This protein inhibits apoptosis and leads to the progressive accumulation of neoplastic cells. Members of the gene family of growth factor receptors have been found to be amplified in various types of cancers suggesting that overexpression of these receptors may make neoplastic cells less susceptible to limiting amounts of available growth factor. Examples include the amplification of the androgen receptor in recurrent prostate cancer during androgen deprivation therapy and the amplification of the growth factor receptor homologue ERB2 in breast cancer. Lastly, genes involved in intracellular signaling and control of cell cycle progression can undergo amplification during malignant transformation. This is illustrated by the amplification of the bcl-I and ras genes in various epithelial and lymphoid neoplasms.

These earlier studies illustrate the feasibility of identifying amplified DNA sequences in neoplasms, because this approach can identify genes important for malignant transformation. The case of ERB2 also demonstrates the feasibility from a therapeutic standpoint, since transforming proteins may represent novel and specific targets for tumor therapy.

Several different techniques can be used to demonstrate amplified genomic sequences. Classical cytogenetic analysis of chromosome spreads prepared from cancer cells is adequate to identify gross structural alterations, such as translocations, deletions and inversions. Amplified genomic regions can only be visualized, if they involve large regions with high copy numbers or are present as extrachromosomal material. While cytogenetics was the first technique to demonstrate the consistent association of specific chromosomal changes with particular neoplasms, it is inadequate for the identification and isolation of manageable DNA sequences. The more recently developed technique of comparative genomic hybridization (CGH) has illustrated the widespread phenomenon of genomic amplification in neoplasms. Tumor and normal DNA are hybridized simultaneously onto metaphases of normal cells and the entire genome can be screened by image analysis for DNA sequences that are present in the tumor at an increased frequency. (WO 93/18, 186; Gray et al., *Radiation Res.*, 137:275-289 [1994]). As a screening method, this type of analysis has revealed a large number of recurring amplicons (a stretch of amplified DNA) in a variety of human neoplasms. Although CGH is more sensitive than classical cytogenetic analysis in identifying amplified stretches of DNA, it does not allow a rapid identification and isolation of coding sequences within the amplicon by standard molecular genetic techniques.

The most sensitive methods to detect gene amplification are polymerase chain reaction (PCR)-based assays. These assays utilize very small amount of tumor DNA as starting material, are exquisitely sensitive, provide DNA that is amenable to further analysis, such as sequencing and are suitable for high-volume throughput analysis.

The above-mentioned assays are not mutually exclusive, but are frequently used in combination to identify amplifications in neoplasms. While cytogenetic analysis and CGH represent screening methods to survey the entire genome for amplified regions, PCR-based assays are most suitable for the final identification of coding sequences, i.e., genes in amplified regions.

According to the present invention, such genes have been identified by quantitative PCR (S. Gelmini et al., *Clin. Chem.* 43:752 [1997]), by comparing RNA from a variety of primari tumors, including breast lung, colon, prostate, brain, liver, kidney, pancrease, spleen, thymus, testis, ovary, uterus, etc., tumor, or tumor cell lines, with pooled DNA from healthy donors. Quantitative PCR was performed using a TaqMan instrument (ABI). Gene-specific primers and fluorogenic probes were designed based upon the coding sequences of the DNAs.

Human lung carcinoma cell lines include A549 (SRCC768), Calu-1 (SRCC769), Calu-6 (SRCC770), H157 (SRCC771), H441 (SRCC772), H460 (SRCC773), SKMES-1 (SRCC774), SW900 (SRCC775), H522 (SRCC832), and H810 (SRCC833), all available from ATCC. Primary human lung tumor cells usually derive from adenocarcinomas, squamous cell carcinomas, large cell carcinomas, non-small cell carcinomas, small cell carcinomas, and broncho alveolar carcinomas, and include, for example, SRCC724 (adenocarcinoma, abbreviated as "AdenoCa") (LT10), SRCC725 (squamous cell carcinoma, abbreviated as "SqCCa") (LT1a), SRCC726 (adenocarcinoma) (LT2), SRCC727 (adenocarcinoma) (LT3), SRCC728 (adenocarcinoma) (LT4), SRCC729 (squamous cell carcinoma) (LT6), SRCC730 (adeno/squamous cell carcinoma) (LT7), SRCC731 (adenocarcinoma) (LT9), SRCC732 (squamous cell carcinoma) (LT10), SRCC733 (squamous cell carcinoma) (LT11), SRCC734 (adenocarcinoma) (LT12), SRCC735 (adeno/squamous cell carcinoma) (LT13), SRCC736 (squamous cell carcinoma) (LT15), SRCC737 (squamous cell carcinoma) (LT16), SRCC738 (squamous cell carcinoma) (LT17), SRCC739 (squamous cell carcinoma) (LT18), SRCC740 (squamous cell carcinoma) (LT19), SRCC741 (lung cell carcinoma, abbreviated as "LCCa") (LT21), SRCC811 (adenocarcinoma) (LT22), SRCC825 (adenocarcinoma) (LT8), SRCC886 (adenocarcinoma) (LT25), SRCC887 (squamous cell carcinoma) (LT26), SRCC888 (adeno-BAC carcinoma) (LT27), SRCC889 (squamous cell carcinoma) (LT28), SRCC890 (squamous cell carcinoma) (LT29), SRCC891 (adenocarcinoma) (LT30), SRCC892 (squamous cell carcinoma) (LT31), SRCC894 (adenocarcinoma) (LT33). Also included are human lung tumors designated SRCC1125 [HF-000631], SRCC1127 [HF-000641], SRCC1129 [HF-000643], SRCC1133 [HF-000840], SRCC1135 [HF-000842], SRCC1227 [HF-001291], SRCC1229 [HF-001293], SRCC1230 [HF-001294], SRCC1231 [HF-001295], SRCC1232 [HF-001296], SRCC1233 [HF-001297], SRCC1235 [HF-001299], and SRCC1236 [HF-001300].

Colon cancer cell lines include, for example, ATCC cell lines SW480 (adenocarcinoma, SRCC776), SW620 (lymph node metastasis of colon adenocarcinoma, SRCC777), Colo320 (carcinoma, SRCC778), HT29 (adenocarcinoma, SRCC779), HM7 (a high mucin producing variant of ATCC colon adenocarcinoma cell line. SRCC780., obtained from Dr. Robert Warren, UCSF), CaWiDr (adenocarcinoma, SRCC781), HCT116 (carcinoma, SRCC782), SKCO1 (adenocarcinoma, SRCC783), SW403 (adenocarcinoma, SRCC784), LS174T (carcinoma, SRCC785), Colo205 (carcinoma, SRCC828), HCT15 (carcinoma, SRCC829), HCC2998 (carcinoma, SRCC830), and KM12 (carcinoma, SRCC831). Primary colon tumors include colon adenocarcinomas designated CT2 (SRCC742), CT3 (SRCC743), CT8 (SRCC744), CT10 (SRCC745), CT12 (SRCC746), CT14 (SRCC747), CT15 (SRCC748), CT16 (SRCC749), CT17 (SRCC750), CT1 (SRCC751), CT4 (SRCC752), CT5 (SRCC753), CT6 (SRCC754), CT7 (SRCC755), CT9 (SRCC756), CT11 (SRCC757), CT18 (SRCC758), CT19 (adenocarcinoma, SRCC906), CT20 (adenocarcinoma, SRCC907), CT21 (adenocarcinoma, SRCC908), CT22 (adenocarcinoma, SRCC909), CT23 (adenocarcinoma, SRCC910), CT24 (adenocarcinoma, SRCC911), CT25 (adenocarcinoma, SRCC912), CT26 (adenocarcinoma, SRCC913), CT27 (adenocarcinoma, SRCC914), CT28 (adenocarcinoma, SRCC915), CT29 (adenocarcinoma, SRCC916), CT30 (adenocarcinoma, SRCC917), CT31 (adenocarcinoma, SRCC918), CT32 (adenocarcinoma, SRCC919), CT33 (adenocarcinoma, SRCC920), CT35 (adenocarcinoma, SRCC921), and CT36 (adenocarcinoma, SRCC922). Also included are human colon tumors designated SRCC1051 [HF-000499], SRCC1052 [HF-000539], SRCC1053 [HF-000575], SRCC1054 [HF-000698], SRCC1142 [HF-000762], SRCC1144 [HF-000789], SRCC1146 [HF-000795] and SRCC1148-[HF-000811].

Human breast carcinoma cell lines include, for example, HBL100 (SRCC759), MB435s (SRCC760), T47D (SRCC761), MB468 (SRCC762), MB175 (SRCC763), MB361 (SRCC764), BT20 (SRCC765), MCF7 (SRCC766), and SKBR3 (SRCC767), and human breast rumor center designated SRCC1057 [HF-000545]. Also included are human breast tumors designated SRCC1094, SRCC1095, SRCC1096, SRCC1097, SRCC1098, SRCC1099, SRCC1100, SRCC1101, and human breast-met-lung-NS tumor designated SRCC893 [LT 32].

Human kidney tumor centers include SRCC989 [HF-000611] and SRCC1014 [HF-000613].

Human testis tumor center includes SRCC1001 [HF-000733] and testis tumor margin SRCC999 [HF-000716].

Human parathyroid tumor includes SRCC1002 [HF-0008311] and SRCC1003 [HF-000832].

F. Tissue Distribution

The results of the gene amplification assays herein can be verified by further studies, such as, by determining mRNA expression in various human tissues.

As noted before, gene amplification and/or gene expression in various tissues may be measured by conventional Southern blotting, Northern blotting to quantitate the transcription of mRNA (Thomas, *Proc. Natl. Acad. Sci. USA.* 77:5201-5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO10282 (Stra6) polypeptide or against a synthetic peptide based on the DNA and encoding a specific antibody epitope. General techniques for generating antibodies, and special protocols for Northern blotting and in situ hybridization are provided hereinbelow.

G. Chromosome Mapping

If the amplification of a given gene is functionally relevant, then that gene should be amplified more than neighboring genomic regions which are not important for tumor survival. To test this, the gene can be mapped to a particular chromosome, e.g., by radiation-hybrid analysis. The amplification level is then determined at the location identified, and at the neighboring genomic region. Selective or preferential amplification at the genomic region to which the gene has been mapped is consistent with the possibility that the gene amplification observed promotes tumor growth or survival. Chromosome mapping includes both framework and epicenter mapping. For further details see, e.g., Stewart et al., *Genome Research,* 7:422-433 (1997).

H. Antibody Binding Studies

The results of the gene amplification study can be further verified by antibody binding studies, in which the ability of anti-PRO10282 (anti-Stra6) antibodies to inhibit the expression of Stra6 polypeptides on tumor (cancer) cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques*, pp. 147-158 (CRC Press, Inc., 1987).

Competitive binding assays rely on the ability of a labeled standard to compete with the test sample analyte for binding with a limited amount of antibody. The amount of target protein (encoded by a gene amplified in a tumor cell) in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

1. Cell-Based Tumor Assays

Cell-based assays and animal models for tumors (e.g., cancers) can be used to verify the findings of the gene amplification assay, and further understand the relationship between the genes identified herein and the development and pathogenesis of neoplastic cell growth. The role of gene products identified herein in the development and pathology of tumor or cancer can be tested by using primary tumor cells or cells lines that have been identified to amplify the genes herein. Such cells include, for example, the breast, colon and lung cancer cells and cell lines listed above.

In a different approach, cells of a cell type known to be involved in a particular tumor are transfected with the cDNAs herein, and the ability of these cDNAs to induce excessive growth is analyzed. Suitable cells include, for example, stable tumor cells lines such as, the B104-1-1 cell line (stable NIH-3T3 cell line transfected with the neu protooncogene) and ras-transfected NIH-3T3 cells, which can be transfected with the desired gene, and monitored for tumorogenic growth. Such transfected cell lines can then be used to test the ability of poly- or monoclonal antibodies or antibody compositions to inhibit tumorogenic cell growth by exerting cytostatic or cytotoxic activity on the growth of the transformed cells, or by mediating antibody-dependent cellular cytotoxicity (ADCC). Cells transfected with the coding sequences of the genes identified herein can further be used to identify drug candidates for the treatment of cancer.

In addition, primary cultures derived from rumors in transgenic animals (as described below) can be used in the cell-based assays herein, although stable cell lines are preferred. Techniques to derive continuous cell lines from transgenic animals are well known in the art (see, e.g., Small et al., *Mol. Cell. Biol.*, 5:642-648 [1985]).

J. Animal Models

A variety of well known animal models can be used to further understand the role of the genes identified herein in the development and pathogenesis of tumors, and to test the efficacy of candidate therapeutic agents, including antibodies, and other antagonists of the native polypeptides, including small molecule antagonists. The in vivo nature of such models makes them particularly predictive of responses in human patients. Animal models of tumors and cancers (e.g., breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g., subcutaneous injection, tail vein injection, spleen implantation, intraperitoneal implantation, implantation under the renal capsule, or orthopin implantation, e.g., colon cancer cells implanted in colonic tissue (see, e.g., PCT publication No. WO 97/33551, published Sep. 18, 1997).

Probably the most often used animal species in oncological studies are immunodeficient mice and, in particular, nude mice. The observation that the nude mouse with hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII and SJL. In addition, a wide variety of other animals with inherited immunological defects other than the nude mouse have been bred and used as recipients of tumor xenografts. For further details see, e.g., *The Nude Mouse in Oncology Research*, E. Boven and B. Winograd, eds., CRC Press, Inc., 1991.

The cells introduced into such animals can be derived from known tumor/cancer cell lines, such as, any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); a moderately well-differentiated grade JJ human colon adenocarcinoma cell line, HT-29 (ATCC HTB-38), or from tumors and cancers. Samples of tumor or cancer cells can be obtained from patients undergoing surgery, using standard conditions, involving freezing and storing in liquid nitrogen (Karmali et al., *Br. J. Cancer.* 48:689-696 [1983]).

Tumor cells can be introduced into animals, such as nude mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue. Boven and Winograd (1991), supra.

Animal models of breast cancer can be generated, for example, by implanting rat neuroblastoma cells (from which the neu oncogen was initially isolated), or neu-transformed NIH-3T3 cells into nude mice, essentially as described by Drebin et al., *PNAS USA*. 83:9129-9133 (1986).

Similarly, animal models of colon cancer can be generated by passaging colon cancer cells in animals, e.g., nude mice, leading to the appearance of tumors in these animals. An orthotopic transplant model of human colon cancer in nude mice has been described, for example, by Wang et al., *Cancer Research*, 54:4726-4728 (1994) and Too et al., *Cancer Research*, 55:681-684 (1995). This model is based on the so-called "METAMOUSE" sold by Anticancer, Inc., (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., *J. Exp. Med.*, 146:720 [1977]), which provide a highly controllable model system for studying the anti-tumor activities of various agents (Palladino et al., *J. Immunol.*, 138:4023-4032 [1987]). Briefly, tumor cells are propagated in vitro in cell culture. Prior to injection into the animals, the cell lines are washed and suspended in buffer, at a cell density of about $10 \times 10^6$ to $10 \times 10^7$ cells/ml. The animals are then infected subcutaneously with 10 to 100 μl of the cell suspension, allowing one to three weeks for a tumor to appear.

In addition, the Lewis lung (3LL) carcinoma of mice, which is one of the most thoroughly studied experimental rumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., *Br. J. Cancer,* 41:suppl. 4:309 [1980]), and evidence indicates that tumors can be started from injection of even a single cell and that a very high proportion of infected tumor cells survive. For further information about this tumor model see, Zacharski, *Haemostasis,* 16:300-320 [1986]).

One way of evaluating the efficacy of a test compound in an animal model on an implanted tumor is to measure the size of the tumor before and after treatment. Traditionally, the size of implanted tumors has been measured with a slide caliper in two or three dimensions. The measure limited to two dimensions does not accurately reflect the size of the tumor, therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop on Immune-Deficient Animals*, Wu and Sheng eds., Basel, 1989, 301. It is noted, however, that necrosis and inflammatory responses following treatment may actually result in an increase in tumor size, at least initially. Therefore, these changes need to be carefully monitored, by a combination of a morphometric method and flow cytometric analysis.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA*, 82:6148-615 [1985]); gene targeting in embryonic stem cells (Thompson et al. *Cell,* 56:313-321 [1989]); electroporation of embryos (Lo, *Mol. Cell. Biol.,* 3:1803-1814 [1983]); sperm-mediated gene transfer (Lavitrano et al. *Cell,* 57:717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA,* 89:6232-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

Alternatively, "knock out" animals can be constructed which have a defective or altered gene encoding a PRO10282 (Stra6) polypeptide identified herein, as a result of homologous recombination between the endogenous gene encoding the polypeptide and altered genomic DNA encoding the same polypeptide introduced into an embryonic cell of the animal. For example, cDNA encoding a PRO10282 polypeptide can be used to clone genomic DNA encoding that polypeptide in accordance with established techniques. A portion of the genomic DNA encoding a particular PRO10282 polypeptide can be deleted or replaced with another gene, such as a gene encoding a selectable marker which can be used to monitor integration. Typically, several kilobases of unaltered flanking DNA (both at the 5' and 3' ends) are included in the vector [see, e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see, e.g., Li et al., *Cell,* 69:915 (1992)]. The selected cells are then injected into a blastocyst of an animal (e.g., a mouse or rat) to form aggregation chimeras [see, e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, by their ability to defend against certain pathological conditions and by their development of pathological conditions due to absence of the PRO10282 polypeptide.

The efficacy of antibodies specifically binding the polypeptides identified herein and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination, biopsy, and is scanned by computed tomography (CT). Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chrondroma, leiomyosarcoma of dogs, cats, and baboons can also be tested. Of these mammary adenocarcinoma in dogs and cats is a preferred model as its appearance and behavior are very similar to those in humans. However, the use of this model is limited by the rare occurrence of this type of tumor in animals.

K. Screening Assays for Drug Candidates

Screening assays for drug candidates are designed to identify compounds that bind or complex with the polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO10282 polypeptide encoded by a gene identified herein, its interaction with that polypeptide can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature,* 340:245-246 (1989); Chien et al., *Proc. Natl. Acad. Sci. USA.* 88: 9578-9582 (1991)] as disclosed by Chevray and Nathans. *Proc. Natl. Acad. Sci. USA.* 89:5789-5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for -galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a PRO10282-encoding gene identified herein and other intra- or extracellular components can be tested as follows: usually a reaction mixture is prepared containing the product of the amplified gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO10282 polypeptide may be added to a cell along with the compound to be screened for a particular activity and the ability of the compound to inhibit the activity of interest in the presence of the PRO10282 polypeptide indicates that the compound is an antagonist to the PRO10282 polypeptide. Alternatively, antagonists may be detected by combining the PRO10282 polypeptide and a potential antagonist with membrane-bound PRO10282 polypeptide receptors or recombinant receptors under appropriate conditions for a competitive inhibition assay. The PRO10282 polypeptide can be labeled, such as by radioactivity, such that the number of PRO10282 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the PRO10282 polypeptide and a cDNA library created from this RNA is divided into pools and used to transfect COS cells or other cells that are not responsive to the PRO10282 polypeptide. Transfected cells that are grown on glass slides are exposed to labeled PRO10282 polypeptide. The PRO10282 polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO10282 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO10282 polypeptide in the presence of the candidate compound. The ability of the compound to enhance or block this interaction could then be measured.

More specific examples of potential antagonists include an oligonucleotide that binds to the fusions of immunoglobulin with the PRO10282 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO10282 polypeptide that recognizes the receptor but imparts no effect, thereby competitively inhibiting the action of the PRO10282 polypeptide.

Another potential PRO10282 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO10282 polypeptide herein, is used to design an antisense RNA oligonucleotide of from about 10 to 40 base pairs in length. A DNA oligonucleotide is designed to be complementary to a region of the gene involved in transcription (triple helix—see, Lee et al., *Nucl. Acids Res.*, 6:3073 (1979); Cooney et al., Science, 241: 456 (1988); Dervan et al., *Science*, 251:1360 (1991)), thereby preventing transcription and the production of the PRO10282 polypeptide. The antisense RNA oligonucleotide hybridizes to the mRNA in vivo and blocks translation of the mRNA molecule into the PRO10282 polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO10282 polypeptide. When antisense DNA is used, oligodeoxyribonucleotides derived from the translation-initiation site, e.g., between about −10 and + 10 positions of the target gene nucleotide sequence, are preferred.

Antisense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

Potential antagonists include small molecules that bind to the active site, the receptor binding site, or growth factor or other relevant binding site of the PRO10282 polypeptide, thereby blocking the normal biological activity of the PRO10282 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, Current Biology, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

L. Uses for PRO10282 (Stra6)

Nucleotide sequences (or their complement) encoding PRO10282 (Stra6) polypeptides have various applications in the art of molecular biology, including uses as hybridization probes, in chromosome and gene mapping and in the generation of anti-sense RNA and DNA. PRO10282 nucleic acid will also be useful for the preparation of PRO10282 polypeptides by the recombinant techniques described herein.

The full-length native sequence PRO10282 gene (SEQ ID NO:1), or PRO19578 gene (SEQ ID NO: 4), or portions thereof, may be used as hybridization probes for a cDNA library to isolate the full-length PRO10282 or PRO19578 cDNA or to isolate still other cDNAs (for instance, those encoding further naturally-occurring variants of PRO10282, or PRO10282 from other species) which have a desired sequence identity to the PRO10282 coding sequence disclosed in FIG. 1 (SEQ ID NO:1) or the PRO19578 coding sequence disclosed in FIG. 6 (SEQ ID NO: 4). Optionally, the length of the probes will be about 20 to about 50 bases. The hybridization probes may be derived from at least partially novel regions of the nucleotide sequence of SEQ ID NO:1 wherein those regions may be determined without undue experimentation or from genomic sequences including promoters, enhancer elements and introns of the native PRO10282 or PRO19578 gene. By way of example, a screening method will comprise isolating the coding region of the PRO10282 or PRO19578 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO10282 or PRO19578 gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO10282 (Stra6) nucleic acids include antisense or sense oligonucleotides comprising a singe-stranded nucleic acid sequence (either RNA or DNA) capable of binding to target PRO10282 (Stra6) mRNA (sense) or PRO10282 (Stra6) DNA (antisense) sequences. Antisense or sense oligonucleotides, according to the present invention, comprise a fragment of the coding region of PRO10282 (Stra6) DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (Cancer Res. 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO10282 (Stra6) proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand-binding molecule, as described in WO 91/04753. Suitable ligand binding molecules include, but are not limited to, cell surface receptors, growth factors, other cytokines, or other ligands that bind to cell surface receptors. Preferably, conjugation of the ligand-binding molecule does not substantially interfere with the ability of the ligand-binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The probes may also be employed in PCR techniques to generate a pool of sequences for identification of closely related PRO10282 coding sequences.

Nucleotide sequences encoding a native sequence PRO10282 (Stra6) polypeptide can also be used to construct hybridization probes for mapping the gene, which encodes that native sequence PRO10282 (Stra6) and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO10282 encode a protein which binds to another protein (for example, where the PRO10282 is a receptor), the PRO10282 can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO10282 (Stra6) can be used to isolate correlative ligand(s). Screening assays can be designed to find lead compounds that mimic the biological activity of a native PRO10282 (Stra6) or a native polypeptide binding to PRO10282 ("PRO10282 binding protein"). Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO10282 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO10282 can be used to clone genomic DNA encoding PRO10282 in accordance with established techniques and the genomic sequences used to generate transgenic animals that contain cells which express DNA encoding PRO10282. Methods for generating transgenic animals, particularly animals such as mice or rats, have become conventional in the art and are described, for example, in U.S. Pat. Nos. 4,736,866 and 4,870,009. Typically, particular cells would be targeted for PRO10282 transgene incorporation with tissue-specific enhancers. Transgenic animals that include a copy of a transgene encoding PRO10282 introduced into the germ line of the animal at an embryonic stage can be used to examine the effect of increased expression of DNA encoding PRO10282. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO10282 can be used to construct a PRO10282 "knock out" animal which has a defective or altered gene encoding PRO10282 as a result of homologous recombination between the endogenous gene encoding PRO10282 and altered genomic DNA encoding PRO10282 introduced into an embryonic stem cell of the animal. For example, cDNA encoding PRO10282 can be used to clone genomic DNA encoding PRO10282 in accordance with established techniques. A portion of the genomic DNA encoding PRO10282 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO10282 polypeptide.

Nucleic acid encoding the PRO10282 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO10282 polypeptides described herein may also be employed as molecular weight markers for protein electrophoresis purposes.

The nucleic acid molecules encoding the PRO10282 polypeptides or fragments thereof described herein are useful for chromosome identification. In this regard, there exists an ongoing need to identify new chromosome markers, since relatively few chromosome marking reagents, based upon actual sequence data are presently available. Each PRO10282 nucleic acid molecule of the present invention can be used as a chromosome marker.

The PRO10282 polypeptides and nucleic acid molecules of the present invention may also be used for tissue typing, wherein the PRO10282 polypeptides of the present invention may be differentially expressed in one tissue as compared to another. PRO10282 nucleic acid molecules will find use for generating probes for PCR, Northern analysis, Southern analysis and Western analysis.

The PRO10282 polypeptides described herein may also be employed as therapeutic agents. The PRO10282 polypeptides of the present invention can be formulated according to known methods to prepare pharmaceutically useful compositions, whereby the PRO10282 product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO10282 polypeptide or agonist or antagonist thereof is employed, normal dosage amounts may vary from about 10 ng/kg to up to 100 mg/kg of mammal body weight or more per day, preferably about 1 g/kg/day to 10 mg/kg/day, depending upon the route of administration. Guidance as to particular dosages and methods of delivery is provided in the literature; see, for example, U.S. Pat. No. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO10282 polypeptide is desired in a formulation with release characteristics suitable for the treatment of any disease or disorder requiring administration of the PRO10282 polypeptide, microencapsulation of the PRO10282 polypeptide is contemplated. Microencapsulation of recombinant proteins for sustained release has been successfully performed with human growth hormone (rhGH), interferon- (rhIFN-), interleukin-2, and MN rgp120. Johnson et al., *Nat. Med.,* 2:795-799 (1996); Yasuda, *Biomed. Ther.,* 27:1221-1223 (1993); Hora et al., *Bio/Technology,* 8:755-758 (1990); Cleland, "Design and Production of Single Immunization Vaccines Using Polylactide Polyglycolide Microsphere Systems," in *Vaccine Design: The Subunit and Adjuvant Approach,* Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO10282 polypeptide (agonists) or prevent the effect of the PRO10282 polypeptide (antagonists). Screening assays for antagonist drug candidates are designed to identify compounds that bind or complex with the PRO10282 polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO10282 polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO10282 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO10282 polypeptide and drying. Alternatively, an immobilized antibody, e.g., a monoclonal antibody, specific for the PRO10282 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO10282 polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast based genetic system described by Fields and co-workers (Fields and Song, *Nature (London),* 340:245-246 (1989); Chien et al., *Proc. Natl. Acad. Sci. USA,* 88:9578-9582 (1991) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO10282 polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO10282 polypeptide may be added to a cell along with the compound to be screened for a particular activity and the ability of the compound to inhibit the activity of interest in the presence of the PRO10282 polypeptide indicates that the compound is an antagonist to the PRO10282 polypeptide. Alternatively, antagonists may be detected by combining the PRO10282 polypeptide and a potential antagonist with membrane-bound PRO10282 polypeptide receptors or recombinant receptors under appropriate conditions for a competitive inhibition assay. The PRO10282 polypeptide can be labeled, such as by radioactivity, such that the number of PRO10282 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the PRO10282 polypeptide and a cDNA library created from this RNA is divided into pools and used to transfect COS cells or other cells that are not responsive to the PRO10282 polypeptide. Transfected cells that are grown on glass slides are exposed to labeled PRO10282 polypeptide. The PRO10282 polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO10282 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO10282 polypeptide in the presence of the candidate compound. The ability of the compound to enhance or block this interaction could then be measured.

More specific examples of potential antagonists include an oligonucleotide that binds to the fusions of immunoglobulin with PRO10282 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO10282 polypeptide that recognizes the receptor but imparts no effect, thereby competitively inhibiting the action of the PRO10282 polypeptide.

Another potential PRO10282 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO10282 polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science.* 251:1360 (1991)), thereby preventing transcription and the production of the PRO10282 polypeptide. The antisense RNA oligonucleotide hybridizes to the mRNA in vivo and blocks translation of the mRNA molecule into the PRO10282 polypeptide (antisense—Okano, Neurochem., 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO10282 polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO10282 polypeptide, thereby blocking the normal biological activity of the PRO10282 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Stra6, a murine retinoic acid inducible gene, has a spermatogenic cycle-dependent expression in Sertoli cells in testis. Based on sequence homology with Stra6, the PRO10282 polypeptides disclosed herein may have an important role in spermatogenesis, and therefore has a potential use in fertility treatment. It is currently believed that the expression of PRO10282 polypeptide, just like that of its murine homolog Stra6, is induced in response to retinoic acid. Therefore, the expression of PRO10282 at the level of mRNA, by hybridization, or protein, by immunological assays, can be used to determine whether a test compound has a potential for the treatment of a wide variety of retinoid responsive diseases. Among the types of diseases contemplated as therapeutic targets include psoriasis, acne, dysplasias, cancers and autoimmune diseases. The category of contemplated dysplasias includes precancerous lesions of the epithelial tissues such as oral leukoplakias, dysplasia of the cervix, larynx and bronchi. The category of contemplated cancers includes carcinomas of colon (adenocarcinoma), lung (carcinoma and adenocarcinoma), skin, head and neck, cervix, uterus, breast and prostate. The category of contemplated autoimmune diseases includes rheumatoid arthritis, osteoarthritis, systemic lupus erythematosus, pemphigus valgaris and pemphigus foliaceous. Potential therapeutics to treat such diseases and conditions are antibodies and antagonists (including small molecules) of PRO10282.

M. Compositions and Methods for the Treatment of Tumors

The compositions useful in the treatment of tumors associated with the amplification of the genes identified herein include, without limitation, antibodies, small organic and inorganic molecules, peptides, phosphopeptides, antisense and ribozyme molecules, triple helix molecules, etc., that inhibit the expression and/or activity of the target gene product.

For example, antisense RNA and RNA molecules act to directly block the translation of mRNA by hybridizing to targeted mRNA and preventing protein translation. When antisense DNA is used, oligodeoxyribonucleotides derived from the translation initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g., PCT publication No. WO 97/33551, supra.

These molecules can be identified by any or any combination of the screening assays discussed hereinabove and/or by any other screening techniques well known for those skilled in the art.

N. Anti-PRO10282 (Anti-Stra6) Antibodies

The present invention further provides anti-PRO10282 (anti-Stra6) antibodies. Exemplary antibodies include polyclonal, monoclonal, humanized, bispecific, and heteroconjugate antibodies.

1. Polyclonal Antibodies

The anti-PRO10282 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO10282 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycoiate). The immunization protocol may be selected by one skilled in the art without undue experimentation.

2. Monoclonal Antibodies

The anti-PRO10282 antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO10282 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against PRO10282. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO10282 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol. 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science. 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

4. Bispecific Antibodies

Bispecific antibodies are monoclonal, preferably human or humanized, antibodies that have binding specificities for at least two different antigens. In the present case, one of the binding specificities is for the PRO10282, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps.

Similar procedures are disclosed in WO 93/08829, published 13 May 1993, and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ nd $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994). Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO10282 polypeptide herein. Alternatively, an anti-PRO10282 polypeptide arm may be combined with an arm which binds to a triggering molecule on a leukocyte such as a T-cell receptor molecule (e.g. CD2, CD3, CD28, or B7), or Fc receptors for IgG (Fc R), such as Fc RI (CD64), Fc RII (CD32) and Fc RIII (CD16) so as to focus cellular defense mechanisms to the cell expressing the particular PRO10282 polypeptide. Bispecific antibodies may also be used to localize cytotoxic agents to cells which express a particular PRO10282 polypeptide. These antibodies possess a PRO10282-binding arm and an arm which binds a cytotoxic agent or a radionuclide chelator, such as EOTUBE, DPTA, DOTA, or TETA. Another bispecific antibody of interest binds the PRO10282 polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include immothioate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.,* 176: 1191-1195 (1992) and Shopes, *J. Immunol.,* 148: 2918-2922 (1992). Homodimeric antibodies with enhanced anti-tumor activity may also be prepared using heterobifunctional crosslinkers as described in Wolff et al. *Cancer Research,* 53: 2560-2565 (1993). Alternatively, an antibody can be engineered that has dual Fc regions and may thereby have enhanced complement lysis and ADCC capabilities. See Stevenson et al., *Anti-Cancer Drug Design,* 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl. Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide-interchange reaction. A chemotherapeutic agent (such as Doxorubicin) is optionally contained within the liposome. See Gabizon et al., *J. National Cancer Inst.* 81(19): 1484 (1989).

8. Antibody-Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such as way so as to convert it into its more active, cytotoxic form.

Enzymes that are useful in the method of this invention include, but are not limited to, glycosidase, glucose oxidase, human lysozyme, human glucuronidase, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug 5-fluorouracil; proteases, such as serratia protease, thermolysin, subtilisin, carboxypeptidases (e.g., carboxypeptidase G2 and carboxypeptidase A) and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as—galactosidase and neuraminidase useful for converting glycosylated prodrugs into free drugs; β-lactamase useful for converting drugs derived from β-lactams into free drugs; and penicillin amidases, such as penicillin V amidase or penicillin G amidase, useful for converting drugs derivatized at their amine nitrogens with phenoxyacetyl or phenyl acetyl groups, respectively, into free drugs. Alternatively, antibodies with enzymatic activity, also known in the art as "abzymes" can be used to convert the prodrugs of the invention into free active drugs (see, e.g., Massey, *Nature,* 328:457-458 (1987)). Antibody-abzyme conjugates can be prepared as described herein for delivery of the abzyme to a tumor cell population.

The enzymes of this invention can be covalently bound to the anti-PRO10282 (anti-Stra6) antibodies by techniques well known in the art such as the use of the heterobifunctional cross-linking agents discussed above. Alternatively, fusion proteins comprising at least the antigen binding region of the antibody of the invention linked to at least a functionally active portion of an enzyme of the invention can be constructed using recombinant DNA techniques well known in the art (see, e.g., Neuberger et al., *Nature,* 312:604-608 (1984)).

10. Pharmaceutical Compositions of Antibodies

Antibodies specifically binding a PRO10282 polypeptide identified herein, as well as other molecules identified by the screening assays disclosed hereinbefore, can be administered for the treatment of various disorders in the form of pharmaceutical compositions.

If the PRO10282 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences,* supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

O. Uses for anti-PRO10282 (Anti-Stra6) Antibodies

The anti-PRO10282 antibodies of the invention have various utilities. For example, anti-PRO10282 antibodies may be used in diagnostic assays for PRO10282, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques,* CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-PRO10282 antibodies also are useful for the affinity purification of PRO10282 from recombinant cell culture or natural sources. In this process, the antibodies against PRO10282 are immobilized on a suitable support, such a Sephadex resin or filter paper, using methods well known in the art. The immobilized antibody then is contacted with a sample containing the PRO10282 to be purified, and thereafter the support is washed with a suitable solvent that will remove substantially all the material in the sample except the PRO10282, which is bound to the immobilized antibody. Finally, the support is washed with another suitable solvent that will release the PRO10282 from the antibody.

Anti-PRO10282 antibodies can be used to monitor the expression of PRO10282 polypeptide which has a potential use as a sensitive method to screen for therapeutically useful compounds against a wide variety of retinoid responsive diseases. Among the types of diseases contemplated as therapeutic targets include psoriasis, acne, dysplasias, cancers and autoimmune diseases. The category of contemplated dysplasias includes precancerous lesions of the epithelial tissues such as oral leukoplakias, dysplasia of the cervix, larynx and bronchi. The category of contemplated cancers includes carcinomas of colon (adenocarcinoma), lung (adenocarcinoma and carcinoma), skin, head and neck, cervix, uterus, breast and prostate. The category of contemplated autoimmune diseases includes rheumatoid arthritis, osteoarthritis, systemic lupus erythematosus, pemphigus valgaris and pemphigus foliaceous. Anti-PRO10282 antibodies have potential therapeutic use in the treatment of such diseases and conditions.

P. Methods of Treatment Using Anti-PRO10282 (Stra6) Antibodies and other Stra6 Antagonists It is contemplated that the antibodies and other anti-tumor compounds of the present invention may be used to treat various conditions, including those characterized by overexpression and/or activation of the amplified genes identified herein. Exemplary conditions or disorders to be treated with such antibodies and other compounds, including, but not limited to, small organic and inorganic molecules, peptides, antisense molecules, etc., include benign or malignant tumors (e.g. renal, liver, kidney, bladder, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders. Particularly preferred targets for treatment with anti-Stra6 antibodies and other antagonists of the present invention are tumors that harbor genetic defects in the Wnt-1 pathway (e.g. leading to abnormal activation of β-catenin signaling) and/or overexpress Stra6. It has been found that human cancers harboring genetic defects in the Wnt-1 pathway typically also exhibit overexpression of Stra6, but not all Stra6 overexpressing tumors have been known to be associated with mutations in the Wnt-1 pathway. The Stra6 antagonists of the present invention have great potential in the treatment of Stra6 overexpressing tumors. A preferred group of such tumors includes colorectal tumors, ovary, endometrium, and Wilm's kidney tumors, melanoma, and pheochromocytome (a tumor derived from the adrenal medulla).

The anti-tumor agents of the present invention, e.g., antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens may be combined with the administration of the anti-cancer agents, e.g., antibodies of the instant invention. For example, the patient to be treated with such anti-cancer agents may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the anti-tumor agent, e.g., antibody, or may be given simultaneously therewith. The antibody may be combined with an anti-oestrogen compound such as tamoxifen or an anti-progesterone such as onapristone (see, EP 616812) in dosages known for such molecules.

It may be desirable to also administer antibodies against other tumor associated antigens, such as antibodies which bind to the ErbB2, EGFR, ErbB3, ErbB4, or vascular endothelial factor (VEGF). Alternatively, or in addition, two or more antibodies binding the same or two or more different antigens disclosed herein may be co-administered to the patient. Sometimes, it may be beneficial to also administer one or more cytokines to the patient. In a preferred embodiment, the antibodies herein are co-administered with a growth inhibitory agent. For example, the growth inhibitory agent may be administered first, followed by an antibody of the present invention. However, simultaneous administration or administration of the antibody of the present invention first is also contemplated. Suitable dosages for the growth inhibitory agent are those presently used and may be lowered due to the combined action (synergy) of the growth inhibitory agent and the antibody herein.

For the prevention or treatment of disease, the appropriate dosage of an anti-tumor agent, e.g., an antibody herein will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

For example, depending on the type and severity of the disease, about 1 g/kg to 15 mg/kg (e.g., 0.1-20 mg/kg) of antibody is an initial candidate dosage for administration to the patient, whether, for example, by one or more separate administrations, or by continuous infusion. A typical daily dosage might range from about 1 g/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

Q. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually an anti-tumor agent capable of interfering with the activity of a gene product identified herein, e.g., an antibody. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

R. Diagnosis and Prognosis of Tumors

While cell surface proteins, such as growth receptors overexpressed in certain tumors are excellent targets for drug candidates or tumor (e.g., cancer) treatment, the same proteins along with secreted proteins encoded by the genes amplified in tumor cells find additional use in the diagnosis and prognosis of tumors. For example, antibodies directed against the protein products of genes amplified in tumor cells can be used as tumor diagnostics or prognostics.

For example, antibodies, including antibody fragments, can be used to qualitatively or quantitatively detect the expression of proteins encoded by the amplified genes ("marker gene products"). The antibody preferably is equipped with a detectable, e.g., fluorescent label, and binding can be monitored by light microscopy, flow cytometry, fluorimetry, or other techniques known in the art. These techniques are particularly suitable, if the amplified gene encodes a cell surface protein, e.g., a growth factor. Such binding assays are performed essentially as described in section 5 above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va. In the following Examples, unless otherwise specified, "Sra6" will refer to native sequence PRO10282 polypeptide.

Example 1

Isolation of cDNA Clones Encoding a Human PRO10282 and PRO19578 polypeptides cDNA clones (DNA 148380-2827 and DNA 148389-2827-1) encoding native human PRO10282 and PRO19578 polypeptides were identified using a yeast screen, in a human fetal brain cDNA library that preferentially represents the 5' ends of the primary cDNA clones.

Clone DNA 148380-2827 contains a single open reading frame with an apparent translational initiation site at nucleotide positions 49-51 and ending at the stop codon at nucleotide positions 2050-2052 (FIG. 1). The predicted polypeptide precursor is 667 amino acids long (FIG. 2). The full-length PRO10282 protein shown in FIG. 2 has an estimated molecular weight of about 73502 daltons and a pI of about 9.26. Analysis of the full-length PRO10282 sequence shown in FIG. 2 (SEQ ID NO:2) evidences the presence of a variety of important polypeptide domains as shown in FIG. 2, wherein the locations given for those important polypeptide domains are approximate as described above. Clone DNA148380-2827 has been deposited with ATCC on Jan. 11, 2000 and is assigned ATCC Deposit No. PTA-1181.

Clone DNA148389-2827-1 contains a single open reading frame with an apparent translational initiation site at nucleotide positions 186-188 and ending at the stop codon at nucleotide positions 2160-2162 (FIG. 6, SEQ ID NO: 4). The predicted polypeptide precursor is 658 amino acids long (FIG. 7, SEQ ID NO: 5). The full-length PRO19578 protein shown in FIG. 7 has an estimated molecular weight of about 72583 daltons and a pI of about 9.36. Analysis of the full-length PRO19578 sequence shown in FIG. 7 (SEQ ID NO: 5) evidences the presence of a variety of important polypeptide domains as shown in FIG. 7, wherein the locations given for those important polypeptide domains are approximate as described above. Noteworthy is the presence of nine potential transmembrane domains and fourteen cysteine residues conserved between the human and the corresponding mouse sequence. While mouse Stra6 has three potential N-linked glycosylation sites, the human PRO19578 (native human Stra6) polypeptide has one. Clone 148389-2827-1 has been deposited with ATCC on Feb. 23, 2000, and is assigned ATCC Deposit No. PTA 1405.

An analysis of the Dayhoff database (version 35.45 SwissProt 35), using the ALIGN-2 sequence alignment analysis of the full-length sequence shown in FIG. 2 (SEQ ID NO:2), and of the full-length sequence shown in FIG. 7 (SEQ ID NO: 5) evidenced sequence identity between the PRO10282 amino acid sequence and the following Dayhoff sequences: AF062476, P_$_n$88559 and HGS_RE259.

As shown in FIG. 8, comparison of the full-length human PRO10282 and PRO19578 polypeptides shows that PRO19578 contains a deletion of nine amino acids (SPVDFLAGD; SEQ ID NO: 13) at positions 89-97 of the PRO10282 amino acid sequence. In addition, PRO19578 contains an isoleucine (I) at amno acid position 518 in place of methionine (M) at the corresponding position (position 527) of PRO10282, which results from a G/A polymorphism at this position. Both the PRO10282 and the native sequence PRO19578 polypeptides are believed to be the human homologues of the mouse Stra6 polypeptide, and are, therefore, also referred to as "Stra6." Mouse Stra6 and the native sequence human full-length PRO10282 polypeptide encoded by DNA 148340-2827 show about 74% amino acid sequence identity.

FIG. 9 shows the hydrophobicity plot of the native sequence human full-length PRO10282 polypeptide encoded by DNA 148380-2827, briefly referred to as "human Stra6." As shown in FIG. 9, about 50% of the amino acid residues in this 667 amino acids long polypeptide are hydrophobic.

The human Stra6 gene was localized to chromosome 15q23 as determined by UNIGENE. Preliminary fine mapping indicates that Stra6 is located in the STS interval D15S124-D15S160 and the GeneMap'98 position corresponds to 244.52 on the G3 map.

Example 2

Use of PRO10282 and PRQ19578 as a Hybridization Probe

The following method describes use of a nucleotide sequence encoding PRO10282 and PRO19578 as a hybridization probe.

DNA comprising the coding sequence of full-length or mature PRO10282 or PRO19578 is employed as a probe to screen for homologous DNAs (such as those encoding naturally-occurring variants of PRO10282 or PRO19578) in human tissue cDNA libraries or human tissue genomic libraries.

Hybridization and washing of filters containing either library DNAs is performed under the following high stringency conditions. Hybridization of radiolabeled PRO10282-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO10282 or PRO19578 can then be identified using standard techniques known in the art.

Example 3

Expression of PRO10282 and PRO19578 in *E. coli*

This example illustrates preparation of an unglycosylated form of PRO10282 or PRO19578 by recombinant expression in *E. coli*.

The DNA sequence encoding PRO10282 or PRO19578 is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al. *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO10282 or PRO19578 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in die art, and the solubilized PRO10282 protein can then be purified using a metal chelating column under conditions that allow tight binding of the protein.

PRO10282 or PRO19578 may be expressed in *E. coli* in a poly-His tagged form, using the following procedure. The DNA encoding PRO10282 or PRO19578 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D. 600 of 3-5 is reached. Cultures are then diluted 50-100 fold into CRAP media (prepared by mixing 3.57 g $(NH_4)_2SO_4$, 0.71 g sodium citrate 2H2O, 1.07 g KCl, 5.36 g Difco yeast extract, 5.36 g Sheffield hycase SF in 500 ml. water, as well as 110 mM MPOS. pH 7.3, 0.55% (w/v) glucose and 7 mM $MgSO_4$) and grown for approximately 20-30 hours at 30° C. with shaking. Samples are removed to verity expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentrifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO10282 or PRO19578 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Specifically, two extracellular domains (ECD) of the native human Stra6 protein PRO10282, Pepetide A (amino acids 229-295) and Peptide B (amino acids 532-667) were expressed separately as peptides in the *E. coli* cytoplasm with an N-terminal polyhistidine leader having the amino acid sequence MKHQHQHQHQHQHQMHQ (SEQ-ID NO: 12). This leader provides for optimal translation initiation, purification on a nickel chelation column, and efficient removal if desired with the TAGZyme system (Unizyme Laboratories). Transcription was controlled by the *E. coli* alkaline phosphatase promoter (Kikuchi et al., *Nucleic Acids Res.* 9:5671-5678 [1981]) and the trp operon ribosome binding site (Yanofsky et al., *Nucleic Acids Res.* 9:6647-6668 [1981]) provided for translation. Downstream of the translation termination codon, is the λ to transcriptional terminator (Scholtissek and Grosse, *Nucleic Acids Res.* 15:3185 [1987]) followed by the rare codon tRNA genes pro2, argU, and glyT (Komine et al., *J. Mol. Biol.* 212:579-598 [1990]; Fournier and Ozeki, *Microbiol. Rev.* 49:379-397 [1985]).

The two Stra6 ECD coding sequence DNA fragments were prepared by PCR from a full length cDNA clone, and inserted into the expression vector described above, which was designated as pST239. After DNA sequence verification, the new Stra6 expression plasmids, designated PE148380A and PE148380B, were transformed into the *E. coli* strain 58F3 ((fhuAΔ(tonAΔ) lonΔ galE rpoHts (htpRts) ΔclpP lacIq ΔompTΔ (nmpc-fepE) ΔslyD). Luria Broth cultures of these transformants were first grown overnight at 30° C., and then diluted 100 fold into a phosphate limiting media to induce the alkaline phosphatase promoter. After 24 hours at 30° C. with shaking, the cultures were centrifuged, and the cell pastes frozen until the start of peptide purification.

For purification, *E. coli* pastes (6-10 gm pellets) were resuspended in 10 volumes (w/v) of 7 M guanidine HCl, 20 mM Tris. pH 8, buffer. Solid sodium sulfite and sodium tetrathionate were added to make final concentrations of 0.1 M and 0.02 M, respectively, and the solution was stirred overnight at 4° C. The solution was clarified by centrifugation and loaded onto a Qiagen Ni-NTA metal chelate column equilibrated in 6 M guanidine, HCl, 20 mM Tris, pH 7.4. The column was washed with additional buffer containing 50 mM imidazole (Calbiochem, Utrol grade). The protein was eluted with buffer containing 250 mM imidazole. Fractions containing the desired protein were pooled, dialyzed against 1 mM HQ and stored at 4° C.

Example 4

Expression of PRO10282 and PRO19578 in Mammalian Cells

This example illustrates preparation of a potentially glycosylated form of PRO10282 and PRO19578 by recombinant expression in mammalian cells.

The vector, pRK5 (see EP 307,247, published Mar. 15, 1989), is employed as the expression vector. Optionally, the PRO10282 or PRO19578 DNA is ligated into pRK5 with selected restriction enzymes to allow insertion of the PRO10282 DNA using ligation methods such as described in Sambrook et al., supra. The resulting vector is called pRK5-PRO10282 and pRK5-PRO19578, respectively.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 g pRK5-PRO10282 or pRK5-PRO19578 DNA is mixed with about 1 g DNA encoding the VA RNA gene [Thimmappaya et al., *Cell*, 3L543 (1982)] and dissolved in 500 l of 1 mM Tris-HCl, 0.1 mM EDTA, 0.227 M $CaCl_2$. To this mixture is added, dropwise, 500 l of 50 mM HEPES (pH 7.35), 280 mM NaQ, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 Ci/ml $^{35}$S-cysteine and 200 Ci/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO10282 polypeptide. The cultures containing transfected cells may undergo further incubation (in serum free medium) and the medium is tested in selected bioassays.

In an alternative technique, PRO10282 or PRO19578 may be introduced into 293 cells-transiently using the dextran sulfate method described by Somparyrac et al., *Proc. Natl. Acad. Sci.*, 12:7575 (1981). 293 cells are grown to maximal density in a spinner flask and 700 g pRK5-PRO10282 or pRK5-PRO19578 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 g/ml bovine insulin and 0.1 g/ml bovine transferrin. After about four days, the conditioned media is centrifuged and filtered to remove cells and debris. The sample containing expressed PRO10282 or PRO19578 can then be concentrated and purified by any selected method, such as dialysis and/or column chromatography.

In another embodiment, PRO10282 or PRO19578 can be expressed in CHO cells. The pRK5-PRO10282 or pRK5-PRO19578 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO10282 or PRO19578 polypeptide, the culture medium may be replaced with serum free medium. Preferably, the cultures are incubated for about 6 days, and then the conditioned medium is harvested. The medium containing the expressed PRO10282 or PRO19578 can then be concentrated and purified by any selected method.

Epitope-tagged PRO10282 or pRO19578 may also be expressed in host CHO cells. The PRO10282 or PRO19578 may be subcloned out of the pRK5 vector. The subclone insert can undergo PCR to fuse in frame with a selected epitope tag such as a poly-his tag into a Baculovirus expression vector. The poly-his tagged PRO10282 or PRO19578 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO10282 or PRO19578 can then be concentrated and purified by any selected method, such as by $Nr^{2+}$-chelate affinity chromatography.

PRO10282 or PRO19578 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3 \times 10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout die production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 5

Expression of PRO10282 and PRO19578 in Yeast

The following method describes recombinant expression of PRO10282 and PRO19578 in yeast.

First, yeast expression vectors are constructed for intracellular production or secretion of PRO10282 polypeptides from the ADH2/GAPDH promoter. DNA encoding a PRO10282 polypeptide (including PRO19578) and the promoter is inserted into suitable restriction enzyme sites in the selected plasmid to direct intracellular expression of PRO10282. For secretion, DNA encoding PRO10282 can be cloned into the selected plasmid, together with DNA encoding the ADH2/GAPDH promoter, a native PRO10282 signal peptide or other mammalian signal peptide, or, for example, a yeast alpha-factor or invertase secretory signal/leader sequence, and linker sequences (if needed) for expression of PRO10282.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO10282 (including PRO19578) can subsequently be isolated and purified by removing the yeast cells from the fermentation medium by centrifugation and then concentrating the medium using selected cartridge filters. The concentrate containing PRO10282 (e.g. PRO19578) may further be purified using selected column chromatography resins.

Example 6

Expression of PRO10282 and PRO19578 in Baculovirus-Infected Insect Cells

The following method describes recombinant expression of PRO10282 and PRO19578 in Baculovirus-infected insect cells.

The sequence coding for PRO10282 or PRO19578 is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO10282 or PRO19578 or the desired portion of the coding sequence of PRO10282 or PRO19578, such as the sequence encoding the extracellular domain of a transmembrane protein or the sequence encoding the mature protein if the protein is extracellular, is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO10282 or PRO19578 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer.

One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO10282 or PRO19578 are pooled and dialyzed against loading buffer.

Alternatively, purification of the IgG tagged (or Fc tagged) PRO10282 or PRO19578 can be performed using known chromatography techniques, including for instance, Protein A or protein G column chromatography.

Example 7

Preparation of Antibodies that Bind PRO10282 or PRO19578

This example illustrates preparation of monoclonal antibodies which can specifically bind PRO10282 or PRO19578.

Techniques for producing the monoclonal antibodies are known in the art and are described, for instance, in Goding, supra. Immunogens that may be employed include purified PRO10282 and PRO19578, fusion proteins containing PRO10282 or PRO19578, and cells expressing recombinant PRO10282 or PRO19578 on the cell surface. Selection of the immunogen can be made by the skilled artisan without undue experimentation.

Mice, such as Balb/c, are immunized with the PRO10282 or PRO19578 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO10282 antibodies or anti-PRO19578 antibodies.

After a suitable antibody titer has been detected, the animals "positive" for antibodies can be injected with a final intravenous injection of PRO10282 or PRO19578. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO10282 or PRO19578. Determination of "positive" hybridoma cells secreting the desired monoclonal antibodies against PRO10282 or PRO19578 is within the skill in the art.

The positive hybridoma cells can be injected intraperitoneally into syngeneic Balb/c mice to produce ascites containing the anti-PRO10282 or anti-PRO19578 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Specifically, five Balb/c mice (Charles River Laboratories, Wilmington, Del.) were hyper-immunized with purified Unizyme-conjugated amino acid peptide, corresponding to amino acids 532-667 of human Stra6, in Ribi adjuvant (Ribi Immunochem Research, Inc., Hamilton, Mo.). B-cells prepared from popliteal lymph nodes were fused with mouse myeloma cells (X63.Ag8.653; American Type Culture Collection, Manassas, Va.) as previously described (Hongo et al., *Hybridoma* 14:253-260 [1995]). After 10-14 days, supernatants were harvested and screened for antibody production by direct enzyme-linked immunosorbant assay (ELISA). Eight positive clones, showing the highest immunobinding by direct ELISA and immunohistochemistry after two rounds of subcloning by limiting dilution, were injected into Pristine-primed mice for in vivo production of mAb (Freud and Blair; 1. *Immunol*. 129:2826-2830 [1982]). The ascites fluids were pooled and purified by Protein A affinity chromatography (Pharmacia fast protein liquid chromatography (FPLC); Pharmacia, Uppsala, Sweden) as previously described (Hongo et al., supra). The purified antibody preparations were sterile filtered (0.2 μm pore size; Nalgene, Rochester, N.Y.) and stored at 4° C. in phosphate buffered saline (PBS).

Example 8

Purification of PRO10282 and PRO19578 Polypeptides Using Specific Antibodies

Native or recombinant PRO10282 and PRO19578 polypeptides may be purified by a variety of standard techniques in the art of protein purification. For example, pro-PRO10282 or pro-PRO19578 polypeptide, mature PRO10282 or PRO19578 polypeptide, or pre-PRO10282 or pre-PRO19578 polypeptide is purified by immunoaffinity chromatography using antibodies specific for the PRO10282 polypeptide of interest. In general, an immunoaffinity column is constructed by covalently coupling the anti-PRO10282 or anti-PRO19578 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO10282 or PRO19578 polypeptide by preparing a fraction from cells containing PRO10282 or PRO19578 polypeptide in a soluble form. This preparation is derived by solubilization of the whole cell or of a subcellular fraction obtained via differential centrifugation by the addition of detergent or by other methods well known in the art. Alternatively, soluble PRO10282 or PRO19578 polypeptide containing a signal sequence may be secreted in useful quantity into the medium in which the cells are grown.

A soluble PRO10282 or PRO19578 polypeptide-containing preparation is passed over the immunoaffinity column, and the column is washed under conditions that allow the preferential absorbance of PRO10282 or PRO19578 polypeptide (e.g., high ionic strength buffers in the presence of detergent). Then, the column is eluted under conditions that disrupt antibody/PRO10282 or PRO19578 polypeptide binding (e.g., a low pH buffer such as approximately pH 2-3, or a high concentration of a chaotrope such as urea or thiocyanate ion), and PRO10282 or pRO19578 polypeptide is collected.

Example 9

Drug Screening

This invention is particularly useful for screening compounds by using PRO10282 (Stra6) polypeptides (including PRO19578) or binding fragment thereof in any of a variety of drug screening techniques. The PRO10282 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO10282 polypeptide or fragment. Drugs are screened against such transformed cells in competitive binding assays. Such cells, either in viable or fixed form, can be used for standard binding assays. One may measure, for example, the formation of complexes between PRO10282 polypeptide or a fragment and the agent being tested. Alternatively, one can examine the diminution in complex formation between the PRO10282 polypeptide and its target cell or target receptors caused by the agent being tested.

Thus, the present invention provides methods of screening for drugs or any other agents which can affect a PRO10282 (Stra6) polypeptide-associated disease or disorder. These methods comprise contacting such an agent with a Stra6 polypeptide or fragment thereof and assaying (i) for the presence of a complex between the agent and the Stra6 polypeptide or fragment, or (ii) for the presence of a complex between the Stra6 polypeptide or fragment and the cell, by methods well known in the art. In such competitive binding assays, the Stra6 polypeptide or fragment is typically labeled. After suitable incubation, free Stra6 polypeptide or fragment is separated from that present in bound form, and the amount of free or uncomplexed label is a measure of the ability of the particular agent to bind to Stra6 polypeptide or to interfere with the Stra6 polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO10282 (Stra6) polypeptide, the peptide test compounds are reacted with Stra6 polypeptide and washed. Bound Stra6 polypeptide is detected by methods well known in the art. Purified Stra6 polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding a Stra6 polypeptide specifically compete with a test compound for binding to a Stra6 polypeptide or fragments thereof. In this manner, the antibodies can be used to detect the presence of any peptide which shares one or more antigenic determinants with the Stra6 polypeptide.

Example 10

Rational Drug Design

The goal of rational drug design is to produce structural analogs of biologically active polypeptide of interest (i.e., a PRO10282 (Stra6) polypeptide) or of small molecules with which they interact, e.g., agonists, antagonists, or inhibitors. Any of these examples can be used to fashion drugs which are more active or stable forms of the native sequence PRO10282 polypeptide or PRO19578 polypeptide, or which enhance or interfere with the function of the native sequence PRO10282 or PRO19578 polypeptide in vivo (c.f., Hodgson, *Bio/Technology*, 9: 19-21 (1991)).

In one approach, the three-dimensional structure of the native sequence PRO10282 or PRO19578 polypeptide, or of a PRO10282 or PRO19578 polypeptide-inhibitor complex, is determined by x-ray crystallography, by computer modeling or, most typically, by a combination of the two approaches. Both the shape and charges of the native PRO10282 or PRO19578 polypeptide must be ascertained to elucidate the structure and to determine active site(s) of the molecule. Less often, useful information regarding the structure of the PRO10282 or PRO19578 polypeptide may be gained by modeling based on the structure of homologous proteins. In both cases, relevant structural information is used to design analogous PRO10282 polypeptide-like molecules or to identify efficient inhibitors. Useful examples of rational drug design may include molecules which have improved activity or stability as shown by Braxton and Wells, *Biochemistry*, 3L7796-7801 (1992) or which act as inhibitors, agonists, or antagonists of native peptides as shown by Athauda et al., *J. Biochem.*, 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO10282 polypeptides (including PRO19578) may be made available to perform such analytical studies as X-ray crystallography. In addition, knowledge of the PRO10282 polypeptide amino acid sequences provided herein will provide guidance to those employing computer modeling techniques in place of or in addition to x-ray crystallography.

Example 11

Tissue Expression Distribution

Oligonucleotide probes were constructed from the PRO10282 polypeptide-encoding nucleotide sequence shown in the accompanying figures for use in quantitative PCR amplification reactions. The oligonucleotide probes were chosen so as to give an approximately 200-600 base pair amplified fragment from the 3' end of its associated template in a standard PCR reaction. The oligonucleotide probes were employed in standard quantitative PCR amplification reactions with Clontech RNA isolated from different adult human tissue sources and analyzed by agarose gel electrophoresis so as to obtain a quantitative determination of the level of expression of the PRO10282 polypeptide-encoding nucleic acid in the various tissues tested. Knowledge of the expression pattern or the differential expression of the PRO10282 polypeptide-encoding nucleic acid in various different human tissue types provides a diagnostic marker useful for tissue typing, with or without other tissue-specific markers, for determining the primary tissue source of a metastatic tumor, and the like. The results of these assays (shown in FIG. 10) demonstrated that the DNA 148380-2827 molecule is highly expressed in the adult kidney, testis and uterus; significantly expressed in breast, prostate and trachea; weakly expressed in brain, heart, lung and thymus; and not expressed in liver, bone marrow, colon, skeletal muscle, small intestine, spleen and stomach.

Total RNA was purchased from Clontech (Palo Alto, Calif.) and analyzed using the following primer/probe set for PCR amplification:

```
                                                (SEQ ID NO: 6)
h.Stra6.tmf3:
5' CACACTCGAGAGCCAGATATTTT (SEQ ID NO: 7)
h.Stra5.tmr4:
5' AACAAGTTTATTGCAGGGAACAC (SEQ ID NO: 8)
h.Stra6.tmp4:
5' TGTAGTTTTTATGCCTTTGGCTATTATGAAAGAGGT
``` tmf=forward primer
tmr=reverse primer
tmp=probe

In situ hybridization, performed as described in Example 12 below, confirmed Stra6 expression in kidney tubular epithelial cells, myometrium, and stromal cells surrounding breast ducts and lobules, whereas little or no expression was detected in sections of brain, liver, spleen, pancreas, heart, lung, stomach, small intestine, colon, prostate, spleen, and adrenal cortex (data not shown). Of the normal tissues examined by in situ hybridization, highest expression levels were seen in placenta and adrenal medulla, which were not included in the PCR analysis.

Example 12

Over-expression of Native Human PRO10282 (Stra6) Transcript in Human Tumors

This example shows that the gene encoding native human full-length PRO10282 (Stra6) is significantly over-expressed in certain human colon tumors and also in cell lines derived from various human tumors such as colon, lung, kidney and breast.

The starting material for the screen was total RNA isolated from human colon tumors, or various human colon, kidney, breast, or lung tumor cell lines. In colon tumor tissue, Stra6 RNA expression was determined relative to RNA from normal colon tissue (mucosa) from the same patient. Stra6 RNA expression in various tumor cell lines was determined in comparison with various normal cell lines (i.e., normal colon, kidney and lung cell lines).

Real-time quantitative PCR (RT-PCR, for example, TAQMAN ABI PRIZM 7700™ Sequence Detection System™ [Perkin Elmer, Applied Biosystems Division, Foster City, Calif.]), was used to monitor quantitative differences in the level of expression of the PRO10292 (Stra6) encoding gene (corresponding to DNA 148380-2827) in normal cells and cells derived from certain cancers or cancer cell lines, using Taqman assay reagents. 50 µl RT-PCR reactions consisted of 5 µl p. 10× Taqman Buffer A, 300 µM of each dNTF, 5 mM MgCl$_2$, 10 units of RNAse inhibitor, 12.5 units of MuLV Reverse Transcriptase, 1.25 units of AmpliTaq Gold DNA Polymerase, 200 nM probe, 500 nM primers and 100 ng RNA. Reaction conditions consisted of reverse transcription at 48° C. for 30 minutes, denaturation at 95° C. for 25 seconds and 65° C. for one minute. Reaction products were analyzed on 4-20% polyacrylamide gels (Novex).

Standard curves were used to determine relative levels of expression for each gene of interest as well as the glyceraldehyde-3-phosphate dehydrogenase (GAPDH) housekeeping gene for each sample analyzed. Relative normalized units were obtained by dividing the gene of interest mRNA level by the GAPDH mRNA level. Relative normalized units were compared between experimental sample and control to determine fold induction.

The results were used to determine whether the mRNA encoding PRO10282 is over-expressed in any of the primary colon cancers or colon, kidney, breast, or lung cancer cell lines that were screened. The histology of some matched human normal and colon tumor samples used for the analysis (see FIGS. 11 and 12) is shown below:

| Number | Histology |
|---|---|
| 850 | Invasive adenocarcinoma; no necrosis; good preservation. |
| 851 | Invasive adenocarcinoma; minimal necrosis; good condition. |
| 892 | Invasive adenocarcinoma; minimal necrosis; good condition. |
| 869 | Invasive adenocarcinoma; minimal necrosis; good condition. |
| 893 | Normal mucosa - dysplasia - invasive adenocarcinoma; minor necrosis; good condition. |
| 870 | Adenocarcinoma - severe dysplasia; minimal necrosis; good condition. |
| 871 | Adenocarcinoma - dysplasia - normal mucosa; no necrosis; good condition. |
| 848 | Adenocarcinoma - appears to be arising in villous adenoma; normal mucosa/submucosa; no necrosis, good condition. |
| 872 | Invasive adenocarcinoma; about 70% of tumor is necrotic; overall good preservation. |
| 778 | Adenocarcinoma - unusually papillary morphology; normal/hyperplastic mucosa; minimal necrosis; acceptable preservation. |
| 17 | Moderately well-differentiated adenocarcinoma. |
| 18 | Well-differentiated adenocarcinoma. |
| 64 | Moderately well-differentiated adenocarcinoma. |
| 76 | Moderately well-differentiated adenocarcinoma. |

Human lung cell lines include the normal human lung fibroblast cell lines MRC5 (CCL-171) and IMR90 (CCL-186), the human lung carcinoma epithelial cell line A549 (SRCC768, CCL-185), the human epidermoid lung carcinoma cell line Calu-1 (SRCC769; HTB-54), the human anaplastic carcinoma cell line Calu-6 (SRCC770, HTB-56— probably lung), the human epithelial cell line NCI-H441 (SRCC772; HTB-174) which was derived from pericardial fluid of a patient with papillary adenocarcinoma of the lung, and the human lung squamous cell carcinoma cell line SW900 (SRCC775; HTB-59), all available from ATCC.

Colon cell lines include, for example, the normal colon fibroblast cell line CCD112Co (CRL-1541), the human colorectal adenocarcinoma cell line CaCo-2 (HTB-37), the human colorectal adenocarcinoma cell line WiDr (CCL-218), the human colorectal carcinoma cell line HCT116(CCL-247), the human colorectal adenocarcinoma cell line SK– Col (HTB-39), the human colorectal adenocarcinoma cell line COLO320 (SRCC778; CCL-220), the human colorectal adenocarcinoma cell line HT29 (SRCC779; HTB-38), the human colorectal adenocarcinoma cell line SW403 (CCL-230), the human colon cancer cell line NCI/HCC2998, and the human colorectal adenocarcinoma cell line Colo320DM (CCL-220), all available from ATCC or other public sources.

Human breast carcinoma cell lines include the human breast adenocarcinoma cell line MCF7 (SRCC766; HTB-22), and the human breast cancer cell line NCI/ADR-RES, both of which are publicly available.

Kidney lines include the 293 cell line (CRL-1573) which is transformed with adenovirus 5 DNA. Two Wilm's tumor cell lines were also included in die analysis, G401 (CRL-1441) and SK-NEP-1 (CRL-1573).

RNA Preparation:

RNA was prepared from the foregoing cultured cell lines. The isolation was performed using purification kit, buffer set and protease from Qiagen, according to the manufacturer's instructions and the description below. More specifically, total RNA from cells in culture was isolated using Qiagen RNeasy midi-columns. Total RNA from tissue samples was isolated using RNA Stat-60 (Tel-Test). RNA prepared from tumor was isolated by cesium chloride density gradient centrifugation.

Solid Human Tumor Sample Preparation and Lysis:

Tumor samples were weighed and placed into 50 ml conical tubes and held on ice. Processing was limited to no more than 250 mg tissue per preparation (1 tip/preparation). The protease solution was freshly prepared by diluting into 6.25 ml cold ddH$_2$O to a final concentration of 20 μg/ml and stored at 4° C. G2 buffer (20 ml) was prepared by diluting DNAse A to a final concentration of 200 μg/ml (from 100 mg/ml stock). The tumor tissue was homogenized in 10 ml G2 buffer for 60 seconds using the large tip of the polytron in a laminar-flow TC hood in order to avoid inhalation of aerosols, and held at room temperature. Between samples, the polytron was cleaned by spinning at 2×30 seconds each in 2 L, ddH$_2$O, followed by G2 buffer (50 ml). If tissue was still present on the generator tip, the apparatus was disassembled and cleaned.

Qiagen protease (prepared as indicated above, 1.0 ml) was added, followed by vortexing and incubation at 50° C. for 3 hours. The incubation and centrifugation were repeated until the lysates were clear (e.g., incubating additional 30-60 minutes, pelleting at 3000×g for 10 minutes, 4° C.).

Quantitation

The results obtained from the real-time PCR analysis of RNA were initially expressed as delta CT units. One unit corresponds to one PCR cycle or approximately a 2-fold amplification relative to normal, two units correspond to 4-fold, 3 units to 8-fold amplification and so on. The data is converted to fold difference and presented as such. Initially, reverse transcriptase was used to synthesize cDNA from 100 ng total RNA or polyA+ RNA using oligo(dT) as a primer. The resultant cDNA was then used as a template for PCR. Quantitation was obtained using primers derived from the 3'-untranslated regions of the PRO10282 encoding sequence and a TAQMAN™ fluorescent probe corresponding to the respective intervening sequences. Using the 3' region tends to avoid crossing intron-exon boundaries in the genomic DNA, an essential requirement for accurate assessment of RNA expression using this method. The sequences for the primers and probes (forward, reverse, and probe) using for the PRO10282 encoding gene amplification were as follows:

One set included the forward and reverse primers and probe described in Example 11 above as SEQ ID Nos: 6, 7 and 8, respectively.

Another set included:

h.Stra6.tmfl1:
5' AGACCAGGTCCCACACTGA          (SEQ ID NO: 9)

hStra6.tmr1:
5' TTCATAATAGCCAAAGGCATAAAA,    (SEQ ID NO: 10)
and h.Stra6.tmp1:
5' CTGCCCACACTCGAGAGCCAGAT 3'   (SEQ ID NO: 11)

Human GAPDH:

forward primer:
5'-GAAGATGGTGATGGGATTTC-3'      (SEQ ID NO: 14)

reverse primer;
5'-GAAGGTGAAGGTCGGAGTC-3'       (SEQ ID NO: 15)

probe:
5'-CAAGCTTCCCGTTCTCAGCC-3'      (SEQ ID NO: 16)

The 5' nuclease assay reaction is a fluorescent PCR-based technique which makes use of the 5' exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

As noted above, the 5' nuclease procedure is run on a real-time quantitative PCR device such as the ABI PRIZM 7700™ Sequence Detection System™. The system consists of a thermocyler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. This is defined as the cycle at which the reporter signal accumulates above the background level of fluorescence. The Ct values are used as quantitative measurement of the relative number of starting copies of a particular target sequence in a nucleic acid sample when comparing the expression of RNA in a cancer cell with that from a normal cell.

Results

The human Stra6 RNA (corresponding to DNA 148380-2827) shows strong over-expression in human colon tumor tissues, when compared with corresponding normal human colon tissues. As shown in FIG. 11, human Stra6 RNA (corresponding to DNA148380-2827) was found to be over-expressed in all 14 human tumor colon tissues examined, relative to RNA from matched normal colorectal mucosa from the same patient. The over-expression varied between two- and 170-fold, and in 7 out of 14 tumor tissue samples was at least about 10-fold. The cycle threshold values obtained by quantitative PCR indicated that Stra6 mRNA levels were extremely low or possibly absent in many of the normal mucosa samples.

As a second method of detection, the products obtained after completion of the quantitative PCR reactions (40 cycles each) were subjected to electrophoresis in polyacrylamide gels and visualized by ethidium bromide staining. As shown in FIG. 12A, using expression of a housekeeping gene, glyceraldehyde 3-phosphate dehydrogenase (GAPDH) as the standard, substantially greater amounts of PCR products were generated off Stra6 mRNA in tumor samples compared to their normal counterparts. By contrast, a comparable level of product from the internal control GAPDH mRNA was generated from all samples.

Stra6 expression in colon adenocarcinomas was localized to the epithelial tumor cells by in situ hybridization (ISH) performed as follows. $^{32}$P-labeled sense and antisense riboprobes were transcribed from an 874 bp PCR product corresponding to nucleotides 432-1247 of the coding sequence of human Stra6 polypeptide encoded by DNA 148380-2827. Formalin-fixed, paraffin-embedded tissue sections were processes as described previously (Pennica et al., *Proc. Natl. Acad. Sci. USA* 95:14717-22 [1998]). The results are shown in FIG. 12B.

As shown in FIG. 13, the human Stra6 RNA (corresponding to DNA 148380-2827) is also significantly over-expressed in various breast, kidney, colon and lung tumor cell lines. "Relative RNA Expression" means that the RNA expression in normal and tumor tissues is shown relative to expression in an arbitrarily chosen standard cell line SW480.

In situ hybridization results obtained in various tumor sections are also shown in FIG. 16. Several tumor types other than colon adenocarcinomas also showed high levels of Stra6 expression. These included 3 of 3 melanomas (FIGS. 16A and B), 3 of 4 endometrial adenocarcinomas (FIGS. 16C and D), 2 of 3 ovarian adenocarcinomas, and a Wilm's tumor of the kidney (FIGS. 16E and F). The Stra6 in situ hybridization signal in these various tumors was considerably greater than in colon adenocarcinomas consistent with data showing relatively high expression levels in normal kidney and uterus and low levels in normal colon. Since Stra6 was detected in normal adrenal medulla, we also examined two pheochromocytomas, which are tumors derived from this tissue. In these tumors, Stra6 expression exceeded that of any other tumor or tissue examined in this study (FIGS. 16G and H). Although Stra6 was detected in normal kidney and was strongly expressed in Wilm's tumor, it was not detected in renal cell carcinomas. In kidney transitional cell carcinomas, tumor-associated stromal cells rather than tumor epithelial cells expressed Stra6 (data not shown).

Because mRNA DNA 148380-2827 encoding PRO10282 is overexpressed in various tumors as well as in a number of tumor derived cell lines, it is likely associated with tumor formation and/or growth. As a result, antagonists (e.g., antibodies, organic and inorganic small molecules, peptides and polypeptides, such as Stra6 variants, antisense oligonucleotides) directed against the protein encoded by DNA148380-2827 (PRO10282) or other naturally occurring variants of this protein, such as PRO19578 encoded by DNA148389-2827-1, are expected to be useful in diagnosis, prevention and/or treatment of cancer particularly, without limitation, colon, lung, breast and/or kidney cancer.

The efficacy of antagonists such as therapeutic antibodies directed against the protein encoded by DNA 148380-2827 (PRO10282) could be enhanced by agents that stimulate the expression of the gene encoding PRO10282. For example, treatment of human colorectal cancer cell lines with 9-cis-retinoic acid or all-trans retinoic acid resulted in a dramatic enhancement of the expression of the Stra6 mRNA (FIG. 15). Thus, the treatment of cancer patients with therapeutic antibodies directed against PRO10282 in combination with the appropriate retinoids would be expected to enhance tumor killing by the antibodies. The same will be true to antibodies directed against other native Stra6 polypeptides over-expressed in various tumors, such as the human splice variant encoded by DNA 148389-2827-1.

Example 13

Synergistic Induction of Stra6 by Wnt-1 and Retinoids

Materials and Methods

Cell Culture

C57MG and C57MG/Wnt-1 cells were grown in Dulbecco's Modified Eagle medium supplemented with 10% fetal bovine serum, 2 mM L-glutamine, and 2.5 µg/ml puromycin (Edge Biosystems). C57MG cells with tetracycline-repressible Wnt-1 expression were grown in complete medium without puromycin, supplemented with 400 µg/ml G418 (Gibco BRL), 100 µg/ml hygromycin B (Gibco BRL), and 50 ng/ml tetracycline (Korinek et al., *Mol. Cell. Biol.* 18:1248-56 [1998]). For Wnt-1 induction studies, cells were washed with phosphate buffered saline, cultured in tetracycline-free media for 10, 24, 48, 72, and 96 hours and then harvested. A 0-hour control dish was maintained entirely in media containing tetracycline. All dishes were simultaneously harvested and total RNA was extracted for each time point. RT-PCR was carried out with Wnt-1, Stra6, and GAPDH specific primers and probes on 100 ng total RNA from each sample.

Human colon adenocarcinoma cell lines HCT116 and WiDr cells were obtained from the American Type Culture Collection. HCT116 cells were maintained in McCoy's 5A media supplemented with 10% fetal bovine serum (FBS). WiDr cells were maintained in Dulbecco's minimal essential media (DMEM) supplemented with 10% FBS. For retinoic acid induction studies, cells were plated at $10^5$ cells/60 mm dish containing 2.5 ml of medium and allowed to grow for 24 hours. Cells were treated with Vitamin D3, all-/trans-RA (Spectrum Laboratory Products), or 9-m-RA (Toronto Research Chemicals Inc.) (1 µM final concentration in DMSO) for the indicated times. Control cells were treated with an equal volume of DMSO.

For the treatment of C57MG/Parent cells with Wnt-3a conditioned media, cells were incubated in regular media or conditioned media from L-cells or L-W3A cells in the presence or absence of 1 µM 9-cis-RA. Conditioned media was prepared as previously described (Willert et al. *Genes Dev.* 13:1768-73 [1999]). At 48 hours, cells were harvested by scraping into PBS containing sodium fluoride and vanadate and quick frozen in liquid nitrogen. RNA was prepared using the RNAeasy kit (Qiagen), including the additional DNaseI treatment on the columns according to manufacturer's instructions.

Western Blotting

For the C57MG/Wnt-1 TET cell line, Wnt-1 expression was induced by culturing cells in the absence of tetracycline for 0, 24, 48, or 72 hours. Cells were lysed in Triton X-100 lysis buffer [20 mM tris-HCl (pH 8.0), 137 mM NaCl, 1% Triton X-100, 1 mM EGTA, 10% glycerol, 1.5 mM $MgCl_2$, 1 mM dithiothreitol, 1 mM sodium vanadate, 50 mM sodium fluoride, and complete protease inhibitor cocktail (Boehringer Mannheim) and protein-equivalents were subjected to SDS-PAGE and immunoblotting. Blots were incubated with either 0.2 µg/ml affinity purified rabbit polyclonal antibody against β-catenin (Rubinfeld et al., Science 262:1731-1734 [1993]), 0.1 µg/ml anti-ERK2 monoclonal antibody (Transduction Laboratories), or 1:2000 rabbit polyclonal antisera against RARγ-1 (Affinity Bioreagents). For the WiDr cell line, cells were treated with 1 µM all-trans-RA for 48 hours and then lysed in Triton X-100 lysis buffer and processed as indicated above. Blots were incubated with 1:50 anti-Stra6 peptide B monoclonal hybridoma culture supernatant (clone 12F4.2H9.1D5).

Immunohistochemistry

WiDr cells were treated with 9-c/5-retinoic acid or DMSO, then detached and pelleted by low-speed centrifugation. Cell pellets were fixed overnight in 10% neutral buffered formalin, dehydrated, and embedded in paraffin. Immunohistochemistry was performed using anti-Stra6 peptide B monoclonal hybridoma culture supernatant (clone 12F4.2H9.1D5) or nonspecific mouse isotype IgG2A as primary antibodies, followed by detection using avidin-biotin complex method with diaminobenzidine as chromogen (Vectastain Elite Kit, Vector Laboratories) as described previously (Eberhard et al. Am. J. Pathol. 145:640-9 [1994]). Sections were counterstained with hematoxylin.

Wnt-1 Transgenic Mice

Transgenic mice that express the Wnt-1 proto-oncogene in the mammary gland typically exhibit hyperplastic lesions and develop neoplasms in this tissue (Tsukamoto et al., Cell 55:619-625 [1988]). Such mice were used in the following experiments.

Results

Easwaran et al. previously reported enhanced activation of a synthetic retinoic acid responsive reporter gene when MCF-7 cells were co-transfected with mutant (3-catenin and treated with retinoids (Easwaran et al., Curr. Biol. 9:1415-1418 [1999]). Considering this, together with the original identification of Stra6 as a retinoic acid inducible gene (Bouillet et al., Mech Dev. 63:173-186 [1997]), we asked whether retinoic acid could synergize with Wnt-1 to increase the level of Stra6 in the C57MG cell line. Treatment of parental C57MG cells with either 9-cis-RA or all-trans-RA (ATRA) for 48 hours significantly increased the level of Stra6 mRNA while DMSO and vitamin D3 had no effect (FIG. 17A). As expected, the C57MG/Wnt-1 cells treated with either DMSO or vitamin D3 exhibited enhanced levels of Stra6 mRNA relative to the parent cell line. The level of Stra6 induction by Wnt-1 was comparable to that observed on stimulation of the parental C57MG cells with 9-m-RA. However, 9-cis-RA treatment of the C57MG/Wnt-1 cell line induced a further 10-fold increase in Stra6 mRNA relative to either untreated C57MG/Wnt-1 or 9-cis-RA treated C57MG parent cells. Similar results were obtained with all-trans-RA.

It was possible that potential clonal variations in the C57MG/Wnt-1 cell line, that were unrelated to Wnt-1 expression, accounted for their differential response to retinoic acid relative to parental control cells. To address this, we tested the response of the parental C57MG cells to stimulation by soluble Wnt-3a in the presence or absence of 9-m-RA. Wnt-3a is a Wnt-1 homolog that exhibits transforming properties similar to those of Wnt-1 and can be produced as a soluble ligand in mouse L-cells. Conditioned media from cultured L-cells expressing Wnt-3a, but not from control L-cells, induced the expression of Stra6 in the C57MG cells (FIG. 17B). A slightly higher level of induction was observed on treatment of C57MG cells with 9-m-RA. However, the combination of 9-m-RA and Wnt-3a resulted in levels of Stra6 transcript vastly exceeding that seen with either agent alone.

If the induction of Stra6 in the retinoic acid treated C57MG/Wnt-1 cells was potentiated by increased β-catenin levels, then one might expect a similar induction of Stra6 in response to retinoic acid in human colon carcinoma cells containing mutations in either β-catenin or APC. To determine whether this occurs, Stra6 mRNA levels were measured before and after retinoic acid treatment in HCT116 cells, which carry an activating mutation in β-catenin, and in WiDr cells, which have lost both copies of wild-type APC. In both cell lines, a significant increase in Stra6 mRNA levels was seen following treatment with either ATRA or 9-m-RA compared to DMSO or vitamin D3 (FIG. 17C). The activation of the Stra6 gene by ATRA in the HCT116 cell line was confirmed by in situ hybridization (FIG. 17D). Induction of the predicted 73 kDa Stra6 protein band in WiDr cells treated with ATRA was detected by Western blot analysis with a Stra6 specific monoclonal antibody (FIG. 17E). Immunohistochemical analysis of the WiDr cells revealed that the increase in Stra6 protein in response to retinoic acid was localized to the plasma membrane (FIG. 17F).

The RARγ gene has been proposed as a target for Wnt signaling in Xenopus embryos, and the induction of Stra6 by retinoids was shown to be dependent upon the presence of this retinoic acid receptor subtype (McGrew et al., Mech. Dev. 87:21-32 [1999]; Taneja et al., Proc. Natl. Acad. Sci. USA 92:7854-8 [1995]). Together, these observations suggest that the synergistic activation of Stra6 by Wnt and retinoids might be due to the activation of RARγ expression by Wnt signaling. To determine whether Wnt-1 signaling had any influence over the levels of RARγ in mammalian cells, we performed Western blots for the receptor on lysates prepared from C57MG cells that conditionally express Wnt-1. Upon Wnt-1 expression, a protein reactive with antibody specific to RARγ-1, and migrating with an apparent molecular mass of 64 kDa, was induced at 24 hours and its expression was increased at 48 hours (FIG. 18A). We also analyzed hyperplastic mammary glands and mammary gland tumors obtained from Wnt-1 transgenic mice and detected elevated levels of RARγ mRNA in these tissues relative to normal mammary gland (FIG. 18B). The level of RARγ transcript present in equivalent amounts of RNA isolated from 19 adenocarcinomas was assessed by quantitative PCR. Notably, RARγ mRNA expression was increased approximately 2-4 fold in 14 of the 19 (74%) of human colon tumors examined compared to normal human colon tissue (FIG. 18C). These results demonstrate that Wnt-1 signaling promotes the expression of RARγ that the receptors are elevated in mouse and human tumors that are driven by the Wnt-1 pathway.

Discussion of Experimental Findings

Gene expression profiling approaches are based on unbiased detection of mRNA transcripts and can therefore lead to unexpected insights into the mechanisms by which gene activation occurs. Here it has been shown that Wnt-1 promoted the induction of the retinoic acid responsive gene Stra6, suggesting a connection between signaling pathways elicited by Wnt and retinoic acid. This connection was further supported by demonstrating a synergistic induction of Stra6 by a combination of Wnt and retinoic acid. There are at least three alternative explanations that could account for this synergy: i) transcription factors directly responsive to Wnt such as the TCF/LEFs might bind to and activate promoter elements in the Stra6 gene; ii) signaling components in the Wnt pathway might directly interact with the appropriate retinoic acid receptor (RAR) and potentiate gene activation mediated by the RAR; or iii) signaling by Wnt-1 could activate expression of the appropriate RAR, which could then sensitize cells to retinoic acid. Although this final proposal is favored because the data presented herein show that Wnt-1 signaling rapidly induces expression of the RARγ receptor, the present invention is not limited by any particular theory or mechanism of action.

Previous work has shown that specific disruption of the RARγ gene greatly reduced induction of the Stra6 gene by retinoids, which was then rescued on re-expression of this receptor (Taneja et al., supra). However, it remains possible that mechanisms in addition to the Wnt-1-induced expression of RARγ may also contribute to the observed synergy. The proposal that β-catenin binds to retinoic acid receptors is attractive, but we have not observed any specific association of endogenous RARγ with β-catenin in our cell lines. However, the binding of β-catenin to RARγ, as was shown in vitro (Easwaran et al., 1999, supra), might relate to the activation of Stra6 by Wnt-1. The expression pattern of Stra6 in transgenic animals null for RARγ was more widespread than that observed in wild-type littermates, and induction of Stra6 by retinoic acid was enhanced in cells from the null animals compared to controls (Bouillet et al., 1997, supra; Taneja et al., 1995. supra). Thus RARγ might be inhibitory to Stra6 expression, and activation of β-catenin by Wnt-1 could potentially relieve this inhibition if β-catenin inhibited RARγ function.

The synergistic induction of a retinoic acid responsive gene by Wnt-1 signaling implies that human cancers that harbor genetic defects in the Wnt-1 pathway would exhibit overexpression of Stra6. The vast majority of colorectal tumors contain mutations in the genes coding for either the APC tumor suppressor or β-catenin (Polakis, *Curr. Opin. Genet. Dev.* 9:15-21 [1999]) and, accordingly, we have detected overexpression of the Stra6 transcript in 14 of 14 colorectal tumors relative to matched normal tissue (see Example 12). Activating mutations in β-catenin have also been identified in cancers of the ovary and endometrium, Wilm's kidney tumors and melanomas, demonstrating that defects in Wnt-1 signaling contribute to the progression of these cancers (Kobayashi et al. *Jpn. J. Cancer Res.* 90:55-9 [1999]; Koesters et al., *Cancer Res.* 59:3880-2 [1999]; Palacios and Hamallo, *Cancer Res.* 58:1344-7 [1998]; Rimm et al. *Am. J. Pathol.* 154: 325-9 [1999]; Rubinfeld et al. *Science* 262:1731-1734 [1993]; Wright et al. *Int. J. Cancer* 82:625-9 [1999]). All four of these human cancers displayed overexpression of Stra6 mRNA as determined by in situ hybridization (see Example 12). Pheochromocytoma, a tumor derived from the adrenal medulla, exhibited extremely high levels of Stra6 mRNA, however, the status of these tumors with respect to mutations in the Wnt-1 signaling pathway has not been reported. It is intriguing that the cell types that give rise to melanomas and pheochromocytomas share in common an embryological derivation from the neural crest. Notably, Wilms' tumor of the kidney, pheochromocytoma, and endometrial carcinomas all arise in organs in which Stra6 is normally expressed. This suggests that tumorigenic signaling, such as that driven by the Wnt-1 pathway, might interact with signals responsible for differentiation, thereby hyper-activating the expression of Stra6.

The human Stra6 protein resides at the cell surface, as determined by the staining of colorectal cancer cells with monoclonal antibodies specific to human Stra6 protein. Moreover, the staining intensity observed at the cell membrane was increased after treatment of cells with retinoic acid. Thus, Stra6 likely encodes a multi-pass transmembrane protein that is localized to the cell surface.

Deposit of Material

The following materials have been deposited with the American Type Culture Collection, 10801 University Blvd., Manassas, Va. 20110-2209, USA (ATCC):

| Material | ATCC Dep. No. | Deposit Date |
|---|---|---|
| DNA148380-2827 | PTA-1181 | Jan. 11, 2000 |
| DNA148389-2827-1 | PTA-1405 | Feb. 23, 2000 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of diagnosing tumor in a mammal, said method comprising detecting expression of Stra6 polypeptide in a test sample of tissue or cells obtained from the mammal, and comparing expression of Stra6 polypeptide in the test sample to expression of Stra6 polypeptide in a control sample of normal tissue or cells of the same type as the test sample, wherein a higher expression of Stra6 polypeptide in the test sample as compared to the control sample is indicative of the presence of a tumor in the mammal.

2. A method of diagnosing tumor in a mammal, said method comprising (a) contacting an anti-Stra6 antibody with a test sample of tissue or cells obtained from the mammal, and (b) detecting formation of a complex between said antibody and a Stra6 polypeptide in the test sample, wherein the formation of a complex is indicative of the presence of tumor in said mammal.

3. The method of claim 2 wherein said antibody is detectably labeled.

4. The method of claim 2 wherein said test sample of tissue or cells is obtained from an individual suspected of having neoplastic cell growth or proliferation.

5. A method of identifying a compound that inhibits a biological or immunological activity of a Stra6 polypeptide, said method comprising contacting a candidate compound with said polypeptide under conditions and for a time sufficient to allow the two components to interact and determining whether a biological or immunological activity of said polypeptide is inhibited, relative to the biological or immunological activity of said polypeptide in the absence of said candidate compound.

6. The method of claim 5, wherein said candidate compound or said Stra6polypeptide is immobilized on a solid support.

7. The method of claim 6, wherein the non-immobilized component is detectably labeled.

8. A method for identifying a compound that inhibits an activity of a Stra6 polypeptide, said method comprising the steps of (a) contacting cells expressing Stra6polypeptide with a candidate compound, and (b) determining if the candidate compound inhibits a cellular response induced by expression of Stra6 polypeptide in said cells, wherein inhibition of said cellular response is indicative of said candidate compound being an effective inhibitor of Stra6 polypeptide.

9. A method for identifying a compound that inhibits expression of a Stra6 polypeptide in cells that express said polypeptide, wherein said method comprises contacting said cells with a candidate compound, and determining whether expression of said Stra6 polypeptide is inhibited.

10. The method of claim 5, wherein said candidate compound is an antibody or antibody fragment.

11. The method of claim 9, wherein said candidate compound is an antisense oligonucleotide.

12. The method of claim 1, wherein detecting expression of Stra6polypeptide comprises detecting expression of a polynucleotide encoding Stra6 polypeptide.

13. The method of claim 2, wherein the anti-Stra6 antibody comprises an antibody fragment, single chain antibody, diabody, or linear antibody.

14. The method of claim 13, wherein the antibody fragment comprises a Fab, Fab' F(ab')$_2$, or Fv fragment.

15. The method of claim 2, wherein the anti-Stra6 antibody binds to a Stra6 polypeptide consisting of at least 99% sequence identity to:
   (a) the sequence of amino acid residues 1 to 667 of FIG. 2 (SEQ ID NO:2); or
   (b) the sequence of amino acids 1 to 658 of FIG. 7 (SEQ ID NO:5).

16. The method of claim 2, wherein the anti-Stra6 antibody binds to a Stra6 polypeptide consisting of at least 95% sequence identity to:
   (a) the sequence of amino acid residues 1 to 667 of FIG. 2 (SEQ ID NO:2); or
   (b) the sequence of amino acids 1 to 658 of FIG. 7 (SEQ ID NO:5).

17. The method of claim 13, wherein the antibody or antibody fragment thereof binds to a Stra6 polypeptide having an extracellular domain comprising the amino acid sequence of amino acids 229 to 295 or 532 to 667 of SEQ ID NO:2.

18. The method of claim 2, wherein the anti-Stra6 antibody was raised against amino acid residues 229 to 295 or 532 to 667 of SEQ ID NO:2.

19. The method of claim 5, wherein Stra6 polypeptide comprises at least 95% sequence identity to:
   (a) the sequence of amino acid residues 1 to 667 of FIG. 2 (SEQ ID NO:2); or
   (b) the sequence of amino acids 1 to 658 of FIG. 7 (SEQ ID NO:5).

20. The method of claim 8, wherein Stra6 polypeptide comprises at least 95% sequence identity to:
   (a) the sequence of amino acid residues 1 to 667 of FIG. 2 (SEQ ID NO:2); or
   (b) the sequence of amino acids 1 to 658 of FIG. 7 (SEQ ID NO:5).

21. The method of claim 9, wherein Stra6 polypeptide comprises at least 95% sequence identity to:
   (a) the sequence of amino acid residues 1 to 667 of FIG. 2 (SEQ ID NO:2); or
   (b) the sequence of amino acids 1 to 658 of FIG. 7 (SEQ ID NO:5).

22. The method of claim 12, wherein the polynucleotide encodes a Stra6 polypeptide comprising at least 95% sequence identity to:
   (a) the sequence of amino acid residues 1 to 667 of FIG. 2 (SEQ ID NO:2); or
   (b) the sequence of amino acids 1 to 658 of FIG. 7 (SEQ ID NO:5).

23. The method of claim 12, wherein the polynucleotide encodes a Stra6 polypeptide having an extracellular domain comprising the amino acid sequence of amino acids 229 to 295 or 532 to 667 of SEQ ID NO:2.

* * * * *

UNITED STATES PATENT AND TRADEMARK OFFICE
CERTIFICATE OF CORRECTION

PATENT NO. : 7,939,650 B2
APPLICATION NO. : 11/458181
DATED : May 10, 2011
INVENTOR(S) : Pennica et al.

It is certified that error appears in the above-identified patent and that said Letters Patent is hereby corrected as shown below:

Page 2, Foreign Patent Documents: "WO    WO 9L/00360    1/1991" should read
--WO    WO 91/00360    1/1991--

Col. 7, line 25: "position S4 to about" should read --position 54 to about--

Col. 17, line 55: "89% ammo acid sequence" should read --89% amino acid sequence--

Col. 29, line 48: "daunomycin, caminomycin, aminopterin," should read --daunomycin, carminomycin, aminopterin,--

Col. 31, line 36: "The tern "antisense" refers" should read --The term "antisense" refers--

Col. 32, line 20: "with Slra6, a" should read --with Stra6, a--

Col. 32, line 21: "to relinoic acid" should read --to retinoic acid--

Col. 34, line 13: "asn, gin, his," should read --asn, gln, his,--

Col. 34, line 15: "tip, tyr," should read --trp, tyr,--

Col. 35, line 46: "*Biochem.*, 1J8:131" should read --*Biochem.*, 118: 131--

Col. 37, line 31: "first lime, and," should read --first time, and,--

Col. 38, line 2: "polybrene, poly ornithine, may also" should read --polybrene, polyornithine, may also--

Col. 39, line 22: "mammary rumor" should read --mammary tumor--

Signed and Sealed this
Twelfth Day of June, 2012

David J. Kappos
*Director of the United States Patent and Trademark Office*

CERTIFICATE OF CORRECTION (continued)

U.S. Pat. No. 7,939,650 B2

Col. 40, line 33: "tryptophan (tip) promoter" should read --tryptophan (trp) promoter--

Col. 40, line 46: "glucoses-phosphate isomerase," should read --glucose-6-phosphate isomerase,--

Col. 44, line 28: "(LT10), SRCC725" should read --(LT1), SRCC725--

Col. 45, line 29: "breast rumor center" should read --breast tumor center--

Col. 47, line 16: "from rumors in" should read --from tumors in--

Col. 48, line 49: "rumors, can be" should read --tumors, can be--

Col. 68, line 49: "include immothioiate and" should read --include iminothiolate and--

Col. 77, line 16: "known in die art, and" should read --known in the art, and--

Col. 77, line 39: "to verity expression" should read --to verify expression--

Col. 80, line 27: "such as by $Nr^{2+}$-chelate" should read --such as by $Ni^{2+}$-chelate--

Col. 81, line 15: "die production, the pH" should read --the production, the pH--

Col. 86, lines 24-25: "*Biochemistry*, 3L7796-7801" should read --*Biochemistry*, 31:7796-7801--

Col. 114, line 63, claim 2: "and a Stra6polypeptide in the" should read --and a Stra6 polypeptide in the--

Col. 115, line 14, claim 6: "said Stra6polypeptide is" should read --said Stra6 polypeptide is--

Col. 115, line 20, claim 8: "expressing Stra6polypeptide with" should read --expressing Stra6 polypeptide with--

Col. 115, line 36, claim 12: "Stra6polypeptide comprises" should read --Stra6 polypeptide comprises--